US008909595B2

(12) United States Patent
Gandy et al.

(10) Patent No.: US 8,909,595 B2
(45) Date of Patent: Dec. 9, 2014

(54) METHOD FOR ENTERING, RECORDING, DISTRIBUTING AND REPORTING DATA

(75) Inventors: Woodrow W. Gandy, Dallas, TX (US); Robert W. Langdon, Dallas, TX (US); Scott A. Stoll, Plano, TX (US); James E. Slagle, Dallas, TX (US)

(73) Assignee: T-System, Inc., Dallas, TX (US)

( * ) Notice: Subject to any disclaimer, the term of this patent is extended or adjusted under 35 U.S.C. 154(b) by 693 days.

(21) Appl. No.: 11/132,948

(22) Filed: May 20, 2005

(65) Prior Publication Data

US 2005/0216455 A1 Sep. 29, 2005

Related U.S. Application Data

(62) Division of application No. 09/927,972, filed on Aug. 10, 2001.

(60) Provisional application No. 60/309,452, filed on Aug. 1, 2001.

(51) Int. Cl.

| | |
|---|---|
| ***G06F 7/00*** | (2006.01) |
| ***G06F 17/24*** | (2006.01) |
| ***G06F 17/30*** | (2006.01) |
| ***G06F 19/00*** | (2011.01) |

(52) U.S. Cl.

CPC ........ *G06F 17/243* (2013.01); *G06F 17/30696* (2013.01); *G06F 19/322* (2013.01); *G06F 19/3406* (2013.01); *G06F 19/3487* (2013.01); *G06F 19/363* (2013.01)

USPC ........................................... 707/603; 707/831

(58) Field of Classification Search

CPC ................ G06F 17/27; G06F 17/2872; G06F 17/30684; G06F 17/30707; G06F 17/30663; G06F 17/30654; G06F 17/30696; G06F 17/30011; G06F 17/30436; G06F 17/30634; Y10S 707/99931

USPC .................. 707/1–104.1, 100, 102, 603, 800, 707/797–798, 828–831, 778; 717/140, 145, 717/148, 150; 715/256–268, 780, 708, 715/817–822; 345/689; 706/924

See application file for complete search history.

(56) References Cited

U.S. PATENT DOCUMENTS

| | | | |
|---|---|---|---|
| 4,829,423 | A | 5/1989 | Tennant et al. |
| 4,969,096 | A | 11/1990 | Rosen et al. |
| 5,033,812 | A | 7/1991 | Yoshida et al. |
| 5,065,315 | A | 11/1991 | Garcia |
| 5,101,459 | A | 3/1992 | Sunagawa et al. |
| 5,132,843 | A | 7/1992 | Aoyama et al. |
| 5,265,010 | A | 11/1993 | Evans-Paganelli et al. |
| 5,301,105 | A | 4/1994 | Cummings, Jr. |
| 5,319,543 | A | 6/1994 | Wilhelm |
| 5,384,702 | A | 1/1995 | Tou |
| 5,436,991 | A | 7/1995 | Sunagawa et al. |
| 5,519,608 | A | 5/1996 | Kupiec |

(Continued)

FOREIGN PATENT DOCUMENTS

| | | |
|---|---|---|
| JP | 63-106605 | 5/1988 |
| JP | 2001 4877 | 1/2001 |

*Primary Examiner* — James Trujillo
*Assistant Examiner* — Linh Black
(74) *Attorney, Agent, or Firm* — Fulbright & Jaworski LLP

(57) ABSTRACT

An improved method for efficiently and accurately entering detailed data by yes/no entries so that the data is automatically recorded, optionally automatically distributed and optionally transformed into a readable prose report of the data, which is entered by yes/no markings.

21 Claims, 36 Drawing Sheets

(56) References Cited

U.S. PATENT DOCUMENTS

| | | | | |
|---|---|---|---|---|
| 5,546,580 | A | 8/1996 | Seliger et al. | |
| 5,583,762 | A | 12/1996 | Shafer | |
| 5,608,898 | A | 3/1997 | Turpin et al. | |
| 5,659,640 | A | 8/1997 | Joyner | |
| 5,715,468 | A * | 2/1998 | Budzinski | 704/9 |
| 5,721,938 | A | 2/1998 | Stuckey | |
| 5,742,433 | A | 4/1998 | Shiono et al. | |
| 5,794,177 | A | 8/1998 | Carus et al. | |
| 5,819,274 | A | 10/1998 | Jackson, Jr. | |
| 5,835,900 | A | 11/1998 | Fagg, III et al. | |
| 5,867,821 | A | 2/1999 | Ballantyne et al. | |
| 5,871,019 | A | 2/1999 | Belohlavek | |
| 5,899,998 | A | 5/1999 | McGauley et al. | |
| 5,924,074 | A | 7/1999 | Evans | |
| 5,937,385 | A | 8/1999 | Zadrozny et al. | |
| 5,956,711 | A * | 9/1999 | Sullivan et al. | 707/6 |
| 5,960,384 | A * | 9/1999 | Brash | 704/9 |
| 5,963,940 | A * | 10/1999 | Liddy et al. | 1/1 |
| 5,966,686 | A | 10/1999 | Heidorn et al. | |
| 5,995,077 | A | 11/1999 | Wilcox et al. | |
| 6,009,420 | A | 12/1999 | Fagg, III et al. | |
| 6,012,035 | A | 1/2000 | Freeman, Jr. et al. | |
| 6,026,363 | A | 2/2000 | Shepard | |
| 6,029,158 | A | 2/2000 | Bertrand et al. | |
| 6,040,821 | A * | 3/2000 | Franz et al. | 345/159 |
| 6,108,665 | A * | 8/2000 | Bair et al. | 707/104.1 |
| 6,139,494 | A | 10/2000 | Cairnes et al. | |
| 6,151,581 | A | 11/2000 | Kraftson et al. | |
| 6,154,726 | A | 11/2000 | Rensimer et al. | |
| 6,199,034 | B1 * | 3/2001 | Wical | 704/9 |
| 6,208,974 | B1 | 3/2001 | Campbell et al. | |
| 6,285,813 | B1 | 9/2001 | Schultz et al. | |
| 6,384,815 | B1 | 5/2002 | Huang | |
| 6,524,241 | B2 | 2/2003 | Iliff | |
| 6,556,977 | B1 | 4/2003 | Lapointe et al. | |
| 6,609,091 | B1 * | 8/2003 | Budzinski | 704/9 |
| 6,632,251 | B1 * | 10/2003 | Rutten et al. | 715/205 |
| 6,684,188 | B1 * | 1/2004 | Mitchell et al. | 705/3 |
| 6,766,316 | B2 * | 7/2004 | Caudill et al. | 1/1 |
| 6,788,847 | B2 | 9/2004 | Paddon et al. | |
| 6,871,140 | B1 | 3/2005 | Florance et al. | |
| 6,947,779 | B2 * | 9/2005 | Yamamoto et al. | 600/323 |
| 2001/0023419 | A1 | 9/2001 | Lapointe et al. | |
| 2001/0029322 | A1 | 10/2001 | Iliff | |
| 2001/0037219 | A1 | 11/2001 | Malik | |
| 2001/0041991 | A1 | 11/2001 | Segal et al. | |
| 2002/0002502 | A1 | 1/2002 | Maes et al. | |
| 2002/0004729 | A1 | 1/2002 | Zak et al. | |
| 2002/0010679 | A1 | 1/2002 | Felsher | |
| 2002/0016718 | A1 | 2/2002 | Rothschild et al. | |
| 2002/0029157 | A1 * | 3/2002 | Marchosky | 705/3 |
| 2002/0050982 | A1 | 5/2002 | Ericson | |
| 2002/0082868 | A1 * | 6/2002 | Pories et al. | 705/3 |
| 2002/0128816 | A1 | 9/2002 | Haug et al. | |
| 2002/0170565 | A1 * | 11/2002 | Walker et al. | 128/920 |
| 2003/0004983 | A1 * | 1/2003 | Cohen | 707/500 |
| 2003/0009367 | A1 * | 1/2003 | Morrison | 705/9 |
| 2003/0023473 | A1 * | 1/2003 | Guyan et al. | 705/9 |
| 2003/0058277 | A1 | 3/2003 | Bowman-Amuah | |
| 2003/0068134 | A1 | 4/2003 | Gunn | |
| 2003/0191627 | A1 * | 10/2003 | Au | 704/9 |
| 2004/0003142 | A1 | 1/2004 | Yokota et al. | |
| 2004/0054630 | A1 | 3/2004 | Ginter et al. | |
| 2004/0172295 | A1 | 9/2004 | Dahlin et al. | |

* cited by examiner

```
PHYSICAL EXAM - Skin Findings        ☐ ▢ ☒

Yes No                                ┌ OK ┐
 ☑  ☐ cyanosis                        └────┘
 ☐  ☐ cool skin                       ┌──────┐
 ☐  ☑ skin rash                       │Cancel│
 ☐  ☐ pallor                          └──────┘
 ☐  ☐ diaphoresis
 ☐  ☐ poor skin turgor
```

| User | | | ☒ |
|---|---|---|---|
| ☐ | ☐ | ☐ | ☐ |
| 1 | 2<br>abc | 3<br>def | |
| 4<br>ghi | 5<br>jkl | 6<br>mno | |
| 7<br>prs | 8<br>tuv | 9<br>xyz | |
| ◀ | 0<br>qz | C | |

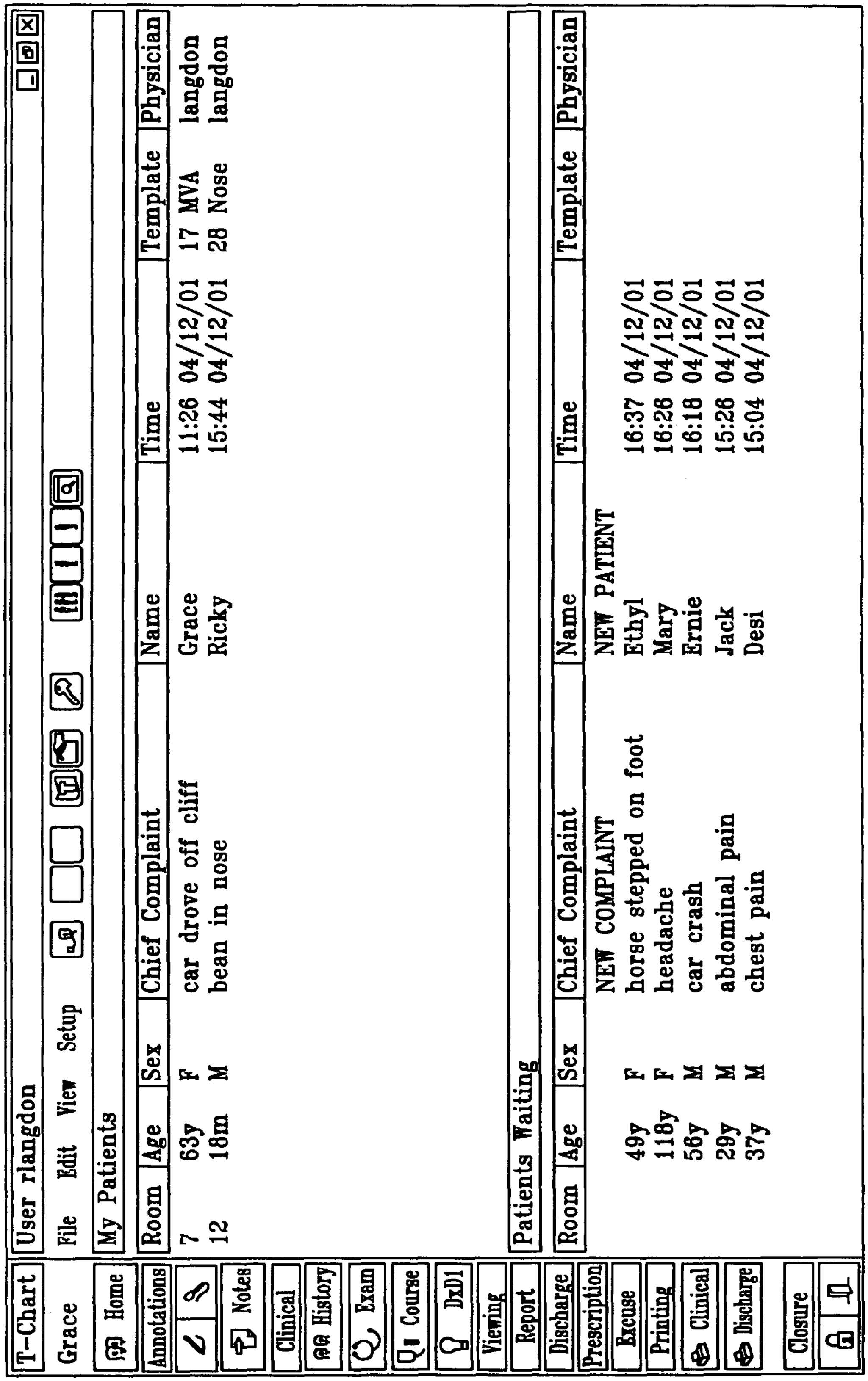

FIG. 3

| T-Chart | User rlangdon | | | | | | | □ ⊡ ⊠ |
|---------|---------------|---|---|---|---|---|---|
| Grace | File Edit View Setup | | | 🔍 ▢ ▢ 🔧 ▦ ▯ ▯ ▯ | | | | |

My Patients

| Room | Age | Sex | Chief Complaint | Name | Time | Template | Physician |
|------|-----|-----|-----------------|------|------|----------|-----------|
| 7 | 63y | F | car drove off cliff | Grace | 11:26 04/12/01 | 17 MVA | langdon |
| 12 | 18m | M | bean in nose | Ricky | 15:44 04/12/01 | 28 Nose | langdon |

Patients Waiting

| Room | Age | Sex | Chief Complaint | Name | Time | Template | Physician |
|------|-----|-----|-----------------|------|------|----------|-----------|
| | | | NEW COMPLAINT | NEW PATIENT | | | |
| | 49y | F | horse stepped on foot | Ethyl | 16:37 04/12/01 | | |
| | 118y | F | headache | Mary | 16:28 04/12/01 | | |
| | 56y | M | car crash | Ernie | 16:18 04/12/01 | | |
| | 29y | M | abdominal pain | Jack | 15:26 04/12/01 | | |
| | 37y | M | chest pain | Desi | 15:04 04/12/01 | | |

- Home
- Annotations
- Notes
- Clinical
- History
- Exam
- Course
- DxDl
- Viewing
- Report
- Discharge
- Prescription
- Excuse
- Printing
- Clinical
- Discharge
- Closure

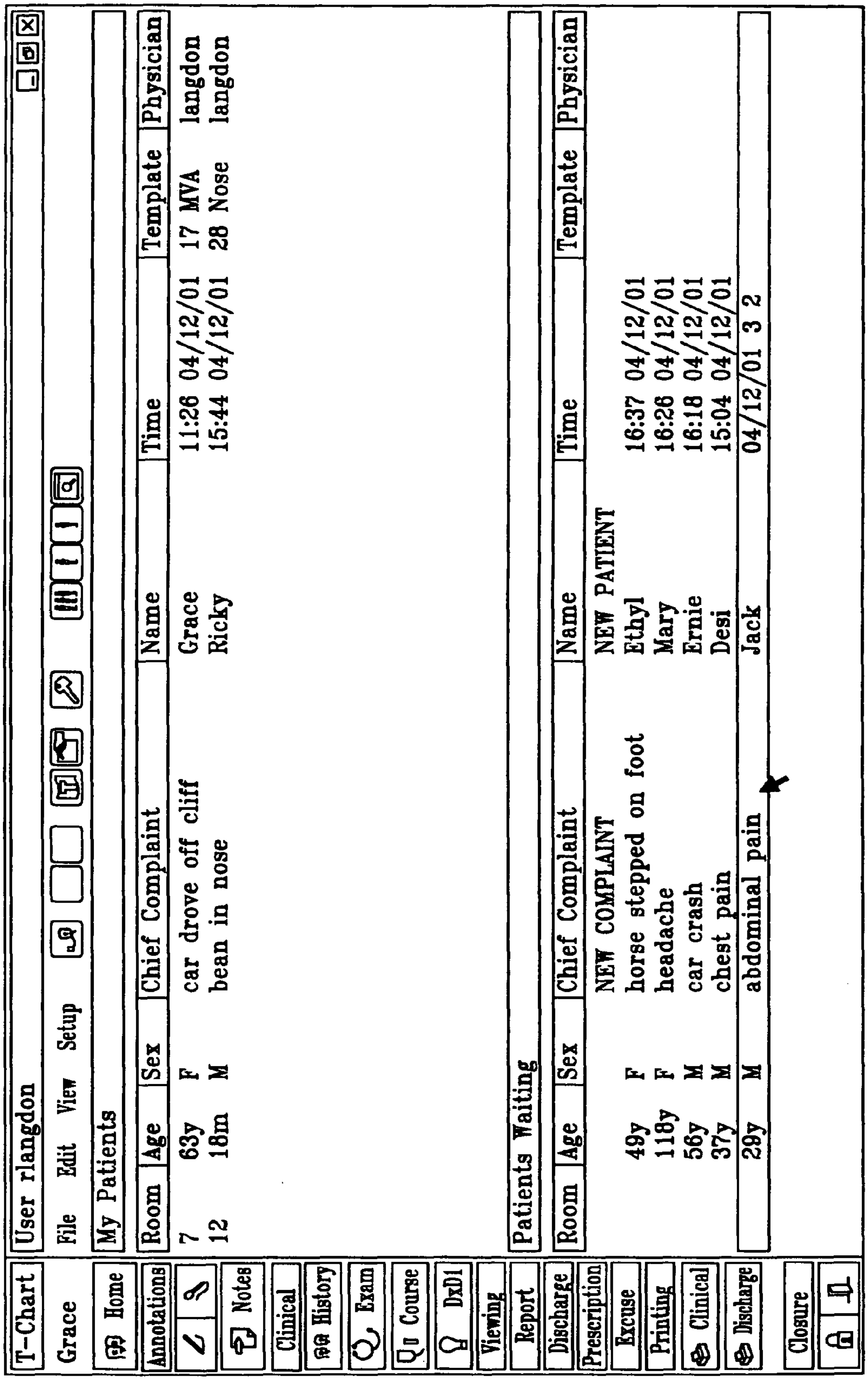

FIG. 4

| T-Chart | User rlangdon | | | | | | | | _ □ ☒ |
|---------|---|---|---|---|---|---|---|---|---|
| Grace | File Edit View Setup | | | | | | | | |

My Patients

| | Room | Age | Sex | Chief Complaint | Name | Time | | Template | Physician |
|---|---|---|---|---|---|---|---|---|---|
| Annotations | 7 | 63y | F | car drove off cliff | Grace | 11:26 | 04/12/01 | 17 MVA | langdon |
| Notes | 12 | 18m | M | bean in nose | Ricky | 15:44 | 04/12/01 | 28 Nose | langdon |

Clinical
History
Exam
Course
Dx D1
Viewing
Report
Discharge
Prescription

Patients Waiting

| | Room | Age | Sex | Chief Complaint | Name | Time | | Template | Physician |
|---|---|---|---|---|---|---|---|---|---|
| Excuse | | 49y | F | NEW COMPLAINT | NEW PATIENT | | | | |
| Printing | | | | horse stepped on foot | Ethyl | 16:37 | 04/12/01 | | |
| | | 118y | F | headache | Mary | 16:26 | 04/12/01 | | |
| Clinical | | 56y | M | car crash | Ernie | 16:18 | 04/12/01 | | |
| Discharge | | 37y | M | chest pain | Desi | 15:04 | 04/12/01 | | |
| | | 29y | M | abdominal pain | Jack | 04/12/01 | 3 | 2 | |

Closure

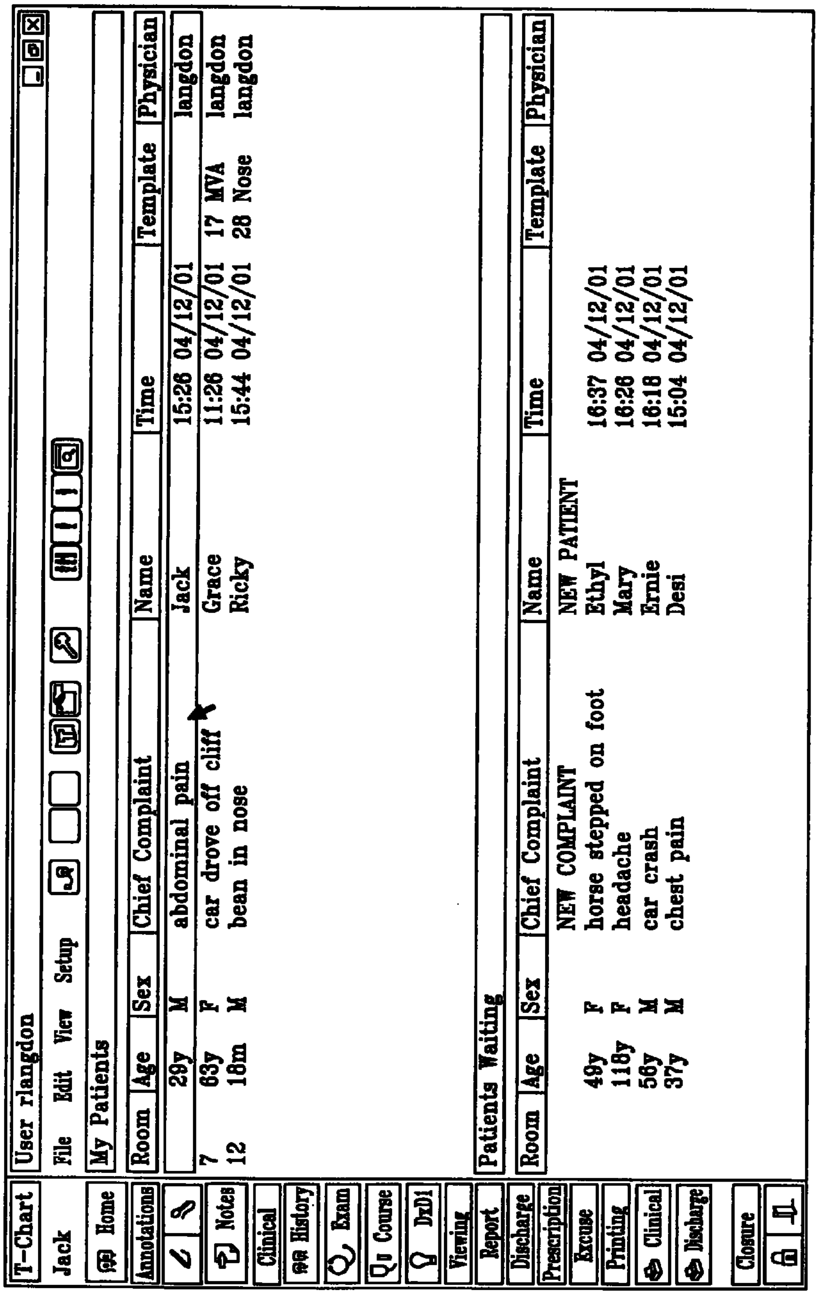

FIG. 5

| T-Chart | User rlangdon | | | | | | | |
|---|---|---|---|---|---|---|---|---|
| Jack | File Edit View Setup | | | | | | | |
| Home | My Patients | | | | | | | |
| Annotations | Room | Age | Sex | Chief Complaint | Name | Time | Template | Physician |
|  | | 28y | M | abdominal pain | Jack | 15:26 04/12/01 | | langdon |
| Notes | 7 | 63y | F | car drove off cliff | Grace | 11:26 04/12/01 | 17 MVA | langdon |
|  | 12 | 18m | M | bean in nose | Ricky | 15:44 04/12/01 | 28 Nose | langdon |
| Clinical | | | | | | | | |
| History | | | | | | | | |
| Exam | | | | | | | | |
| Course | | | | | | | | |
| DrDl | | | | | | | | |
| Viewing | | | | | | | | |
| Report | Patients Waiting | | | | | | | |
| Discharge | Room | Age | Sex | Chief Complaint | Name | Time | Template | Physician |
| Prescription | | | | NEW COMPLAINT | NEW PATIENT | | | |
| Excuse | | 49y | F | horse stepped on foot | Ethyl | 16:37 04/12/01 | | |
| Printing | | 118y | F | headache | Mary | 16:26 04/12/01 | | |
| Clinical | | 56y | M | car crash | Ernie | 16:18 04/12/01 | | |
| Discharge | | 37y | M | chest pain | Desi | 15:04 04/12/01 | | |
| Closure | | | | | | | | |

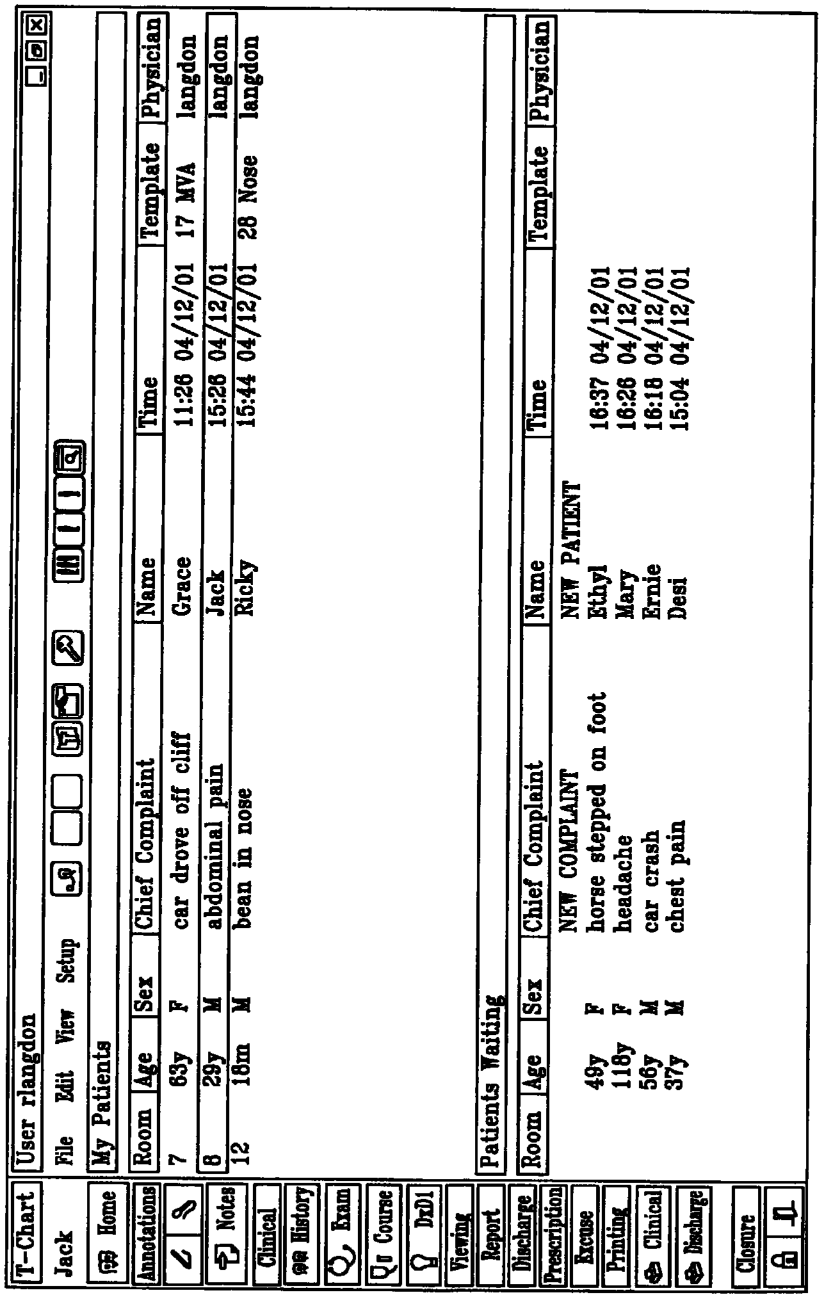

FIG. 6

| T-Chart | User rlangdon | | | | | | |
|---|---|---|---|---|---|---|---|
| Jack | File Edit View Setup | | | | | | |
| Home | My Patients | | | | | | |
| Annotations | Room | Age | Sex | Chief Complaint | Name | Time | Template | Physician |
|  | 7 | 63y | F | car drove off cliff | Grace | 11:26 04/12/01 | 17 MVA | langdon |
| Notes | 8 | 29y | M | abdominal pain | Jack | 15:26 04/12/01 | | langdon |
| Clinical | 12 | 18m | M | bean in nose | Ricky | 15:44 04/12/01 | 28 Nose | langdon |
| History | | | | | | | | |
| Exam | Patients Waiting | | | | | | |
| U Course | Room | Age | Sex | Chief Complaint | Name | Time | Template | Physician |
| DrDl | | | | NEW COMPLAINT | NEW PATIENT | | | |
| Viewing | | 49y | F | horse stepped on foot | Ethyl | 16:37 04/12/01 | | |
| Report | | 118y | F | headache | Mary | 16:26 04/12/01 | | |
| Discharge | | 56y | M | car crash | Ernie | 16:18 04/12/01 | | |
| Prescription | | 37y | M | chest pain | Desi | 15:04 04/12/01 | | |
| Excuse | | | | | | | | |
| Printing | | | | | | | | |
| Clinical | | | | | | | | |
| Discharge | | | | | | | | |
| Closure | | | | | | | | |

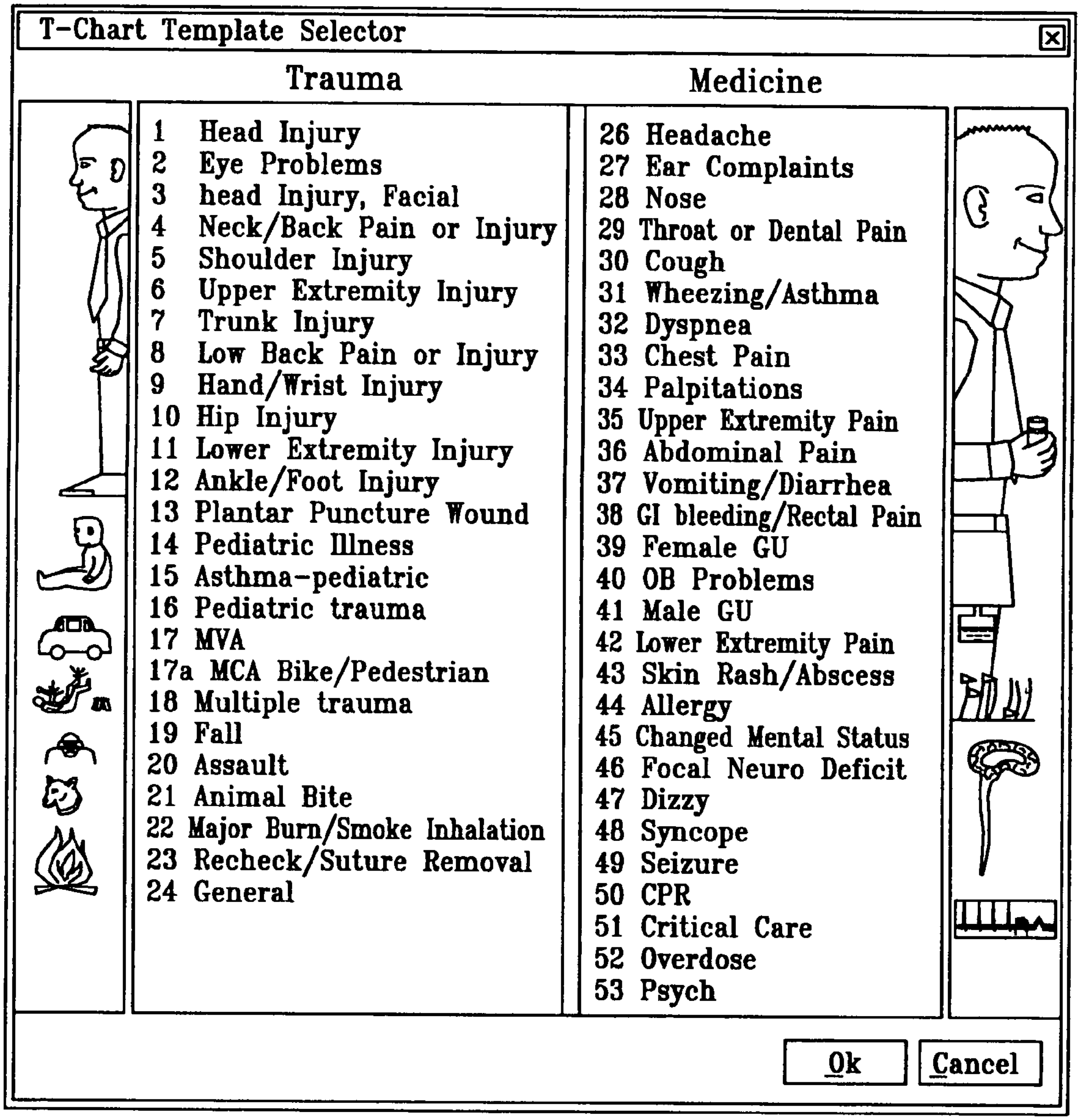

FIG. 7

| Trauma | Medicine |
|---|---|
| 1 Head Injury | 26 Headache |
| 2 Eye Problems | 27 Ear Complaints |
| 3 head Injury, Facial | 28 Nose |
| 4 Neck/Back Pain or Injury | 29 Throat or Dental Pain |
| 5 Shoulder Injury | 30 Cough |
| 6 Upper Extremity Injury | 31 Wheezing/Asthma |
| 7 Trunk Injury | 32 Dyspnea |
| 8 Low Back Pain or Injury | 33 Chest Pain |
| 9 Hand/Wrist Injury | 34 Palpitations |
| 10 Hip Injury | 35 Upper Extremity Pain |
| 11 Lower Extremity Injury | 36 Abdominal Pain |
| 12 Ankle/Foot Injury | 37 Vomiting/Diarrhea |
| 13 Plantar Puncture Wound | 38 GI bleeding/Rectal Pain |
| 14 Pediatric Illness | 39 Female GU |
| 15 Asthma-pediatric | 40 OB Problems |
| 16 Pediatric trauma | 41 Male GU |
| 17 MVA | 42 Lower Extremity Pain |
| 17a MCA Bike/Pedestrian | 43 Skin Rash/Abscess |
| 18 Multiple trauma | 44 Allergy |
| 19 Fall | 45 Changed Mental Status |
| 20 Assault | 46 Focal Neuro Deficit |
| 21 Animal Bite | 47 Dizzy |
| 22 Major Burn/Smoke Inhalation | 48 Syncope |
| 23 Recheck/Suture Removal | 49 Seizure |
| 24 General | 50 CPR |
| | 51 Critical Care |
| | 52 Overdose |
| | 53 Psych |

Ok  Cancel

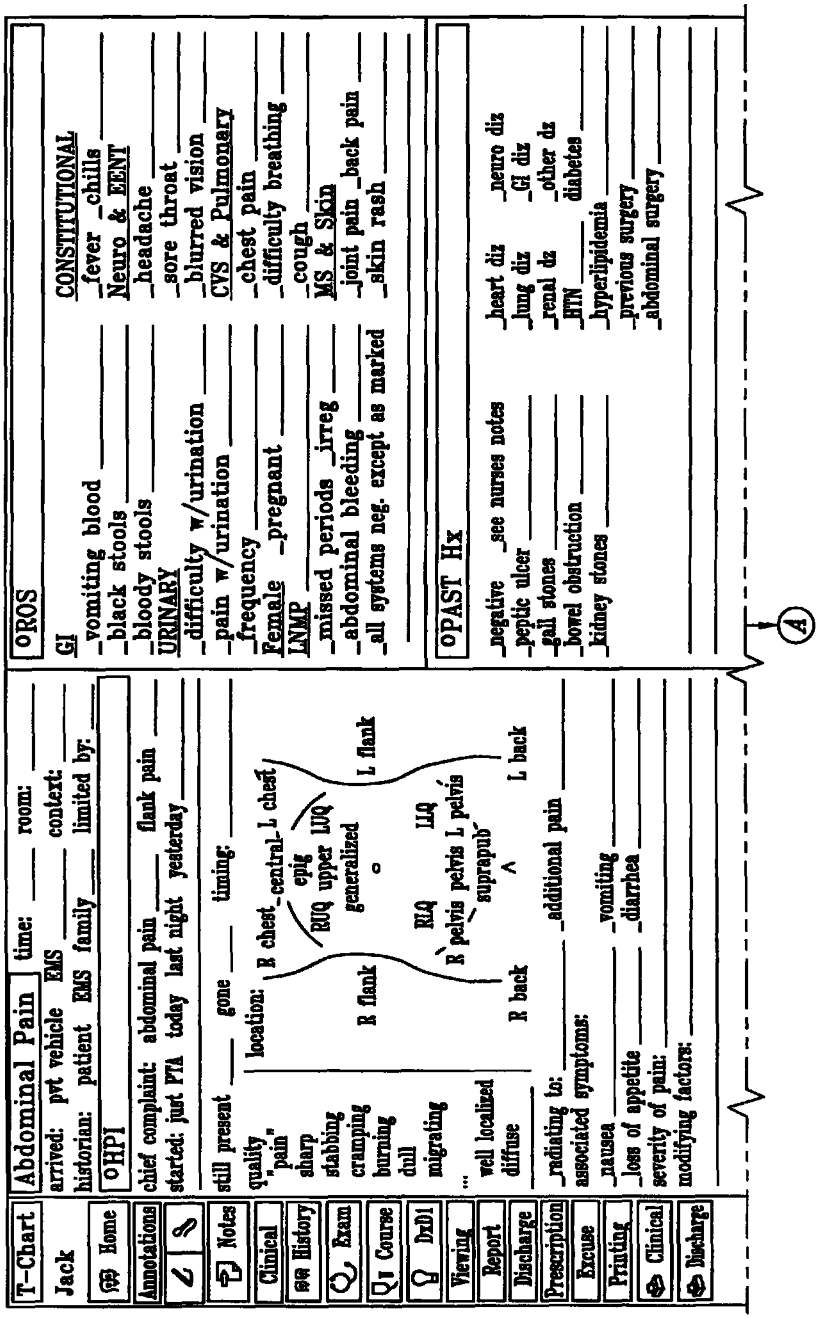

FIG. 9A

| T-Chart | Abdominal Pain | time: | room: |
|---|---|---|---|
| Jack | arrived: pvt vehicle EMS | | context: |
| | historian: patient EMS family | | limited by: |

Annotations

OHPI chief complaint: abdominal pain ___ flank pain ___
started: just PTA today last night yesterday ___ still present ___ gone ___ timing: ___ quality, location: R chest_central_L chest
"pain",          epig
sharp       RUQ upper LUQ
stabbing         generalized     L flank
cramping    R flank     o
burning              RLQ   LLQ
dull           R pelvis pelvis L pelvis
migrating        suprapub
                   ∧
well localized    R back       L back
diffuse radiating to: ___ additional pain ___
associated symptoms:
__nausea __vomiting
__loss of appetite __diarrhea
severity of pain:
modifying factors:

OROS

GI
__vomiting blood
__black stools
__bloody stools
URINARY
__difficulty w/urination
__pain w/urination
__frequency
Female __pregnant
LNMP
__missed periods __irreg
__abdominal bleeding
__all systems neg. except as marked CONSTITUTIONAL
__fever __chills
Neuro & EENT
__headache
__sore throat
__blurred vision
CVS & Pulmonary
__chest pain
__difficulty breathing
__cough
MS & Skin
__joint pain __back pain
__skin rash

OPAST Hx

__negative __see nurses notes    __heart dz __neuro dz
__peptic ulcer    __lung dz __GI dz
__gall stones    __renal dz __other dz
__bowel obstruction    __HTN __diabetes
__kidney stones    __hyperlipidemia
   __previous surgery
   __abdominal surgery Sidebar: Home, Annotations, Notes, Clinical, History, Exam, T Course, DrDI, Viewing, Report, Discharge, Prescription, Excuse, Printing, Clinical, Discharge

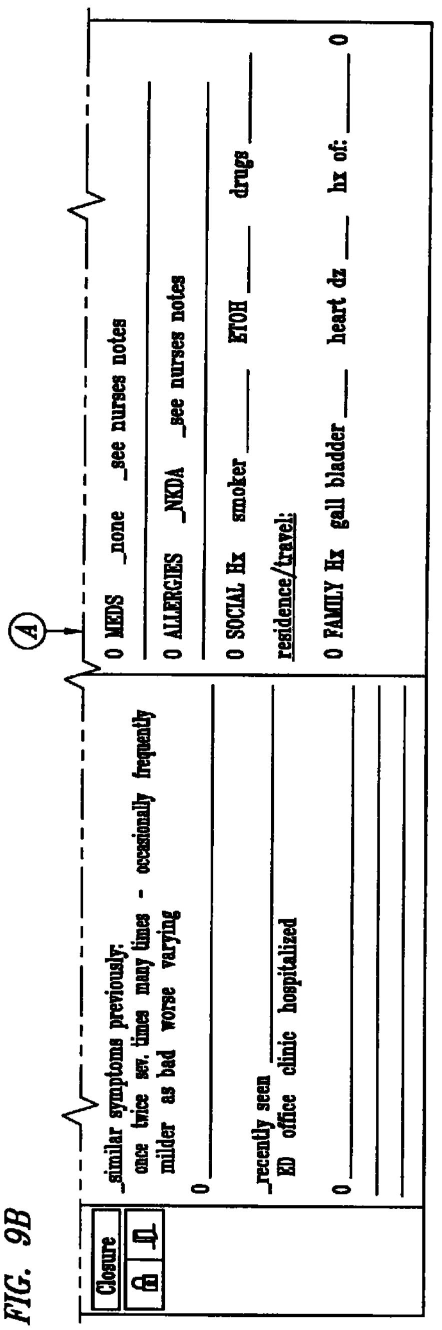

FIG. 10

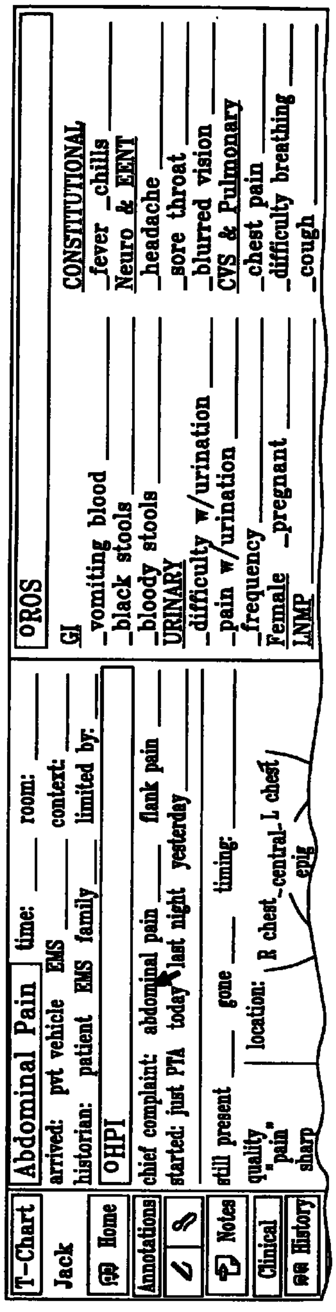

| Closure | |
|---|---|
| 🏠 🔒 | |

similar symptoms previously:
once twice sev. times many times - occasionally frequently
milder as bad worse varying
O
_recently seen
ED office clinic hospitalized
O (A)→

O MEDS __none __see nurses notes
O ALLERGIES __NKDA __see nurses notes
O SOCIAL Hx __smoker_____ ETOH_____ drugs_____
residence/travel:
O FAMILY Hx gall bladder_____ heart dz_____ hx of:_____ O

| T-Chart | Abdominal Pain | time: | room: |
|---|---|---|---|
| Jack | arrived: prt vehicle EMS | | context: |
| 🏠 Home | historian: patient EMS family | | limited by: |
| Annotations ✏️ 🔗 | OHPI | | |
| | chief complaint: abdominal pain flank pain | | |
| 📝 Notes | started: just PTA today last night yesterday | | |
| Clinical | still present___ gone___ timing:___ | | |
| 📖 History | quality: location: R chest _central_ L chest_ | | |
| | "pain" epig | | |
| | sharp | | |

| OROS | |
|---|---|
| GI | CONSTITUTIONAL |
| _vomiting blood | _fever _chills |
| _black stools | Neuro & EENT |
| _bloody stools | _headache |
| URINARY | _sore throat |
| _difficulty w/urination | _blurred vision |
| _pain w/urination | CVS & Pulmonary |
| _frequency | _chest_pain |
| _Female _pregnant | _difficulty breathing |
| LNMP | _cough |

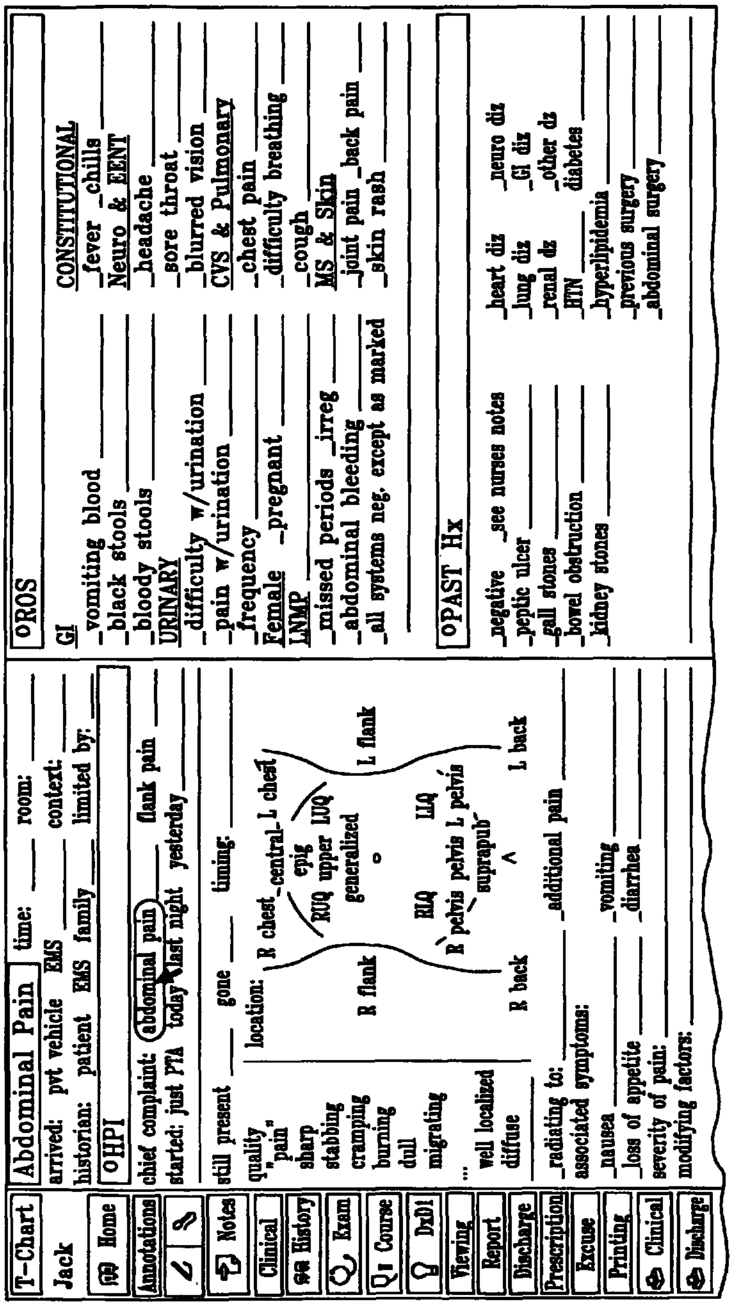

FIG. 11

| T-Chart | Abdominal Pain | time: | room: |
|---|---|---|---|
| Jack | arrived: pvt vehicle EMS | | context: |
| | historian: patient EMS family | | limited by: |

Home
Annotations — chief complaint: (abdominal pain) flank pain
✎ — started: just PTA today last night yesterday
Notes — OHPI
Clinical — still present ____ gone ____ timing: ____
History — quality    location:         R chest_central_L chest
Exam — "pain"                    epig
Clinical Course — sharp              RUQ upper LUQ
DDl — stabbing                generalized       L flank
Viewing — cramping         R flank
Report — burning                        RLQ  LLQ
Discharge — dull                         R pelvis pelvis L pelvis
Prescription — migrating                    suprapub
Excuse — ...                              <
Printing — well localized         R back            L back
Clinical — diffuse
Discharge — radiating to: ____ additional pain ____
  associated symptoms: ____ vomiting ____
  nausea ____ diarrhea ____
  loss of appetite
  severity of pain:
  modifying factors:

OROS
GI
  _vomiting blood
  _black stools
  _bloody stools
URINARY
  _difficulty w/urination
  _pain w/urination
  _frequency
Female _pregnant
LNMP
  _missed periods _irreg
  _abdominal bleeding
  _all systems neg. except as marked CONSTITUTIONAL
  _fever _chills
Neuro & EENT
  _headache
  _sore throat
  _blurred vision
CVS & Pulmonary
  _chest pain
  _difficulty breathing
  _cough
MS & Skin
  _joint pain _back pain
  _skin rash OPAST Hx
  _negative _see nurses notes
  _peptic ulcer
  _gall stones
  _bowel obstruction
  _kidney stones _heart dz   _neuro dz
  _lung dz    _GI dz
  _renal dz   _other dz
  HTN         diabetes
  _hyperlipidemia
  _previous surgery
  _abdominal surgery

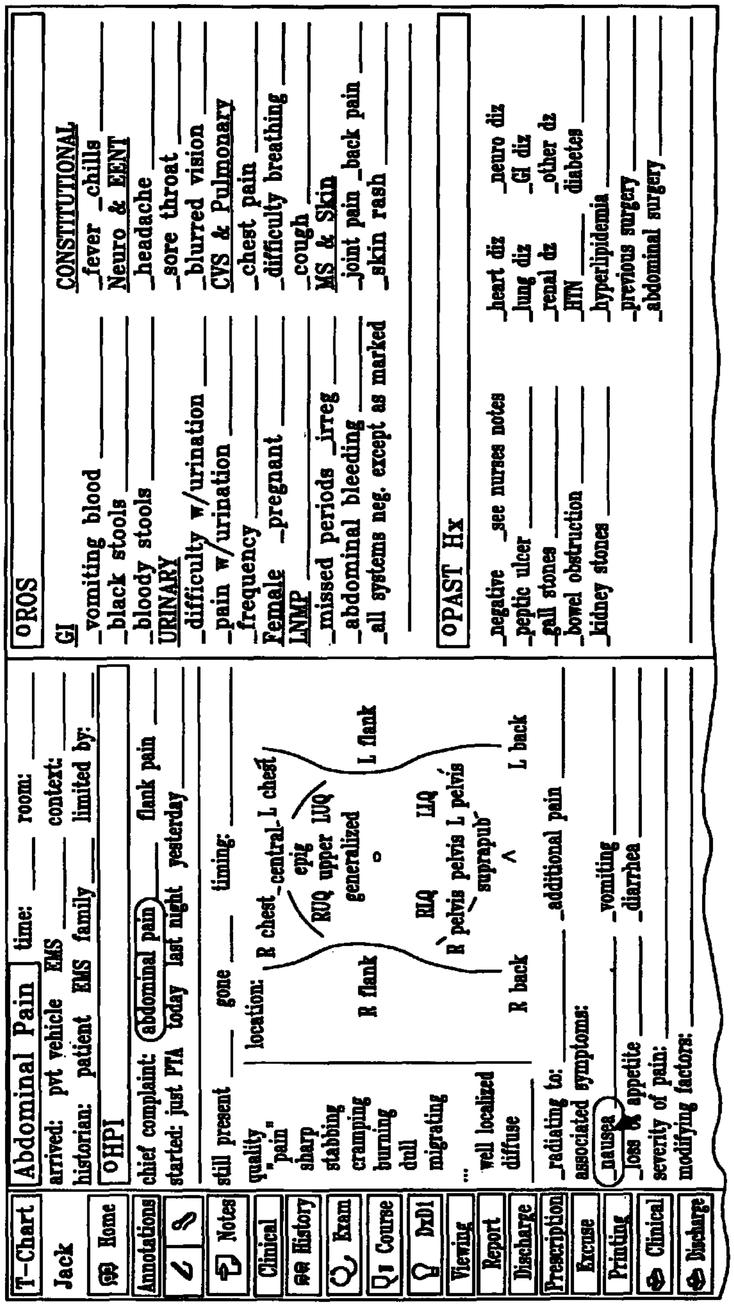

FIG. 12

| T-Chart | Abdominal Pain | time: ___ room: ___ | ○ROS |
|---|---|---|---|
| Jack | arrived: pvt vehicle EMS | context: ___ | |
| | historian: patient EMS family | limited by: ___ | |

○HPI
chief complaint: (abdominal pain) ___ flank pain
started: just PTA today last night yesterday
still present ___ gone ___ timing: ___
quality
"pain"
sharp
stabbing
cramping
burning
chill
migrating location: R chest _ central_L chest
         epig
         RUQ upper LUQ
         generalized
         R flank               L flank
         RLQ      LLQ
         R pelvis pelvis L pelvis
                suprapub
         R back     ∧    L back well localized ___ additional pain
diffuse
radiating to: ___
associated symptoms: ___ vomiting
                     ___ diarrhea
(nausea)
loss of appetite
severity of pain:
modifying factors:

Sidebar: Home, Annotations, Notes, Clinical, History, Exam, Course, DxDl, Viewing, Report, Discharge, Prescription, Excuse, Printing, Clinical, Discharge GI
_vomiting blood
_black stools
_bloody stools
URINARY
_difficulty w/urination
_pain w/urination
_frequency
Female _pregnant
LNMP
_missed periods _irreg
_abdominal bleeding
_all systems neg. except as marked CONSTITUTIONAL
_fever _chills
Neuro & EENT
_headache
_sore throat
_blurred vision
CVS & Pulmonary
_chest pain
_difficulty breathing
_cough
MS & Skin
_joint pain _back pain
_skin rash ○PAST Hx
_negative _see nurses notes
_peptic ulcer
_gall stones
_bowel obstruction
_kidney stones _heart dz   _neuro dz
_lung dz    _GI dz
_renal dz   _other dz
_HTN        _diabetes
_hyperlipidemia
_previous surgery
_abdominal surgery

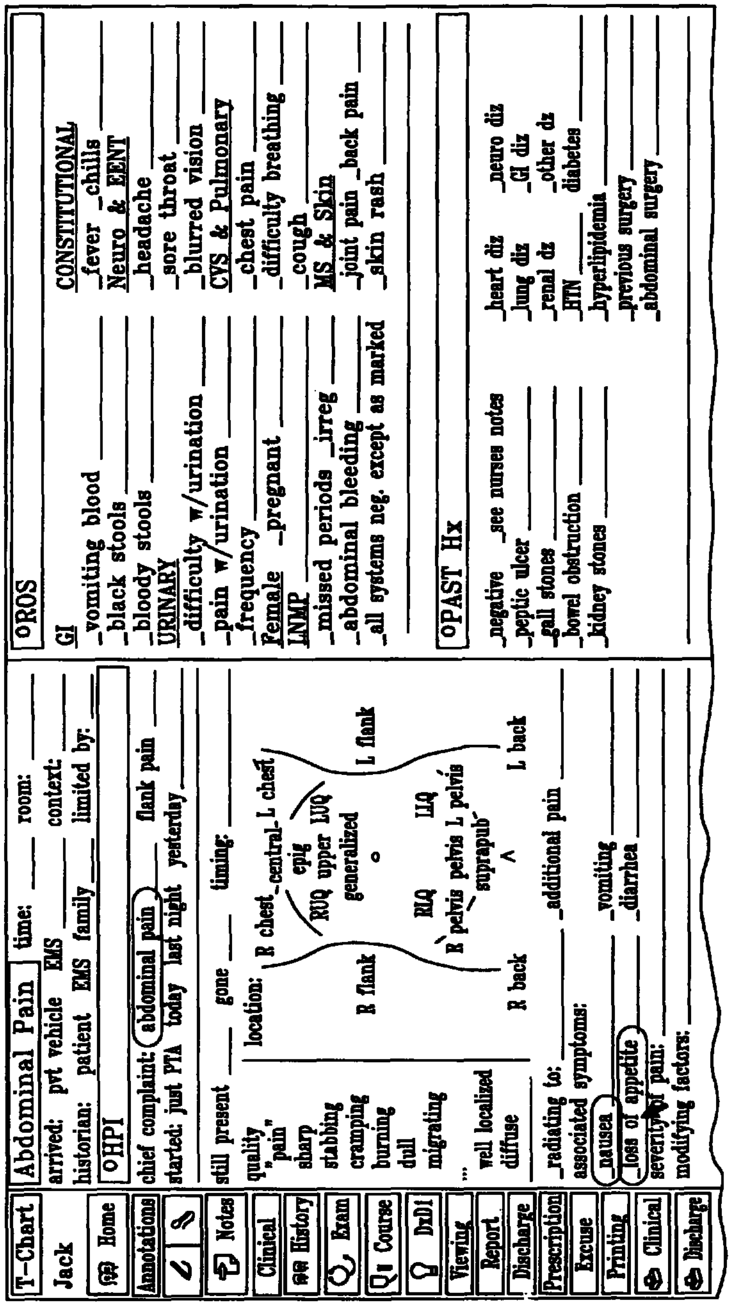

FIG. 13

| T-Chart | Abdominal Pain | time: | room: |
|---|---|---|---|
| Jack | arrived: prt vehicle EMS | context: | |
| | historian: patient EMS family | limited by: | |

🏠 Home

Annotations ✎ ✂

📝 Notes  ○HPI
chief complaint: (abdominal pain) ___ flank pain ___
started: just PTA today last night yesterday ___

Clinical
still present ___ gone ___ timing: ___

📖 History
quality,
"pain"
sharp
stabbing
cramping
burning
dull
migrating location:  R chest_central_L chest
                  epig
            RUQ upper LUQ              L flank
         R flank      generalized
                  RLQ      LLQ
              R pelvis pelvis L pelvis
                      suprapub
           R back                   L back 🔍 Exam 📋 Course
well localized ___ additional pain ___
diffuse ___

📄 D+D
radiating to: ___

Viewing
associated symptoms: ___ vomiting ___
                      ___ diarrhea ___

Report
(nausea) ___

Discharge
(loss of appetite) ___

Prescription
severity of pain: ___

Excuse
modifying factors: ___

Printing

⬅ Clinical

⬅ Discharge

○ROS

GI ___ vomiting blood ___
___ black stools ___
___ bloody stools ___
URINARY
___ difficulty w/urination ___
___ pain w/urination ___
___ frequency ___
Female ___ pregnant ___
LNMP ___
___ missed periods ___ irreg ___
___ abdominal bleeding ___
___ all systems neg. except as marked ___

CONSTITUTIONAL
___ fever ___ chills ___
Neuro & EENT
___ headache ___
___ sore throat ___
___ blurred vision ___
CVS & Pulmonary
___ chest pain ___
___ difficulty breathing ___
___ cough ___
MS & Skin
___ joint pain ___ back pain ___
___ skin rash ___

○PAST Hx
___ negative ___ see nurses notes ___
___ peptic ulcer ___
___ gall stones ___
___ bowel obstruction ___
___ kidney stones ___

___ heart dis ___ neuro dis ___
___ lung dis ___ GI dis ___
___ renal ds ___ other dx ___
___ HTN ___ diabetes ___
___ hyperlipidemia ___
___ previous surgery ___
___ abdominal surgery ___

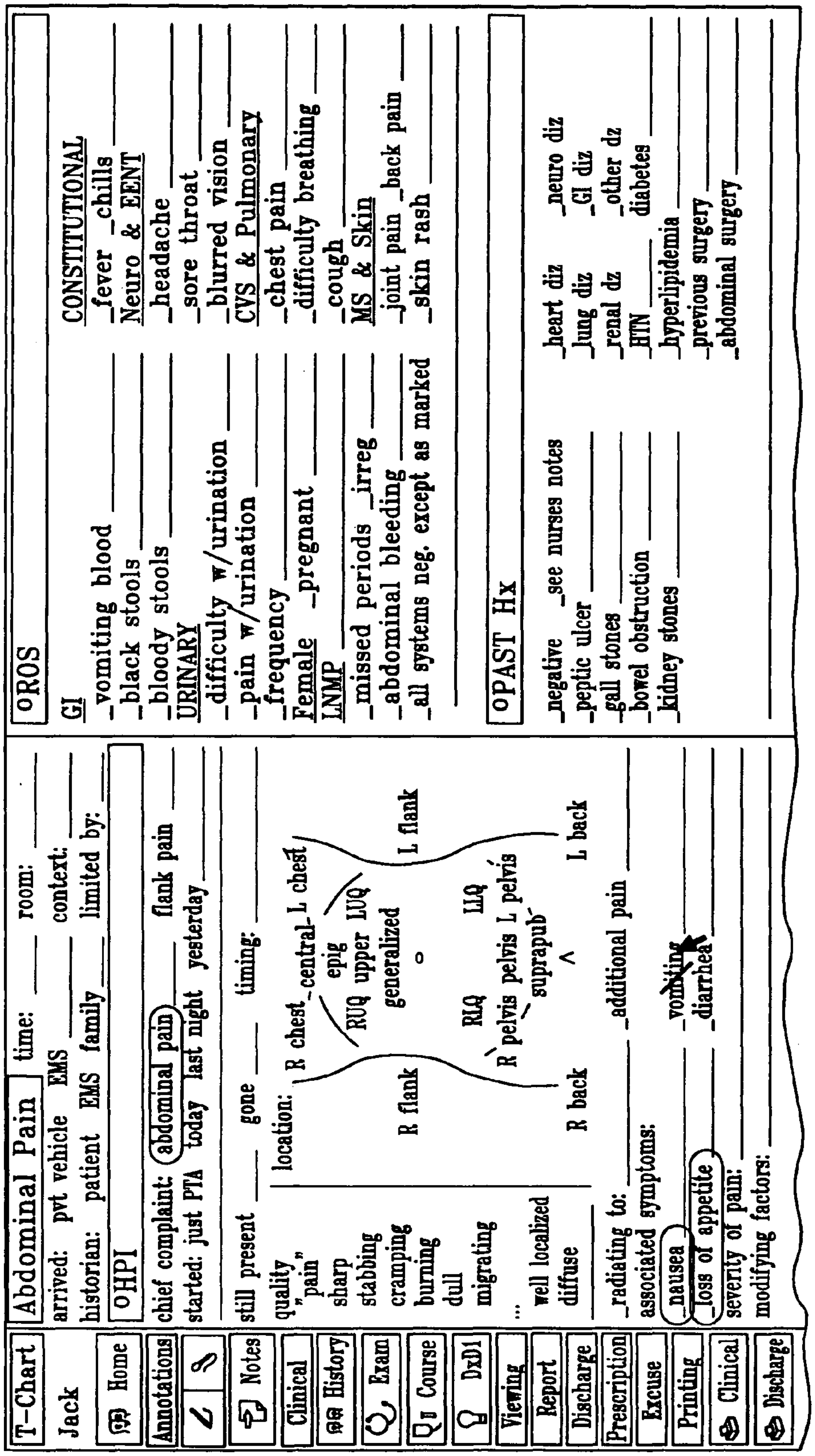

FIG. 14

T-Chart — Jack

| Abdominal Pain | time: ___ | room: ___ |
|---|---|---|
| arrived: pvt vehicle   EMS | | context: ___ |
| historian: patient   EMS   family | | limited by: ___ |

○HPI chief complaint: (abdominal pain) ___ flank pain ___
started: just PTA   today   last night   yesterday ___
still present ___ gone ___ timing: ___
quality
 "pain"    location:  R chest _ central _ L chest
 sharp                 epig
 stabbing         RUQ  upper  LUQ
 cramping    R flank   generalized   L flank
 burning               o
 dull                 RLQ     LLQ
 migrating       R pelvis  pelvis  L pelvis
well localized           suprapub
diffuse      R back ___ additional pain ___ L back
_radiating to: ___
associated symptoms: (nausea) _vomiting
 (loss of appetite) _diarrhea
severity of pain: ___
modifying factors: ___

○ROS

GI
 _vomiting blood ___
 _black stools ___
 _bloody stools ___
URINARY
 _difficulty w/urination ___
 _pain w/urination ___
 _frequency ___
 _Female   _pregnant ___
LNMP ___
 _missed periods   _irreg ___
 _abdominal bleeding ___
 _all systems neg. except as marked CONSTITUTIONAL
 _fever   _chills ___
Neuro & EENT
 _headache ___
 _sore throat ___
 _blurred vision ___
CVS & Pulmonary
 _chest pain ___
 _difficulty breathing ___
 _cough ___
MS & Skin
 _joint pain   _back pain ___
 _skin rash ___

○PAST Hx

_negative   _see nurses notes ___
_peptic ulcer ___
_gall stones ___
_bowel obstruction ___
_kidney stones ___

_heart dz   _neuro diz
_lung diz   _GI diz
_renal dz   _other dz
_HTN   _diabetes
_hyperlipidemia
_previous surgery
_abdominal surgery Sidebar: Home, Annotations, Notes, Clinical, History, Exam, Course, DxDl, Viewing, Report, Discharge, Prescription, Excuse, Printing, Clinical, Discharge

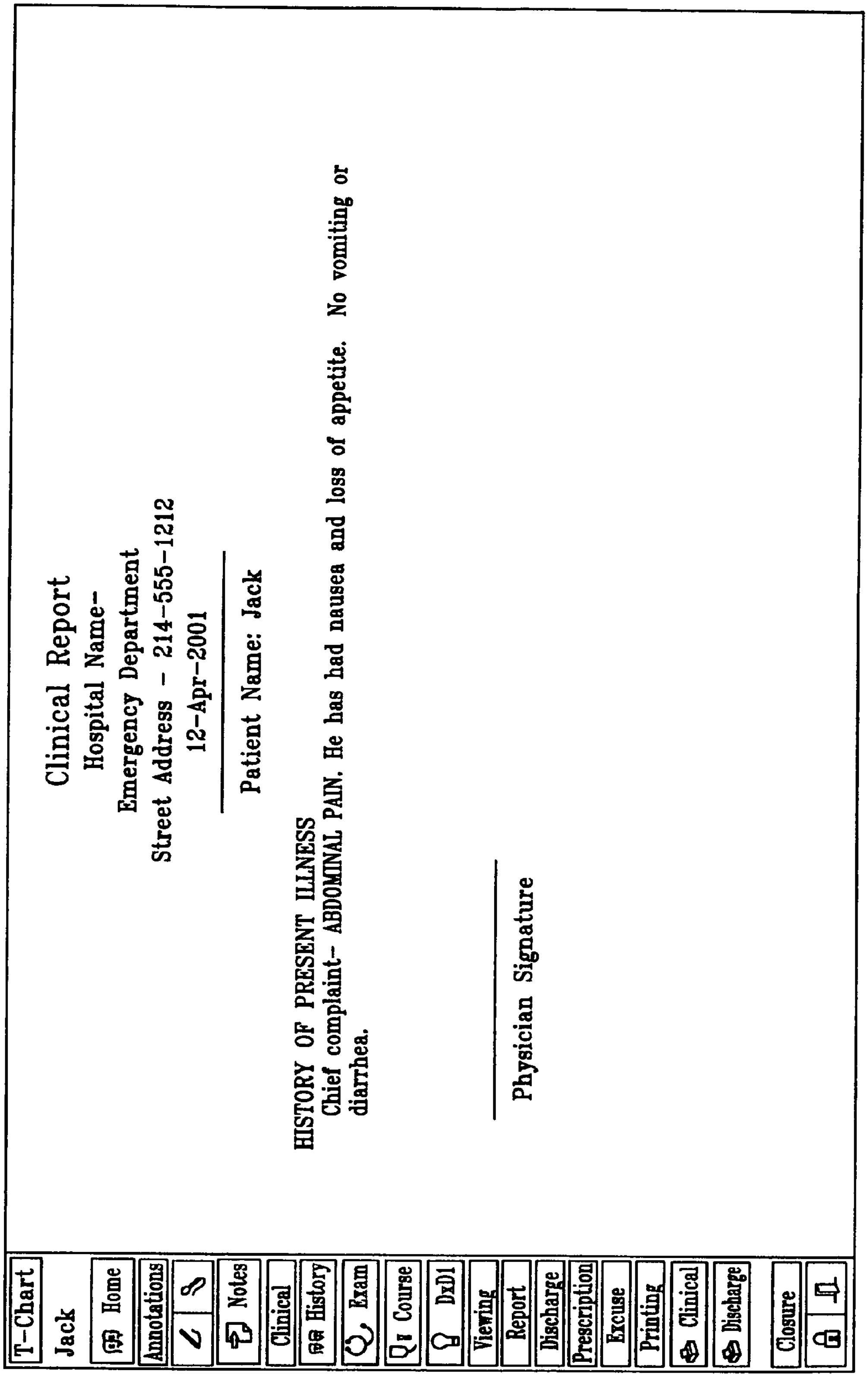

FIG. 16

Clinical Report
Hospital Name-
Emergency Department
Street Address - 214-555-1212
12-Apr-2001

Patient Name: Jack

HISTORY OF PRESENT ILLNESS
Chief complaint- ABDOMINAL PAIN. He has had nausea and loss of appetite. No vomiting or diarrhea.

_____
Physician Signature

T-Chart
Jack
Home
Annotations
Notes
Clinical
History
Exam
Course
DxDI
Viewing
Report
Discharge
Prescription
Excuse
Printing
Clinical
Discharge
Closure

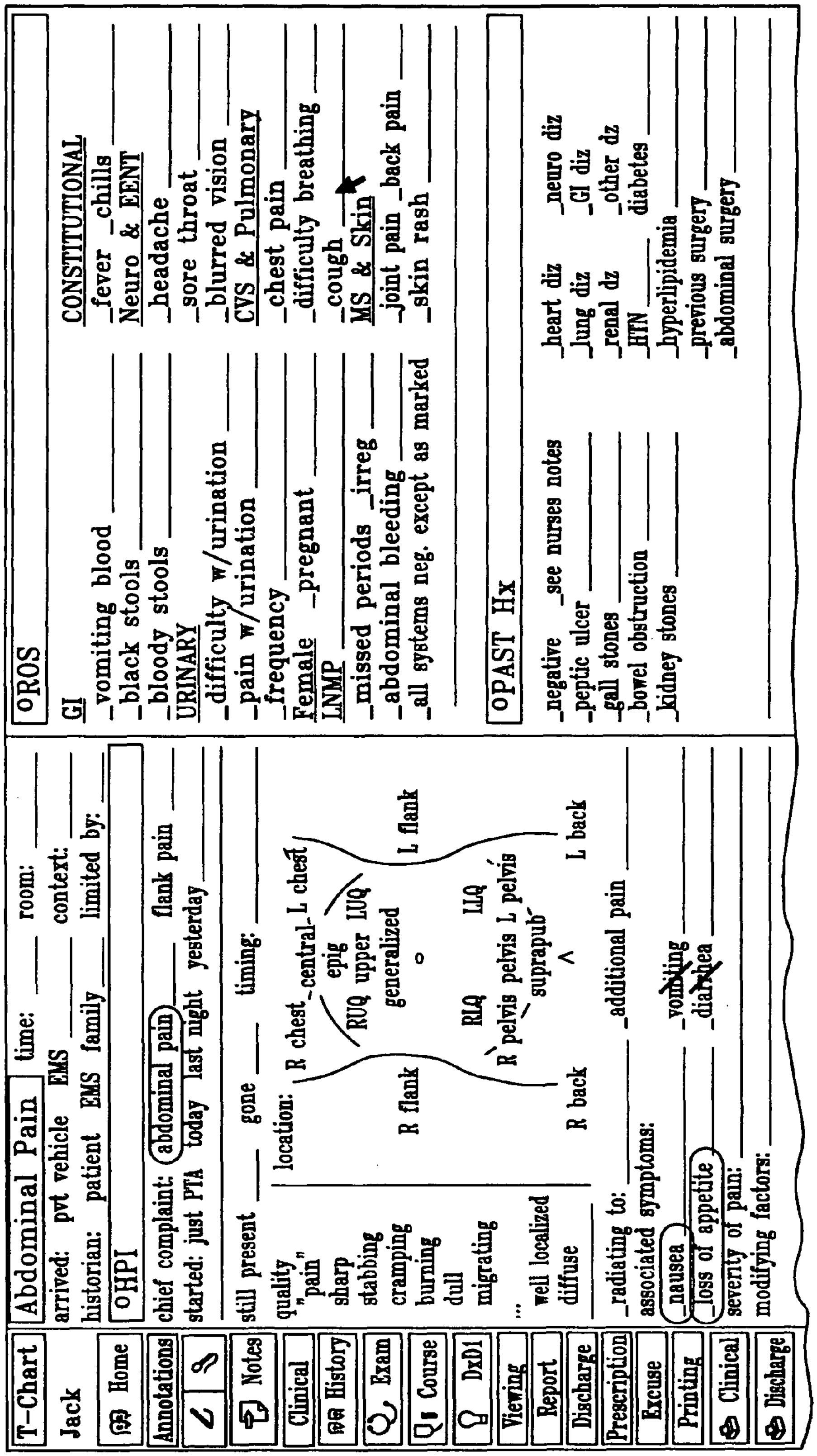

FIG. 17

T-Chart | Abdominal Pain    time: _____   room: _____
Jack      arrived: pvt vehicle   EMS _____   context: _____
          historian: patient  EMS  family _____  limited by: _____ oHPI
chief complaint: (abdominal pain) _____ flank pain _____
started: just PTA  today  last night  yesterday _____
still present _____ gone _____ timing: _____
quality         location:    R chest_central_L chest
"pain"                         epig
sharp                      RUQ upper LUQ              L flank
stabbing                        generalized
cramping            R flank                            L back
burning                       RLQ      LLQ
dull                      R  pelvis  pelvis L pelvis
migrating                         suprapub
                                     ^
well localized       R back _____ additional pain _____ L back
diffuse
radiating to: _____ _____ additional pain _____
associated symptoms:                vomi̶t̶i̶n̶g̶
(nausea)                            diar̶r̶h̶e̶a̶
(loss of appetite)
severity of pain: _____
modifying factors: _____ oROS
GI
_vomiting blood
_black stools
_bloody stools
URINARY
_difficulty w/urination
_pain w/urination
_frequency
Female _pregnant
LNMP
_missed periods _irreg
_abdominal bleeding
_all systems neg. except as marked CONSTITUTIONAL
_fever  _chills
Neuro & EENT
_headache
_sore throat
_blurred vision
CVS & Pulmonary
_chest pain
_difficulty breathing
_cough
MS & Skin      ←
_joint pain _back pain
_skin rash oPAST Hx
_negative  _see nurses notes       _heart diz   _neuro diz
_peptic ulcer                      _lung diz    _GI diz
_gall stones                       _renal dz    _other dz
_bowel obstruction                 HTN          diabetes
_kidney stones                     _hyperlipidemia
                                   _previous surgery
                                   _abdominal surgery Sidebar: Home, Annotations, Notes, Clinical, History, Exam, Course, DxDl, Viewing, Report, Discharge, Prescription, Excuse, Printing, Clinical, Discharge

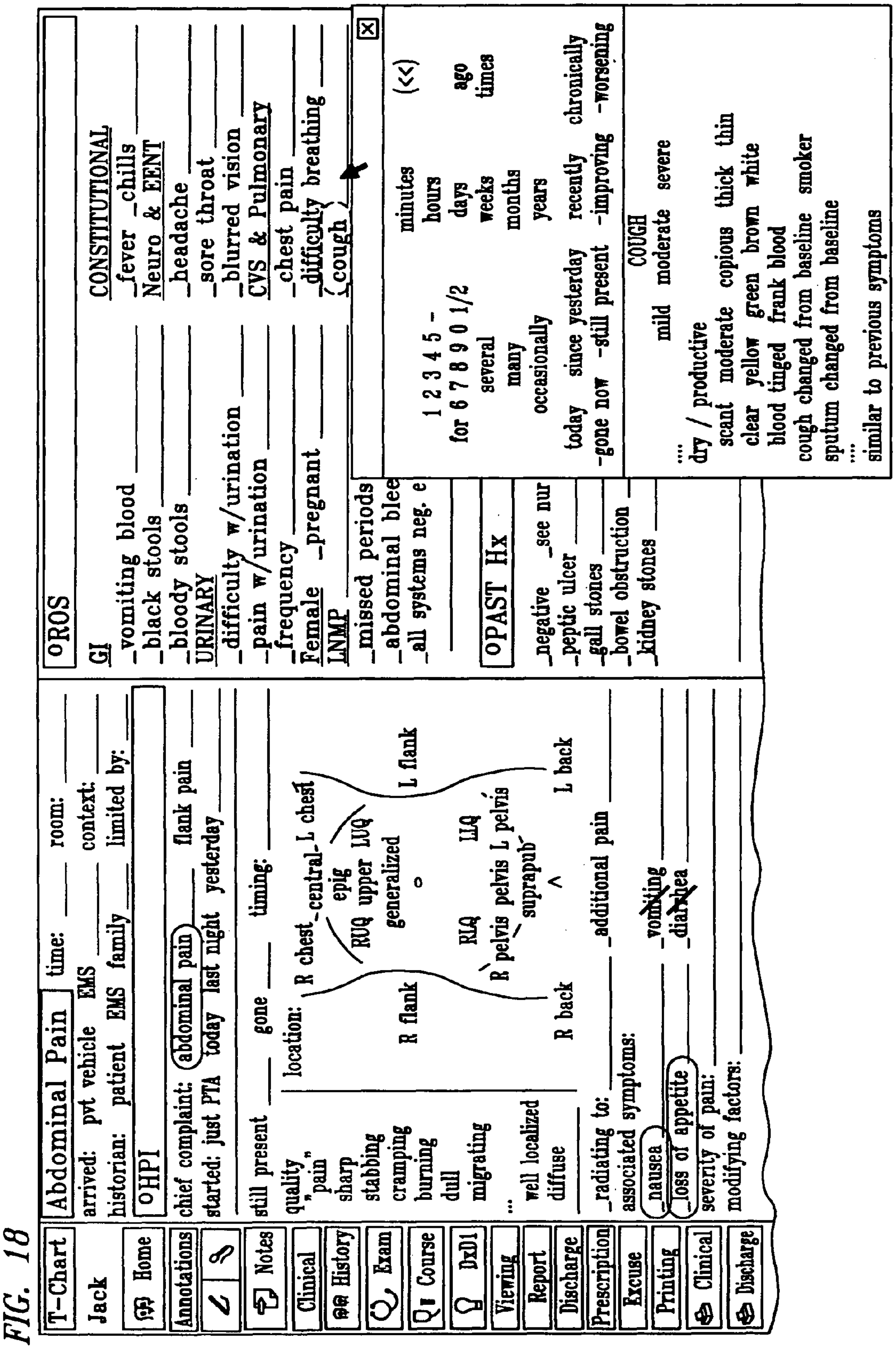

FIG. 18

T-Chart | Abdominal Pain | time: ___ room: ___
Jack
arrived: pvt vehicle EMS ___ context: ___
historian: patient EMS family ___ limited by: ___

OHPI
chief complaint: (abdominal pain) ___ flank pain ___
started: just PTA today last night yesterday ___ still present ___ gone ___ timing: ___
location: R chest  central  L chest
                    epig
              RUQ  upper  LUQ
                 generalized              L flank
R flank
              RLQ           LLQ
              R pelvis  pelvis  L pelvis
                     suprapub
R back                                      L back quality
"pain"
sharp
stabbing
cramping
burning
dull
migrating
well localized
diffuse
___ radiating to: ___ additional pain ___
associated symptoms:    vomiting
                        diarrhea
(nausea)
(loss of appetite)
severity of pain:
modifying factors:

oROS
GI
___ vomiting blood
___ black stools
___ bloody stools
URINARY
___ difficulty w/urination
___ pain w/urination
___ frequency
Female ___ pregnant
LNMP
___ missed periods
___ abdominal blee___
___ all systems neg. e___

OPAST Hx
___ negative ___ see nur___
___ peptic ulcer
___ gall stones
___ bowel obstruction
___ kidney stones CONSTITUTIONAL
___ fever ___ chills
Neuro & EENT
___ headache
___ sore throat
___ blurred vision
CVS & Pulmonary
___ chest pain
___ difficulty breathing
(cough) ←

☒
  1 2 3 4 5 —       minutes         (<<)
for 6 7 8 9 0 1/2   hours           ago
   several          days            times
   many             weeks
   occasionally     months
                    years
today  since yesterday  recently  chronically
-gone now  -still present  -improving  -worsening COUGH
      mild  moderate  severe
...
dry / productive
scant  moderate  copious  thick  thin
clear  yellow  green  brown  white
blood tinged  frank blood
cough changed from baseline  smoker
sputum changed from baseline
...
similar to previous symptoms Home
Annotations
Notes
Clinical
History
Exam
Course
DxDl
Viewing
Report
Discharge
Prescription
Excuse
Printing
Clinical
Discharge

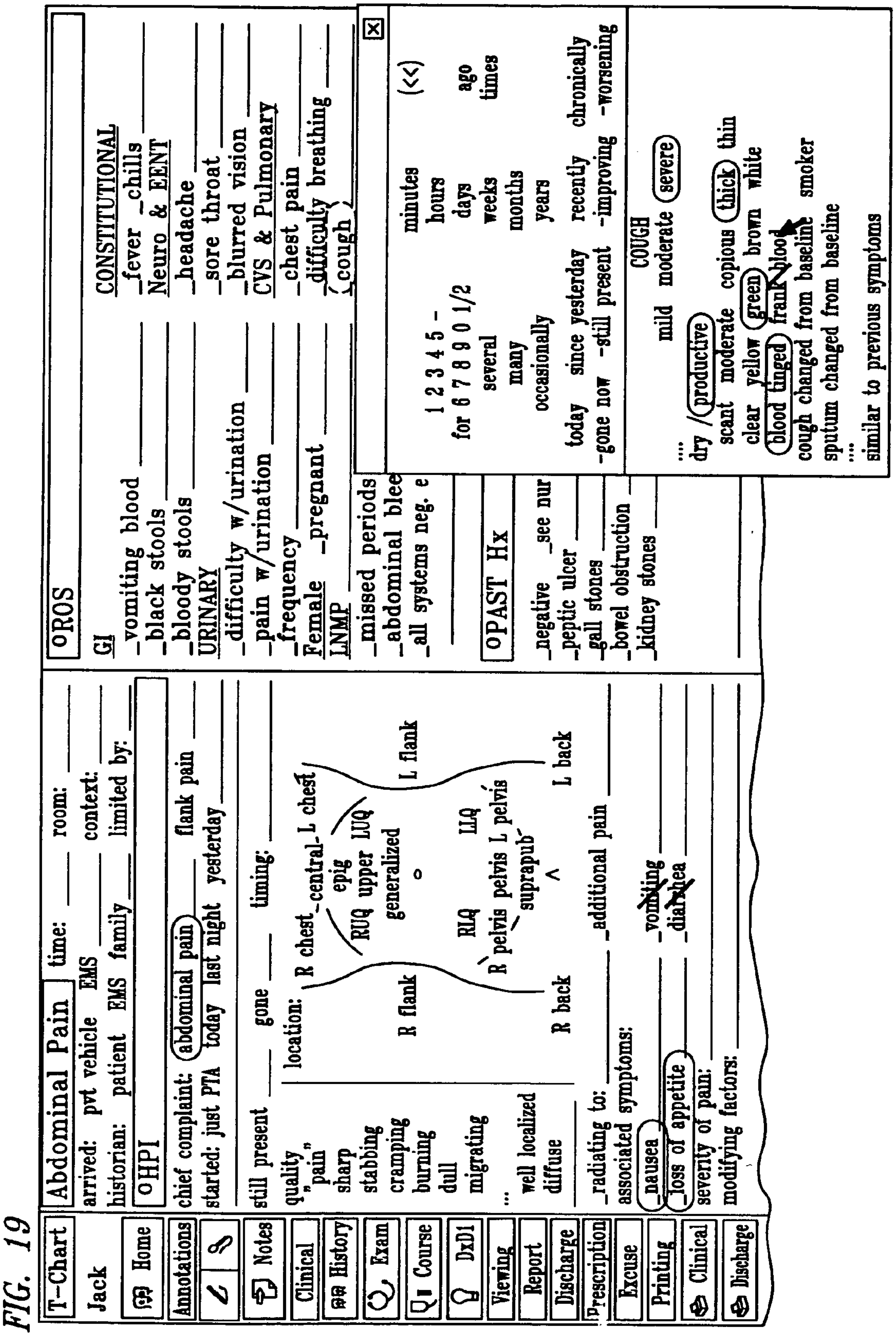

FIG. 19

| T-Chart | Abdominal Pain | time: ___ | room: ___ |
|---|---|---|---|

Jack
arrived: pvt vehicle   EMS              context: ___
historian: patient  EMS  family         limited by: ___

○HPI
chief complaint: (abdominal pain) ___ flank pain ___
started: just PTA  today  last night  yesterday ___
still present ___ gone ___ timing: ___
quality:
  "pain"          location:   R chest_central_L chest       L flank
  sharp                          epig
  stabbing                RUQ upper LUQ
  cramping                    generalized       o
  burning          R flank     RUQ         LLQ
  dull                        R pelvis pelvis L pelvis
  migrating                       suprapub
  ...                             ˅
  well localized   R back                        L back
  diffuse
  radiating to: ___           _additional pain___
associated symptoms:
  (nausea)                    vomiting
  (loss of appetite)          diarrhea
severity of pain: ___
modifying factors: ___

○ROS
GI
  _vomiting blood                    CONSTITUTIONAL
  _black stools                      _fever _chills
  _bloody stools                     Neuro & EENT
URINARY                              _headache
  _difficulty w/urination            _sore throat
  _pain w/urination                  _blurred vision
  _frequency                         CVS & Pulmonary
  Female _pregnant                   _chest pain
  LNMP ___                           _difficulty breathing
  _missed periods                    (cough)
  _abdominal blee
  _all systems neg. e ○PAST Hx                             ☒
  _negative _see nur                          (<<)
  _peptic ulcer         1 2 3 4 5 -        minutes       ago
  _gall stones          for 6 7 8 9 0 1/2  hours         times
  _bowel obstruction       several         days
  _kidney stones           many            weeks
                           occasionally    months
                                           years
                        today  since yesterday  recently  chronically
                        -gone now  -still present  -improving  -worsening COUGH
                           mild  moderate (severe)
                        .…
                        dry / (productive)
                        scant  moderate  copious  (thick) thin
                        clear  yellow  (green)  brown  white
                        (blood tinged)  frank-blood←  smoker
                        cough changed from baseline
                        sputum changed from baseline
                        ...
                        similar to previous symptoms Sidebar:
- Home
- Annotations
- Notes
- Clinical History
- Exam
- Course
- DxDl
- Viewing Report
- Discharge
- Prescription
- Excuse
- Printing
- Clinical
- Discharge

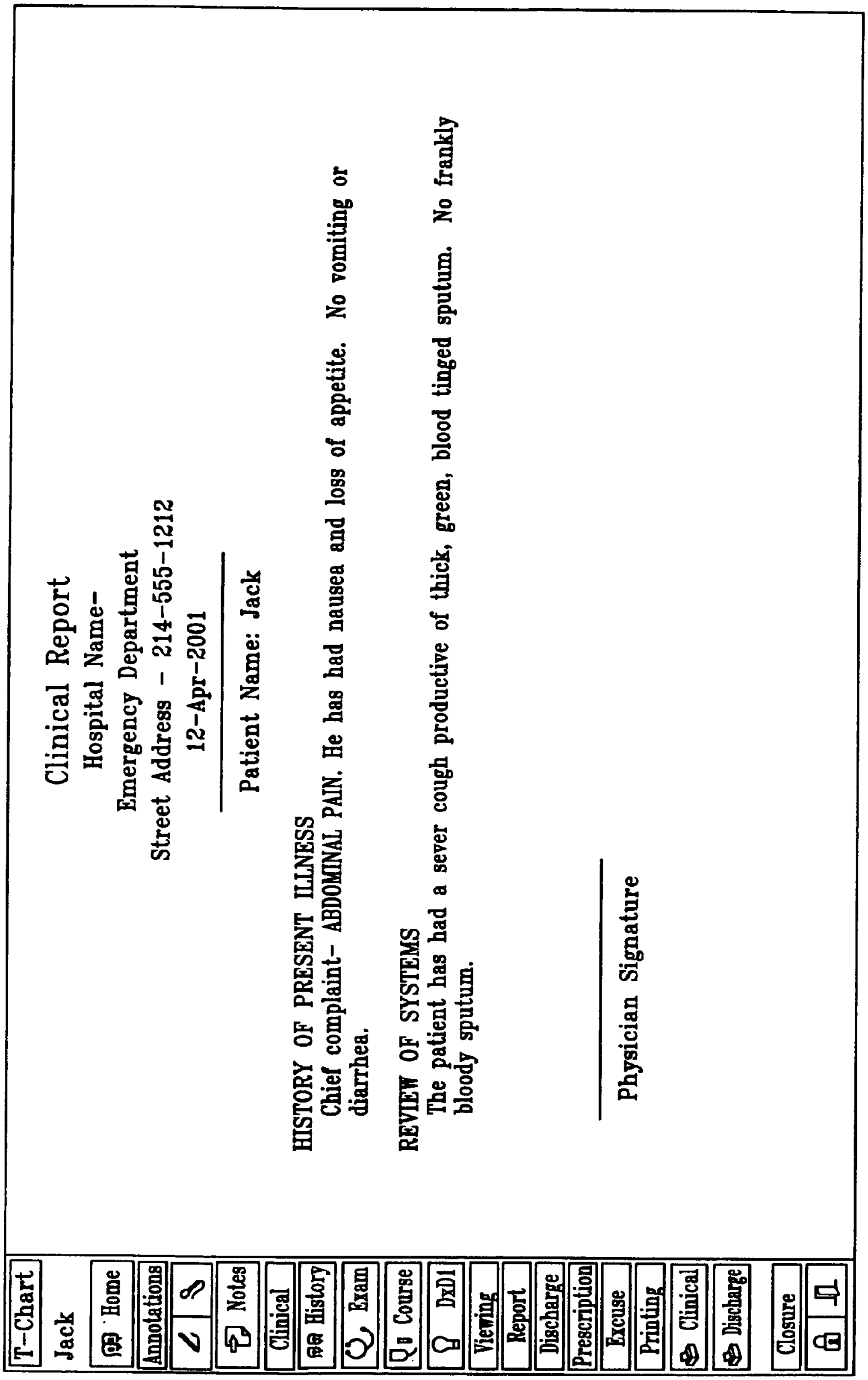

FIG. 20

Clinical Report
Hospital Name—
Emergency Department
Street Address — 214-555-1212
12-Apr-2001

Patient Name: Jack

HISTORY OF PRESENT ILLNESS
Chief complaint— ABDOMINAL PAIN. He has had nausea and loss of appetite. No vomiting or diarrhea.

REVIEW OF SYSTEMS
The patient has had a sever cough productive of thick, green, blood tinged sputum. No frankly bloody sputum.

_____
Physician Signature

- T-Chart Jack
- Home
- Annotations
- Notes
- Clinical
- History
- Exam
- Course
- DxDl
- Viewing
- Report
- Discharge
- Prescription
- Excuse
- Printing
- Clinical
- Discharge
- Closure

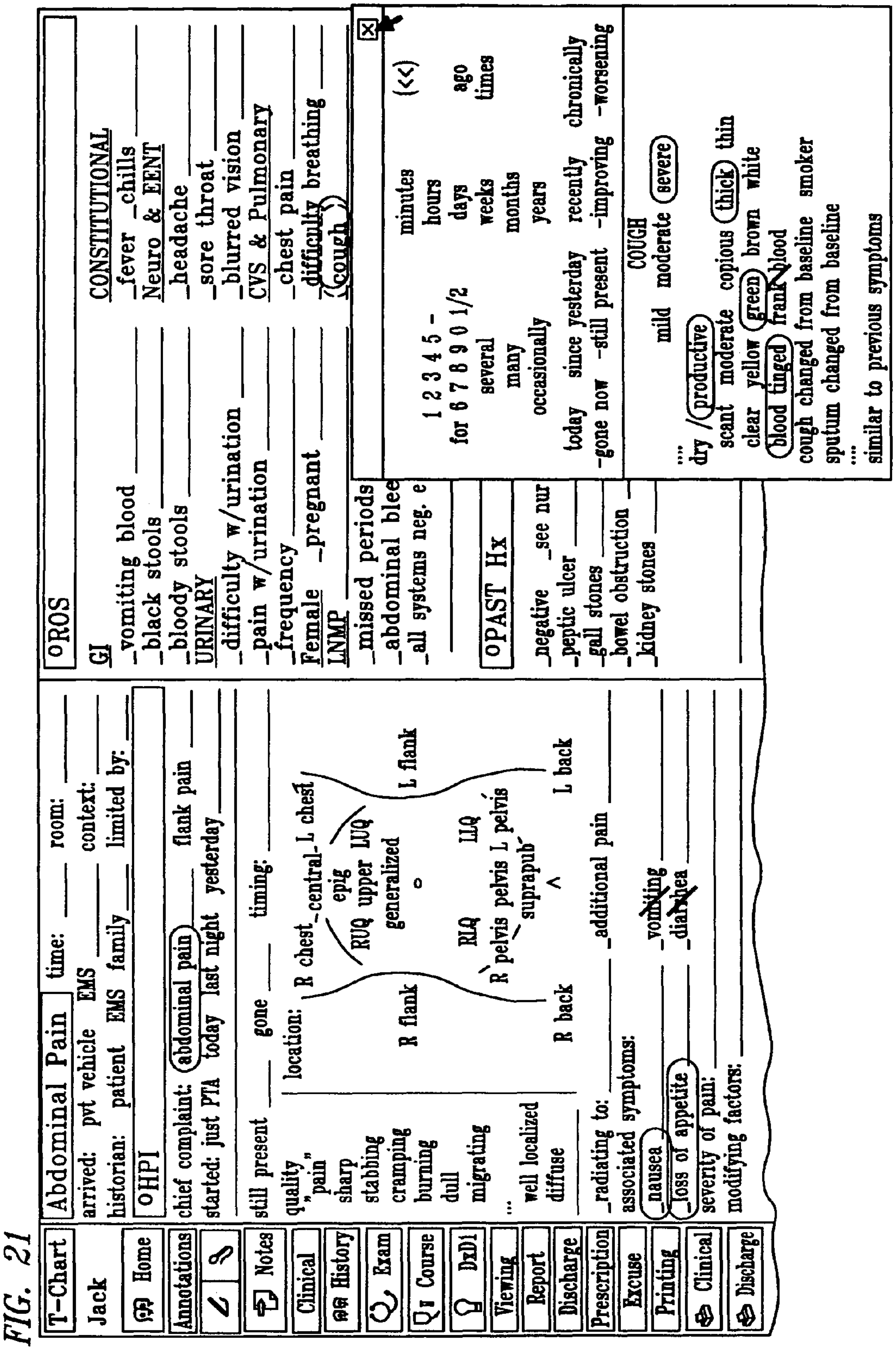

FIG. 21

T-Chart — Jack

| Home | Abdominal Pain | time: ___ room: ___ |
| Annotations | arrived: pvt vehicle EMS | context: ___ |
| | historian: patient EMS family | limited by: ___ |
| Notes | OHPI |
| Clinical History | chief complaint: (abdominal pain) ___ flank pain |
| | started: just PTA today last night yesterday |
| Exam | still present ___ gone ___ timing: ___ |
| Course | quality: location: R chest central L chest |
| DxDI | "pain" epig |
| | sharp RUQ upper LUQ |
| Viewing Report | stabbing generalized L flank |
| | cramping R flank |
| Discharge | burning RLQ LLQ |
| Prescription | dull R pelvis pelvis L pelvis |
| Excuse | migrating suprapub |
| Printing | ... R back L back |
| Clinical Discharge | well localized |
| | diffuse ___ additional pain |
| | radiating to: ___ |
| | associated symptoms: vomiting |
| | (nausea) diarrhea |
| | (loss of appetite) |
| | severity of pain: ___ |
| | modifying factors: ___ |

○ROS

GI
_ vomiting blood
_ black stools
_ bloody stools
URINARY
_ difficulty w/urination
_ pain w/urination
_ frequency
Female _ pregnant
LNMP
_ missed periods
_ abdominal bleed
_ all systems neg. e ○PAST Hx
_ negative _ see nur
_ peptic ulcer
_ gall stones
_ bowel obstruction
_ kidney stones CONSTITUTIONAL
_ fever _ chills
Neuro & EENT
_ headache
_ sore throat
_ blurred vision
CVS & Pulmonary
_ chest pain
_ difficulty breathing
(cough)

1 2 3 4 5 — minutes (<<)
for 6 7 8 9 0 1/2 hours ago
several days
many weeks times
occasionally months
 years
today since yesterday recently chronically
-gone now -still present -improving -worsening COUGH
mild moderate (severe)
dry / (productive)
scant moderate copious (thick) thin
clear yellow (green) brown white
(blood tinged) frank blood
cough changed from baseline smoker
sputum changed from baseline
...
similar to previous symptoms

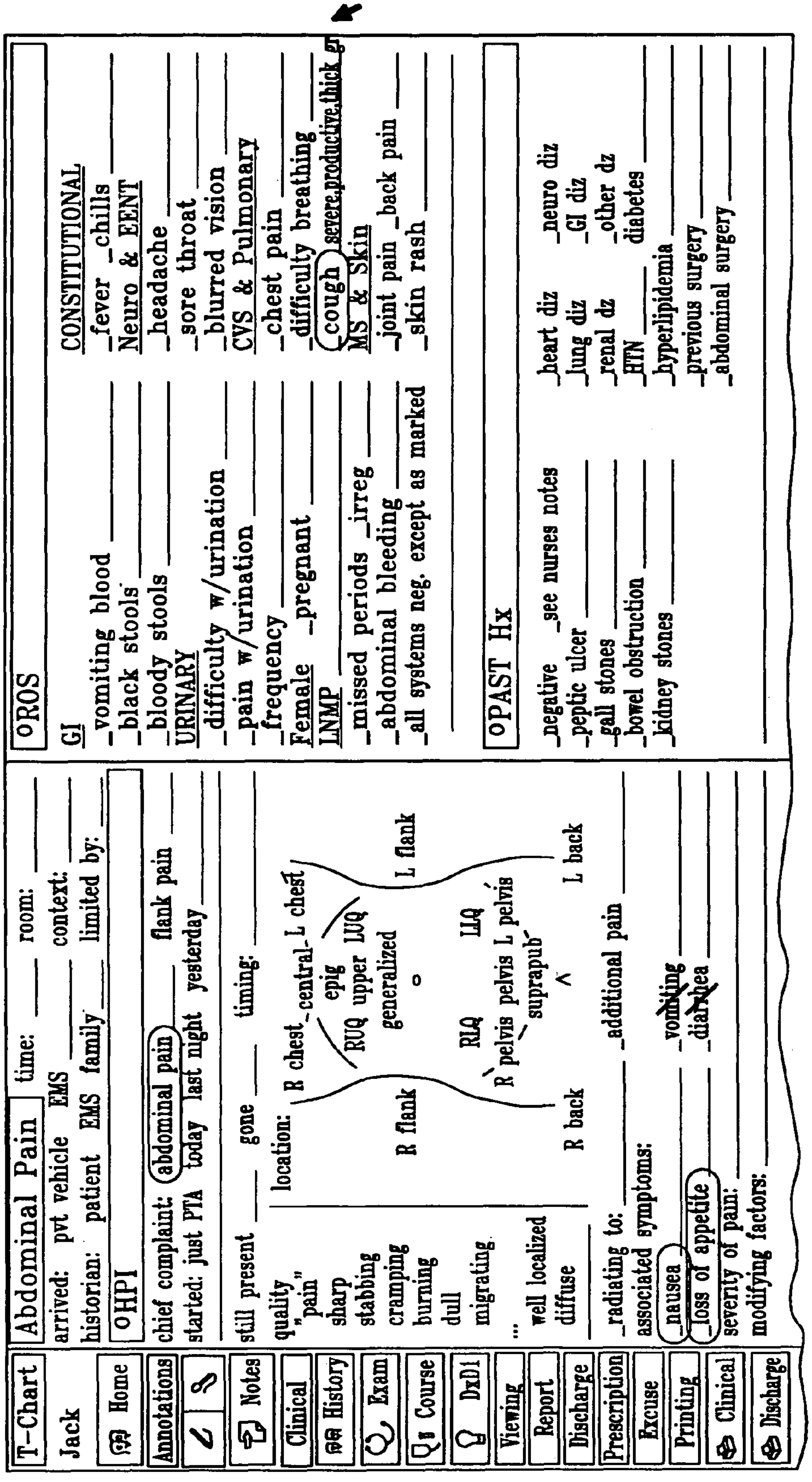

FIG. 22

| T-Chart | Abdominal Pain | time: | room: | |
|---|---|---|---|---|
| Jack | arrived: pvt vehicle EMS | | context: | |
| | historian: patient EMS family | | limited by: | |

oHPI chief complaint: (abdominal pain) _flank pain
started: just PTA today last night yesterday
_still present _gone _timing:
quality: location:
_"pain"
_sharp       R chest_central_L chest
_stabbing           epig     L flank
_cramping      RUQ upper LUQ
_burning         generalized
_dull            RLQ    LLQ
_migrating     R pelvis pelvis L pelvis
                   suprapub
_well localized
_diffuse    R flank               L back
            R back
_radiating to: _additional pain
associated symptoms:
_nausea _vomiting
_(loss of appetite) _diarrhea
severity of pain:
modifying factors:

oROS

GI
_vomiting blood
_black stools
_bloody stools
URINARY
_difficulty w/urination
_pain w/urination
_frequency
Female _pregnant
LNMP
_missed periods _irreg
_abdominal bleeding
_all systems neg. except as marked CONSTITUTIONAL
_fever _chills
Neuro & EENT
_headache
_sore throat
_blurred vision
CVS & Pulmonary
_chest pain
_difficulty breathing
_(cough) _severe,productive,thick
MS & Skin
_joint pain _back pain
_skin rash oPAST Hx

_negative _see nurses notes
_peptic ulcer
_gall stones
_bowel obstruction
_kidney stones _heart diz _neuro diz
_lung diz _GI diz
_renal dz _other dz
_HTN _diabetes
_hyperlipidemia
_previous surgery
_abdominal surgery Home
Annotations
Notes
Clinical
History
Exam
Course
DxDl
Viewing
Report
Discharge
Prescription
Excuse
Printing
Clinical
Discharge

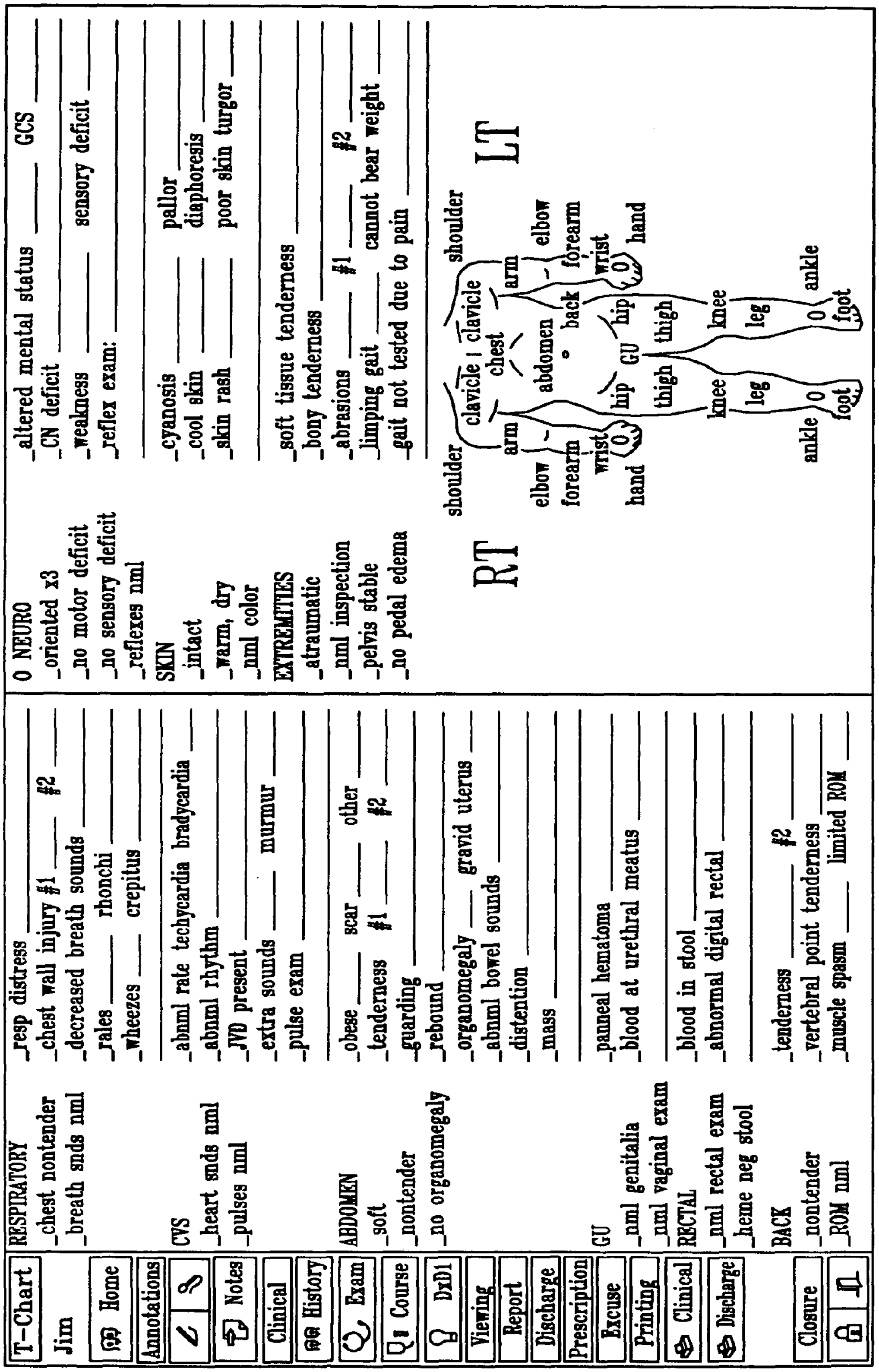

FIG. 24

| T-Chart | RESPIRATORY | _resp distress _____ #2 _____ | O NEURO |
| Jim | _chest nontender | _chest wall injury #1 _____ | _oriented x3 | _altered mental status _____ GCS _____ |
| | _breath snds nml | _decreased breath sounds _____ | _no motor deficit | _CN deficit _____ |
| 🏠 Home | | _rales _____ rhonchi _____ | _no sensory deficit | _weakness _____ sensory deficit _____ |
| Annotations | | _wheezes _____ crepitus _____ | _reflexes nml | _reflex exam: |
| ✏ ✏ | CVS | _abnml rate techycardia bradycardia _____ | SKIN | |
| | _heart snds nml | _abnml rhythm _____ | _intact | _cyanosis _____ pallor _____ |
| 📝 Notes | _pulses nml | _JVD present _____ | _warm, dry | _cool skin _____ diaphoresis _____ |
| Clinical | | _extra sounds _____ murmur _____ | _nml color | _skin rash _____ poor skin turgor _____ |
| 📖 History | | _pulse exam _____ | EXTREMITIES | |
| 🔍 Exam | ABDOMEN | _obese _____ scar _____ other _____ | _atraumatic | _soft tissue tenderness _____ |
| | _soft | _tenderness _____ #1 _____ #2 _____ | _nml inspection | _bony tenderness _____ |
| 📋 Course | _nontender | _guarding _____ | _pelvis stable | _abrasions _____ #1 _____ #2 _____ |
| 👤 DxDl | _no organomegaly | _rebound _____ | _no pedal edema | _limping gait _____ cannot bear weight _____ |
| Viewing | | _organomegaly _____ gravid uterus _____ | | _gait not tested due to pain _____ |
| Report | | _abnml bowel sounds _____ | | |
| Discharge | | _distention _____ | | |
| Prescription | | _mass _____ | | |
| Excuse | GU | _panneal hematoma _____ | | |
| Printing | _nml genitalia | _blood at urethral meatus _____ | | |
| 🩺 Clinical | _nml vaginal exam | | | |
| | RECTAL | _blood in stool _____ | | |
| 🚪 Discharge | _nml rectal exam | _abnormal digital rectal _____ | | |
| | _heme neg stool | | | |
| | BACK | _tenderness _____ #2 _____ | | |
| Closure | _nontender | _vertebral point tenderness _____ | | |
| 🔒 🔓 | _ROM nml | _muscle spasm _____ limited ROM _____ | | |

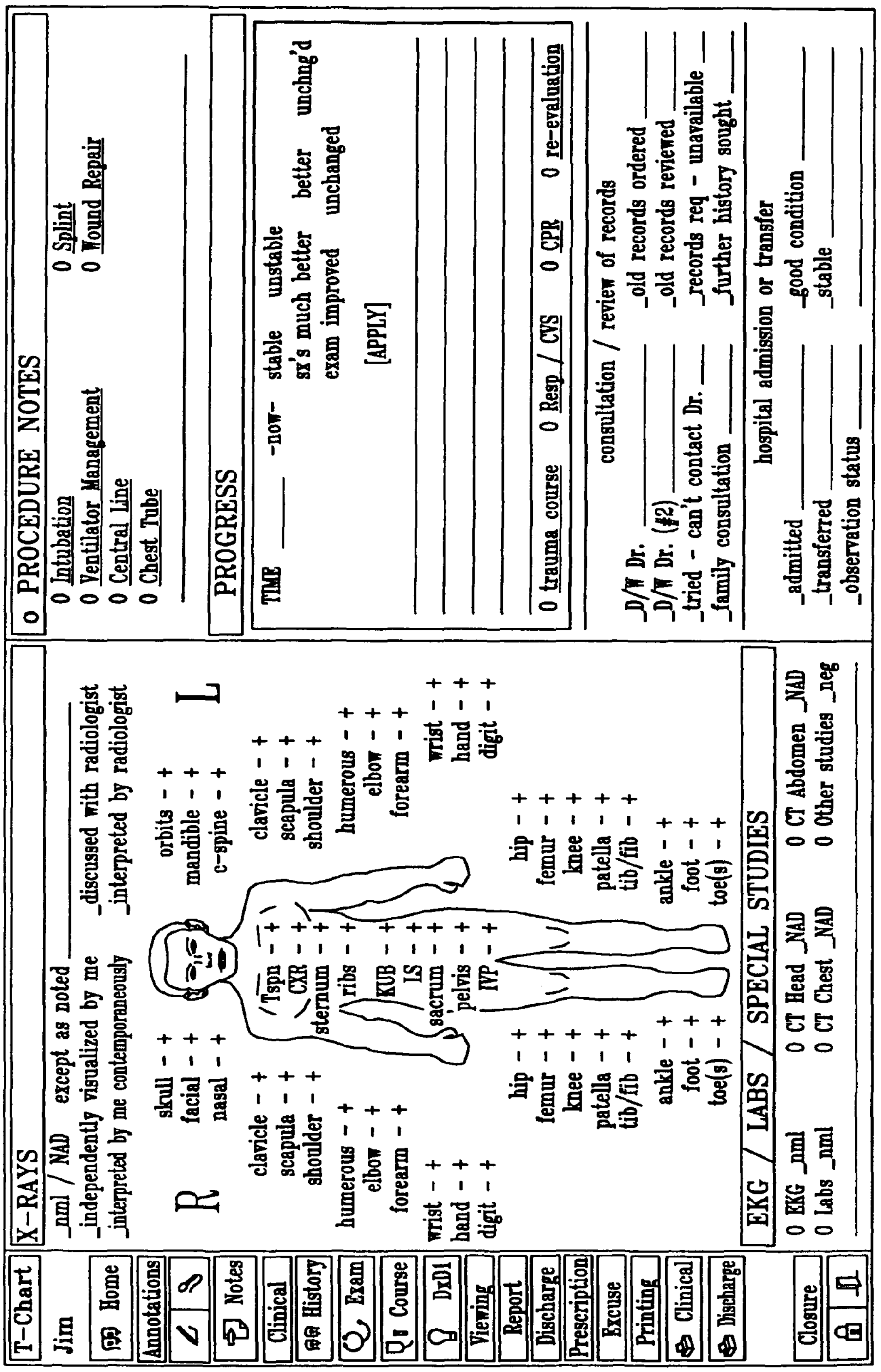

FIG. 25

T-Chart — Jim

X-RAYS
___ nml / NAD except as noted ___
___ independently visualized by me   ___ discussed with radiologist
___ interpreted by me contemporaneously   ___ interpreted by radiologist skull − +
facial − +
nasal − + orbits − +
mandible − +
c-spine − +

R   L clavicle − +
scapula − +
shoulder − +
humerous − +
elbow − +
forearm − +
wrist − +
hand − +
digit − +

Tspn − +
CXR − +
sternum − +
ribs − +
KUB − +
LS − +
sacrum − +
pelvis − +
IVP − + clavicle − +
scapula − +
shoulder − +
humerous − +
elbow − +
forearm − +
wrist − +
hand − +
digit − + hip − +
femur − +
knee − +
patella − +
tib/fib − +
ankle − +
foot − +
toe(s) − + hip − +
femur − +
knee − +
patella − +
tib/fib − +
ankle − +
foot − +
toe(s) − +

EKG / LABS / SPECIAL STUDIES
o EKG _nml_   o CT Head _NAD_   o CT Abdomen _NAD_
o Labs _nml_   o CT Chest _NAD_   o Other studies _neg_ o PROCEDURE NOTES
0 Intubation            0 Splint
0 Ventilator Management 0 Wound Repair
0 Central Line
0 Chest Tube

PROGRESS
TIME ___ −now−  stable   unstable
              sx's much better  better  unchng'd
              exam improved  unchanged
              [APPLY]

_____
_____
_____
_____

0 trauma course   0 Resp / CVS   0 CPR   0 re-evaluation consultation / review of records
_D/W Dr. _____   ___ old records ordered
_D/W Dr. (#2) ___   ___ old records reviewed
_tried − can't contact Dr. ___   ___ records req − unavailable
_family consultation ___   ___ further history sought hospital admission or transfer
___ admitted   ___ good condition
___ transferred   ___ stable
___ observation status Sidebar tabs: Home, Annotations, Notes, Clinical, History, Exam, Course, DxDl, Viewing, Report, Discharge, Prescription, Excuse, Printing, Clinical, Discharge, Closure

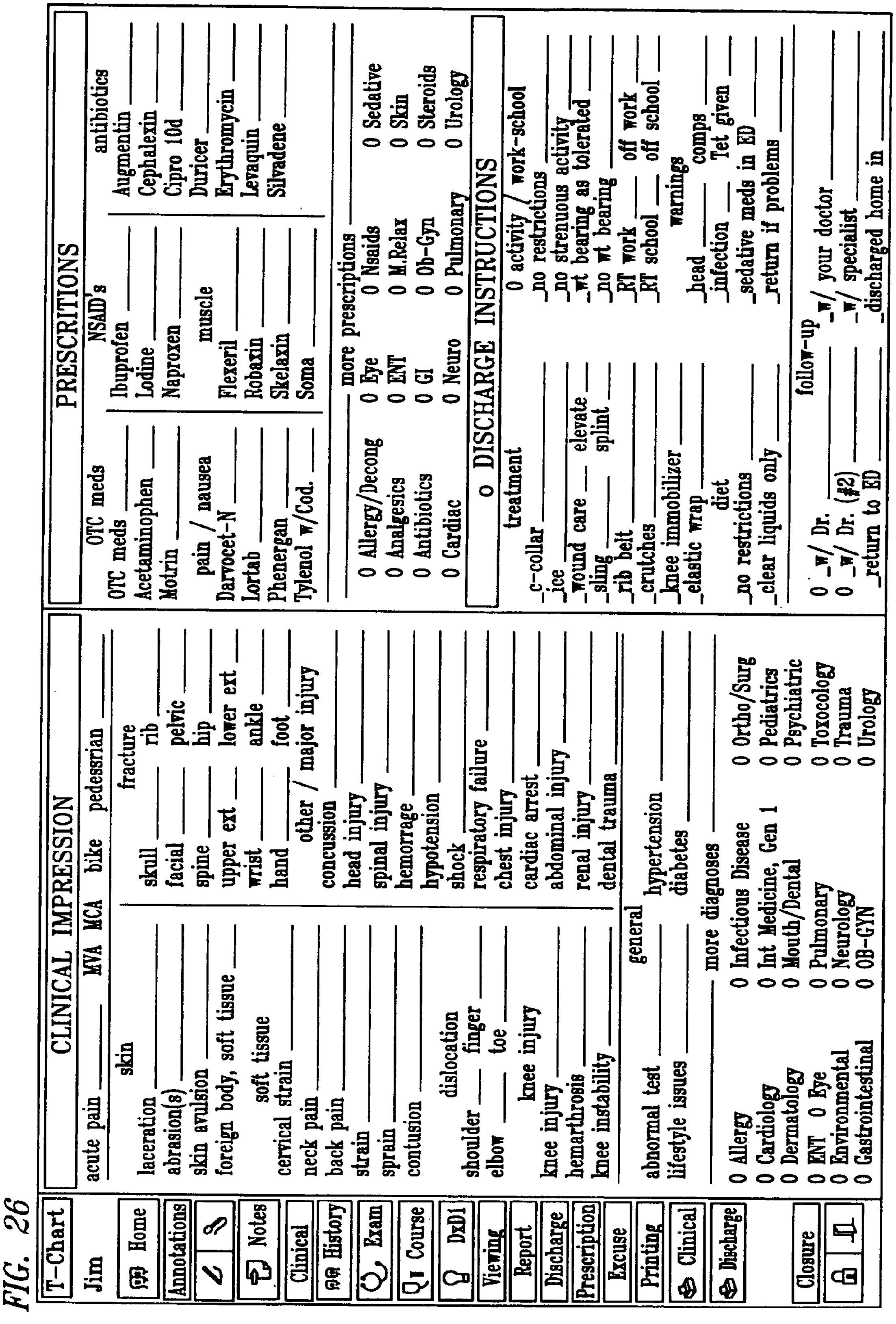

FIG. 26

| T-Chart | CLINICAL IMPRESSION | PRESCRIPTIONS |
|---|---|---|
| Jim | acute pain _____ MVA MCA bike pedestrian _____ | OTC meds _____ NSAID's _____ antibiotics _____ |
| Home | skin _____ fracture _____ | OTC meds _____ Ibuprofen _____ Augmentin _____ |
| Annotations | laceration _____ skull _____ rib _____ | Acetaminophen _____ Lodine _____ Cephalexin _____ |
|  | abrasion(s) _____ facial _____ pelvic _____ | Motrin _____ Naproxen _____ Cipro 10d _____ |
| Notes | skin avulsion _____ spine _____ hip _____ |  |  | Duricer _____ |
|  | foreign body, soft tissue _____ upper ext _____ lower ext _____ | pain / nausea _____ muscle _____ Erythromycin _____ |
| Clinical | soft tissue _____ wrist _____ ankle _____ | Darvocet-N _____ Flexeril _____ Levaquin _____ |
| History | cervical strain _____ hand _____ foot _____ | Lortab _____ Robaxin _____ Silvadene _____ |
|  | neck pain _____ other / major injury _____ | Phenergan _____ Skelaxin _____ |
| Exam | back pain _____ concussion _____ | Tylenol w/Cod. _____ Soma _____ |
|  | strain _____ head injury _____ |  |
| Course | sprain _____ spinal injury _____ | _____ more prescriptions _____ |
|  | contusion _____ hemorrhage _____ | 0 Allergy/Decong 0 Eye 0 Nsaids 0 Sedative |
| DxDl | hypotension _____ | 0 Analgesics 0 ENT 0 M.Relax 0 Skin |
|  | dislocation _____ shock _____ | 0 Antibiotics 0 GI 0 Ob-Gyn 0 Steroids |
| Viewing | shoulder _____ finger _____ toe _____ | 0 Cardiac 0 Neuro 0 Pulmonary 0 Urology |
|  | elbow _____ respiratory failure _____ |  |
| Report | knee injury _____ chest injury _____ | o DISCHARGE INSTRUCTIONS |
| Discharge | knee injury _____ cardiac arrest _____ | treatment _____ 0 activity / work-school _____ |
|  | hemarthrosis _____ abdominal injury _____ | c-collar _____ no restrictions _____ |
| Prescription | knee instability _____ renal injury _____ | ice _____ no strenuous activity _____ |
|  | dental trauma _____ | wound care _____ elevate _____ wt bearing as tolerated _____ |
| Excuse | abnormal test _____ general _____ hypertension _____ | sling _____ splint _____ no wt bearing _____ |
|  | lifestyle issues _____ diabetes _____ | rib belt _____ RT work _____ off work _____ |
| Printing |  |  | crutches _____ RT school _____ off school _____ |
|  | _____ more diagnoses _____ | knee immobilizer _____ warnings _____ |
| Clinical | 0 Allergy 0 Infectious Disease 0 Ortho/Surg | elastic wrap _____ head _____ comps _____ |
|  | 0 Cardiology 0 Int Medicine, Gen 1 0 Pediatrics | diet _____ infection _____ Tet given _____ |
| Discharge | 0 Dermatology 0 Mouth/Dental 0 Psychiatric | no restrictions _____ sedative meds in ED _____ |
|  | 0 ENT 0 Eye 0 Pulmonary 0 Toxocology | clear liquids only _____ return if problems _____ |
| Closure | 0 Environmental 0 Neurology 0 Trauma |  |
|  | 0 Gastrointestinal 0 OB-GYN 0 Urology | follow-up _____ |
|  |  | 0 _w/ Dr. _____ w/ your doctor _____ |
|  |  | 0 _w/ Dr. (#2) _____ w/ specialist _____ |
|  |  | return to ED _____ discharged home in _____ |

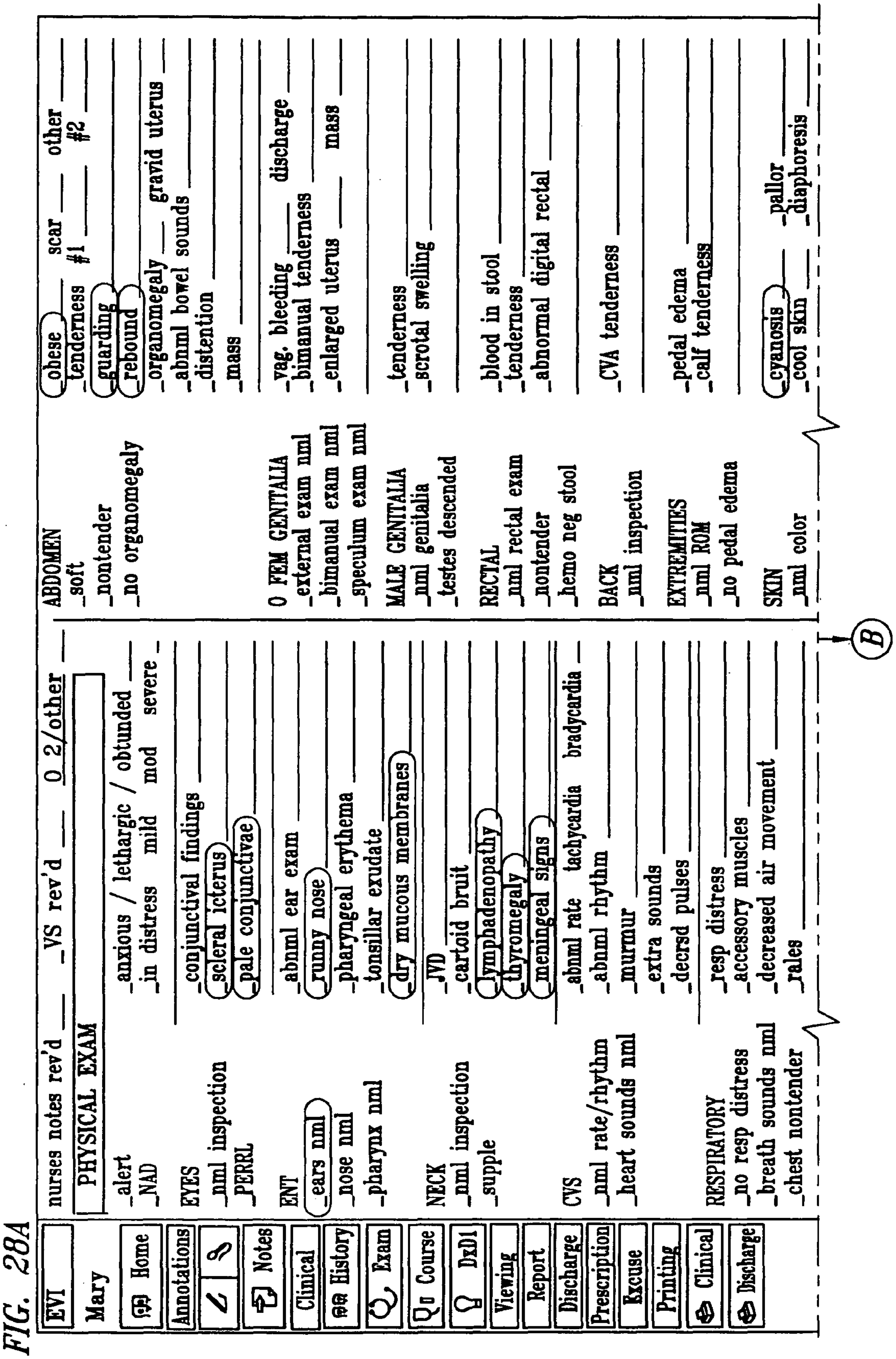

FIG. 28A

EVI | Mary

- Home
- Annotations
- Notes
- Clinical
- History
- Exam
- Qu Course
- DxDI
- Viewing
- Report
- Discharge
- Prescription
- Excuse
- Printing
- Clinical
- Discharge nurses notes rev'd ___ VS rev'd ___ O 2/other ___

PHYSICAL EXAM

_alert ___ _anxious / lethargic / obtunded ___
_NAD ___ _in distress  mild  mod  severe ___

EYES
_nml inspection ___ _conjunctival findings ___
_PERRL ___ _scleral icterus ___
_pale conjunctivae ___

ENT
(_ears nml_) _abnml ear exam ___
_nose nml ___ (_runny nose_) ___
_pharynx nml ___ _pharyngeal erythema ___
_tonsillar exudate ___
(_dry mucous membranes_) ___

NECK
_nml inspection ___ _JVD ___
_supple ___ _cartoid bruit ___
(_lymphadenopathy_) ___
(_thyromegaly_) ___
(_meningeal signs_) ___

CVS
_nml rate/rhythm ___ _abnml rate  tachycardia  bradycardia ___
_heart sounds nml ___ _abnml rhythm ___
_murmur ___
_extra sounds ___
_decrsd pulses ___

RESPIRATORY
_no resp distress ___ _resp distress ___
_breath sounds nml ___ _accessory muscles ___
_chest nontender ___ _decreased air movement ___
_rales ___

ABDOMEN
_soft ___ (_obese_) _scar ___ _other ___
_nontender ___ _tenderness  #1  #2 ___
_no organomegaly ___ (_guarding_) ___
(_rebound_) ___
_organomegaly  gravid uterus ___
_abnml bowel sounds ___
_distention ___
_mass ___

O FEM GENITALIA
_external exam nml ___ _vag. bleeding  discharge ___
_bimanual exam nml ___ _bimanual tenderness ___
_speculum exam nml ___ _enlarged uterus  mass ___

MALE GENITALIA
_nml genitalia ___ _tenderness ___
_testes descended ___ _scrotal swelling ___

RECTAL
_nml rectal exam ___ _blood in stool ___
_nontender ___ _tenderness ___
_hemo neg stool ___ _abnormal digital rectal ___

BACK
_nml inspection ___ _CVA tenderness ___

EXTREMITIES
_nml ROM ___ _pedal edema ___
_no pedal edema ___ _calf tenderness ___

SKIN
_nml color ___ (_cyanosis_) _pallor ___
_cool skin _diaphoresis ___

→ (B)

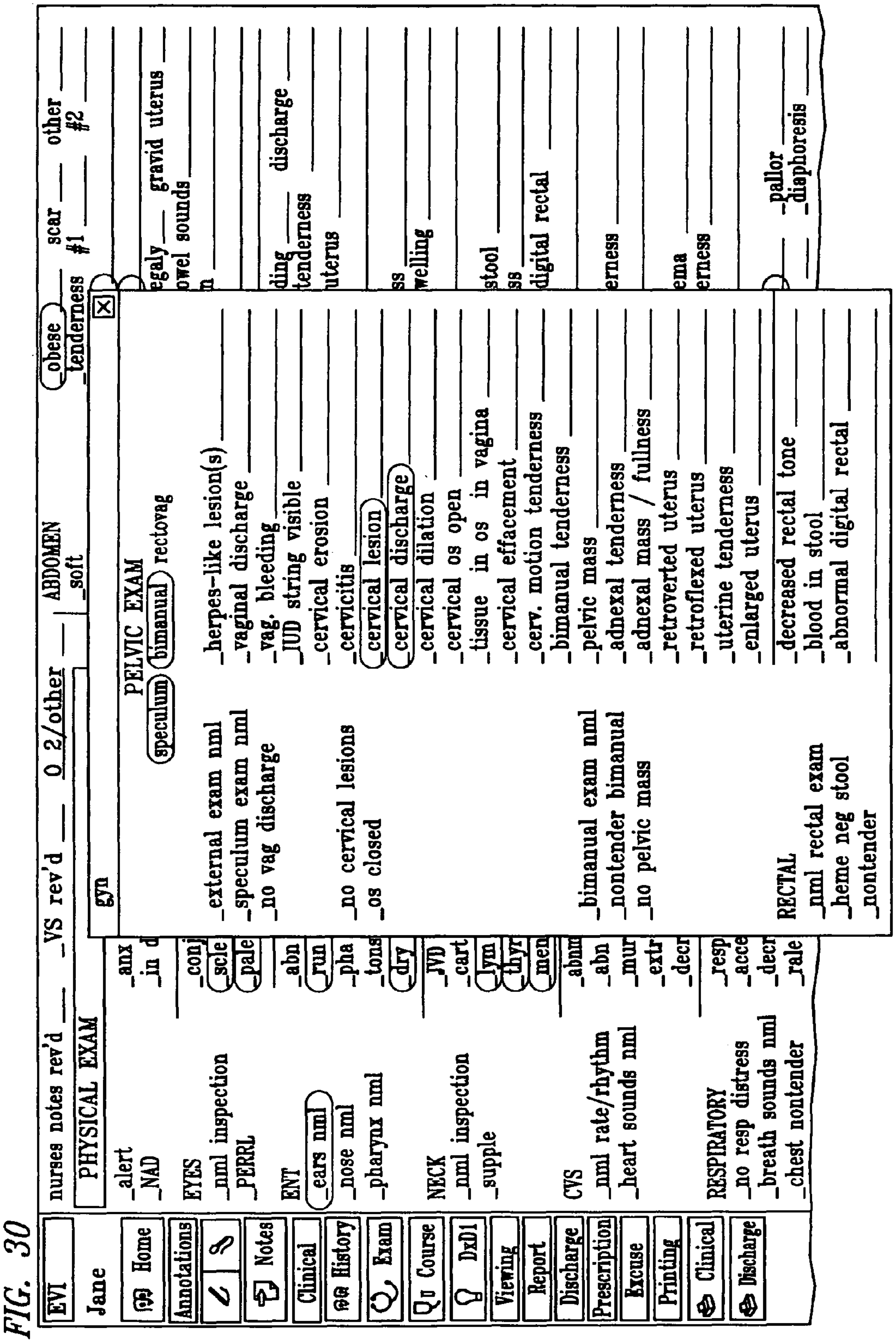

FIG. 30

[Sidebar buttons: Home, Annotations, Notes, Clinical, History, Exam, Course, DxDI, Viewing, Report, Discharge, Prescription, Excuse, Printing, Clinical, Discharge]

EVI  Jane    nurses notes rev'd ___  VS rev'd ___  O 2/other ___    ABDOMEN ___ scar ___ other ___
                                                                    (obese) ___ #1 ___ #2 ___
                                                                    tenderness  ⊠
PHYSICAL EXAM                                                       ___ soft _alert                    _anx                                                   _egaly ___ gravid uterus
_NAD                      _in d                                                  _owel sounds
EYES                      gyn                      PELVIC EXAM                   _n
_nml inspection           conj   (speculum) (bimanual) rectovag
_PERRL                    scle   _external exam nml    _herpes-like lesion(s)    _ding ___ discharge
                          pale   _speculum exam nml    _vaginal discharge        _tenderness
ENT                       _abn   _no vag discharge     _vag. bleeding            _uterus
_ears nml                 _run                         _IUD string visible
_nose nml                 _pha                         _cervical erosion
_pharynx nml              _tons  _no cervical lesions  _cervicitis               _ss
                          _dry   _os closed            (cervical lesion)         _welling
NECK                      _JVD                        (cervical discharge)
_nml inspection           _cart                        _cervical dilation        _stool
_supple                   _lym                         _cervical os open         _ss
                          _thyr                        _tissue in os in vagina   _digital rectal
                          _men                         _cervical effacement
CVS                       _abnm                        _cerv. motion tenderness
_nml rate/rhythm          _abn   _bimanual exam nml    _bimanual tenderness      _erness
_heart sounds nml         _mur   _nontender bimanual   _pelvic mass
                          _extr  _no pelvic mass       _adnexal tenderness       _ema
                          _decr                        _adnexal mass / fullness  _erness
RESPIRATORY               _resp                        _retroverted uterus
_no resp distress         _acce                        _retroflexed uterus
_breath sounds nml        _decr                        _uterine tenderness       _pallor
_chest nontender          _rale  RECTAL                _enlarged uterus          _diaphoresis
                                 _nml rectal exam      _decreased rectal tone
                                 _heme neg stool       _blood in stool
                                 _nontender            _abnormal digital rectal

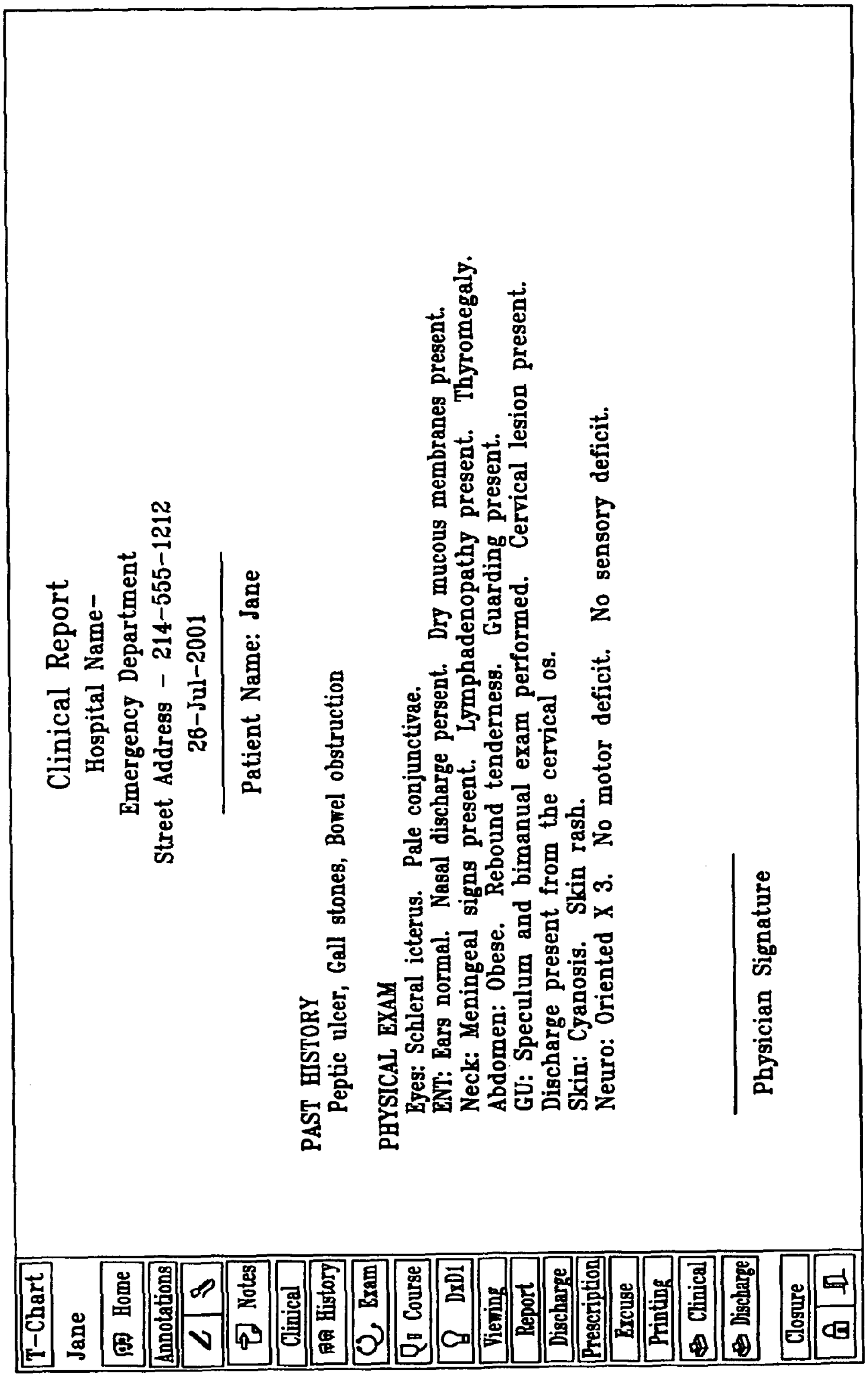

FIG. 31

Clinical Report
Hospital Name-
Emergency Department
Street Address - 214-555-1212
26-Jul-2001

Patient Name: Jane

PAST HISTORY
Peptic ulcer, Gall stones, Bowel obstruction

PHYSICAL EXAM
Eyes: Schleral icterus. Pale conjunctivae.
ENT: Ears normal. Nasal discharge persent. Dry mucous membranes present.
Neck: Meningeal signs present. Lymphadenopathy present. Thyromegaly.
Abdomen: Obese. Rebound tenderness. Guarding present.
GU: Speculum and bimanual exam performed. Cervical lesion present.
Discharge present from the cervical os.
Skin: Cyanosis. Skin rash.
Neuro: Oriented X 3. No motor deficit. No sensory deficit.

Physician Signature

T-Chart | Jane | Home | Annotations | Notes | Clinical History | Exam | Course | DxDI | Viewing Report | Discharge | Prescription | Excuse | Printing | Clinical | Discharge | Closure

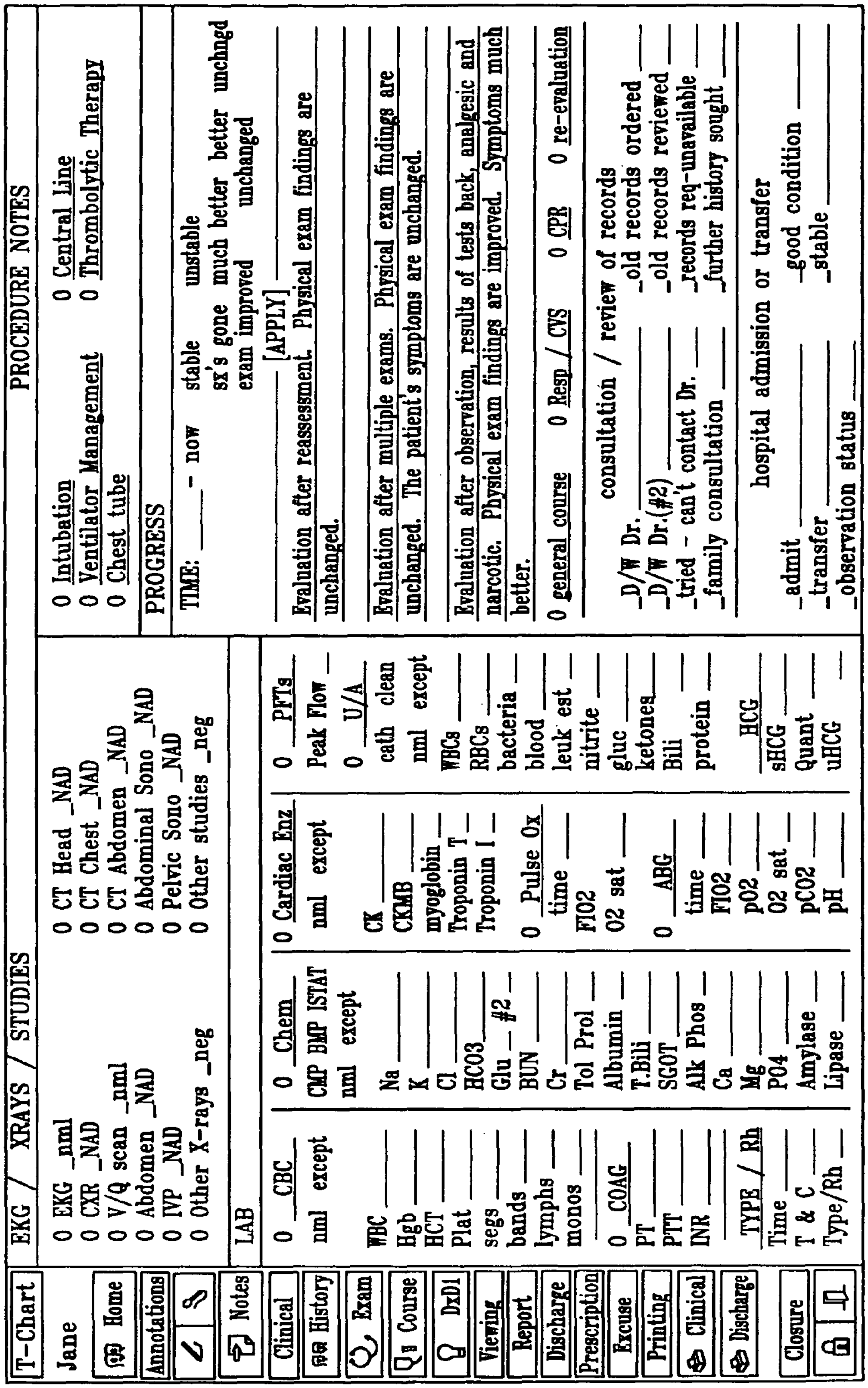

FIG. 33

| T-Chart | EKG / XRAYS / STUDIES | | | PROCEDURE NOTES | |
|---|---|---|---|---|---|
| Jane | 0 EKG _nml | | 0 CT Head _NAD | 0 Intubation | 0 Central Line |
| 🏠 Home | 0 CXR _NAD | | 0 CT Chest _NAD | 0 Ventilator Management | 0 Thrombolytic Therapy |
| | 0 V/Q scan _nml | | 0 CT Abdomen _NAD | 0 Chest tube | |
| Annotations | 0 Abdomen _NAD | | 0 Abdominal Sono _NAD | PROGRESS | |
| ✎ | 0 IVP _NAD | | 0 Pelvic Sono _NAD | TIME: ___ - now  stable  unstable | |
| 📝 Notes | 0 Other X-rays _neg | | 0 Other studies _neg | sx's gone much better better unchngd | |
| | LAB | | | exam improved  unchanged | |
| Clinical | 0 CBC | 0 Chem | 0 Cardiac Enz | 0 PFTs | [APPLY] |
| History | nml except | CMP BMP ISTAT | nml except | Peak Flow ___ | Evaluation after reassessment. Physical exam findings are |
| 🔍 Exam | | nml except | | 0 U/A | unchanged. |
| 📖 Course | WBC ___ | Na ___ | CK ___ | cath clean | Evaluation after multiple exams. Physical exam findings are |
| ? DxDl | Hgb ___ | K ___ | CKMB ___ | nml except | unchanged. The patient's symptoms are unchanged. |
| Viewing | HCT ___ | Cl ___ | myoglobin ___ | WBCs ___ | Evaluation after observation, results of tests back, analgesic and |
| Report | Plat ___ | HCO3 ___ | Troponin T ___ | RBCs ___ | narcotic. Physical exam findings are improved. Symptoms much |
| Discharge | segs ___ | Glu ___ #2 ___ | Troponin I ___ | bacteria ___ | better. |
| Prescription | bands ___ | BUN ___ | 0 Pulse Ox | blood ___ | 0 general course  0 Resp / CVS  0 CPR  0 re-evaluation |
| Excuse | lymphs ___ | Cr ___ | time ___ | leuk est ___ | consultation / review of records |
| Printing | monos ___ | Tol Prol ___ | FIO2 ___ | nitrite ___ | _D/W Dr. ___  _old records ordered |
| | 0 COAG | Albumin ___ | 02 sat ___ | gluc ___ | _D/W Dr.(#2) ___  _old records reviewed |
| Clinical | PT ___ | T.Bili ___ | 0 ABG | ketones ___ | _tried - can't contact Dr. ___  _records req-unavailable |
| Discharge | PTT ___ | SGOT ___ | time ___ | Bili ___ | _family consultation ___  _further history sought |
| | INR ___ | Alk Phos ___ | FIO2 ___ | protein ___ | hospital admission or transfer |
| Closure | TYPE / Rh | Ca ___ | pO2 ___ | | _admit ___  _good condition |
| 🔒 🚪 | Time ___ | Mg ___ | 02 sat ___ | _HCG ___ | _transfer ___  _stable |
| | T & C ___ | PO4 ___ | pCO2 ___ | sHCG ___ | _observation status ___ |
| | Type/Rh ___ | Amylase ___ | pH ___ | Quant ___ | |
| | | Lipase ___ | | uHCG ___ | |

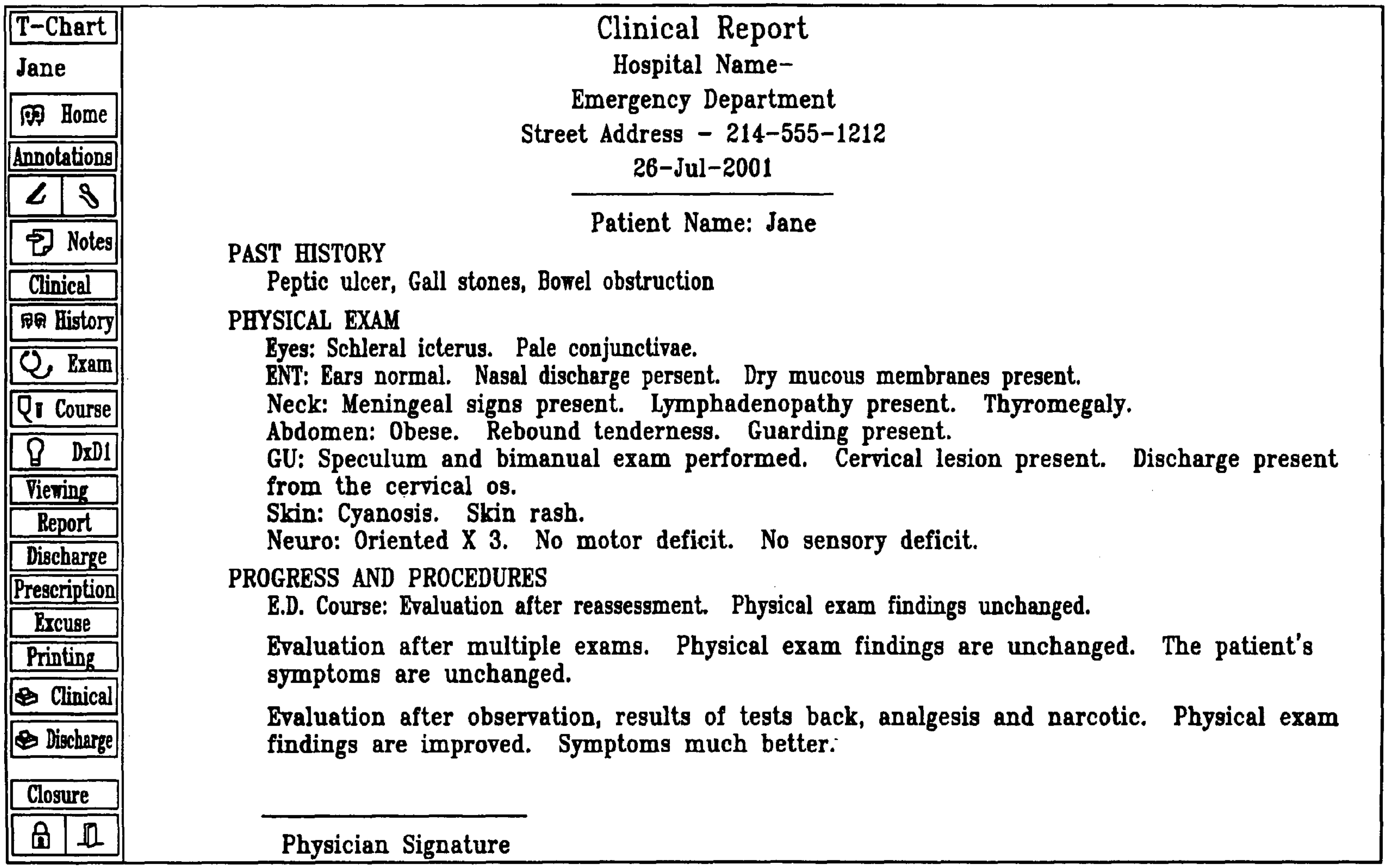

FIG. 34

Clinical Report
Hospital Name—
Emergency Department
Street Address — 214-555-1212
26-Jul-2001

Patient Name: Jane

PAST HISTORY
Peptic ulcer, Gall stones, Bowel obstruction

PHYSICAL EXAM
Eyes: Schleral icterus. Pale conjunctivae.
ENT: Ears normal. Nasal discharge persent. Dry mucous membranes present.
Neck: Meningeal signs present. Lymphadenopathy present. Thyromegaly.
Abdomen: Obese. Rebound tenderness. Guarding present.
GU: Speculum and bimanual exam performed. Cervical lesion present. Discharge present from the cervical os.
Skin: Cyanosis. Skin rash.
Neuro: Oriented X 3. No motor deficit. No sensory deficit.

PROGRESS AND PROCEDURES
E.D. Course: Evaluation after reassessment. Physical exam findings unchanged.

Evaluation after multiple exams. Physical exam findings are unchanged. The patient's symptoms are unchanged.

Evaluation after observation, results of tests back, analgesia and narcotic. Physical exam findings are improved. Symptoms much better.

_____
Physician Signature

Sidebar: T-Chart | Jane | Home | Annotations | Notes | Clinical | History | Exam | Course | DxDl | Viewing | Report | Discharge | Prescription | Excuse | Printing | Clinical | Discharge | Closure the chest pain was described as dull
the chest pain was not relieved by nitroglycerin

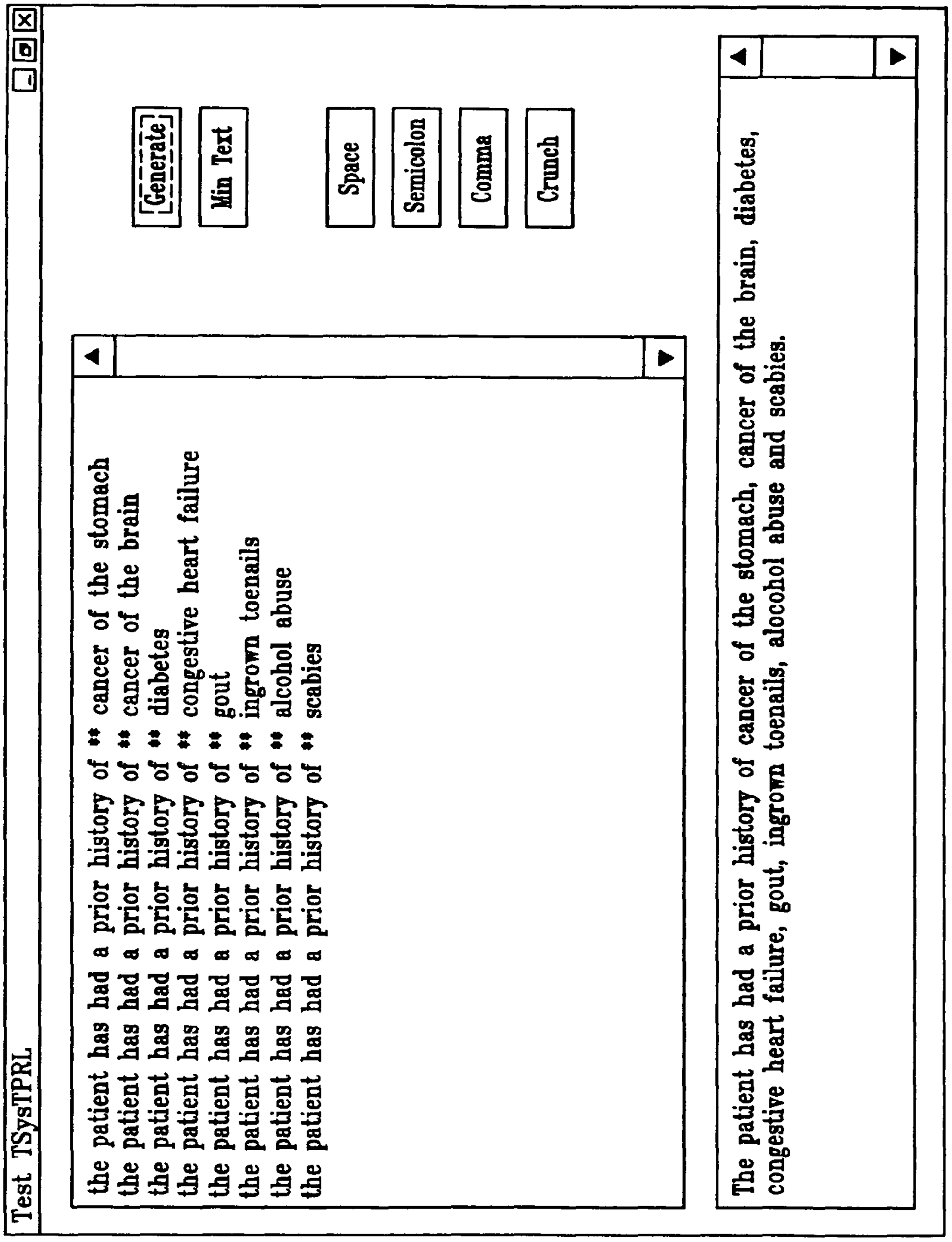

FIG. 37

Test TSysTPRL

[Generate] [Min Text] [Space] [Semicolon] [Comma] [Crunch]

the patient has had a prior history of ** cancer of the stomach
the patient has had a prior history of ** cancer of the brain
the patient has had a prior history of ** diabetes
the patient has had a prior history of ** congestive heart failure
the patient has had a prior history of ** gout
the patient has had a prior history of ** ingrown toenails
the patient has had a prior history of ** alcohol abuse
the patient has had a prior history of ** scabies The patient has had a prior history of cancer of the stomach, cancer of the brain, diabetes, congestive heart failure, gout, ingrown toenails, alocohol abuse and scabies.

METHOD FOR ENTERING, RECORDING, DISTRIBUTING AND REPORTING DATA

This application is a divisional of U.S. patent Ser. No. 09/927,972 filed on Aug. 10, 2001, which claims benefit of U.S. Provisional Application No. 60/309,452 filed on Aug. 1, 2001.

FIELD OF THE INVENTION

This invention relates to an improved method for efficiently and accurately entering detailed data by yes/no markings so that the data is automatically recorded, optionally automatically distributed and optionally transformed into a readable prose report of the data.

BACKGROUND OF THE INVENTION

Many computer systems have been proposed for entering data of a variety of types for a variety of purposes. Many of the systems rely upon relatively standardized yes/no entries but produce relatively non-informative reports. For instance, in FIG. 1 a prior art system is shown. Particularly when relatively detailed data is being taken and reported, the relatively simplified reporting system in FIG. 1 is wholly inadequate. Among the deficiencies in this type of data record is the fact that the recorder must expend a certain amount of effort to scan the yes/no columns for categories for marks and then correlate those to his findings. The recorders typically object to these seemly trivial efforts which are required to enter data on the form and it becomes clumsy and difficult to navigate when large numbers of entries must be organized and presented in such a fashion.

Accordingly, considerable effort has been directed to the development of improved systems for recording data especially in environments where considerable amounts of detailed data about a wide variety of subjects must be recorded and where the data must be recorded in some detail. One such instance is in medical emergency rooms where doctors are required to record data very quickly in order to provide a record for use by the hospital staff and to record their findings, proposed treatment, and the like with a minimum of effort. Similar situations exist in a number of other areas, but the requirements are particularly acute in hospital emergency room situations.

Previously, manual data entry systems have been used along with relatively simplistic forms such as shown in FIG. 1 on computers.

These systems have not been adequate to meet the requirements for detailed data recording.

Accordingly, an improved method has been sought which permits reporting of detailed amounts of data by yes/no entries by a physician or other recorder of information very efficiently.

SUMMARY OF THE INVENTION

According to the present invention, such data is effectively entered quickly and efficiently to produce at least one of a retrievable data base and a language text report of the entered data, by a system for entering data by yes/no entries and producing at least one of a retrievable data base and a language text report of the entered data. The system comprises: a workstation comprising a computer, including a screen capable of displaying a template form capable of receiving entries of yes/no data, capable of accessing a computer and programmed to permit access by an authorized user; a plurality of templates, each of the templates showing a plurality of relevant inquiries and capable of accepting data entry as yes/no entries by a user, said templates being accessible on the workstation or on a computer accessible by the workstation; a system access display programmed on the workstation or accessible by the workstation and providing the capability for a user to access a selected database or a selected template; a plurality of modifiers related to and associated with designated inquiries on at least a portion of the templates showing more detailed inquiries related to the inquiries on the templates for the entry of additional data; a retrievable database accessible by or on the workstation for storing and retrieving entered data from at least one of the templates and modifiers; and, a language program accessible by the workstation and capable of producing a language text report of the entered data.

The present invention further comprises a method for distributing copies of medical records the method comprising: entering medical records into a medical records database; entering a plurality of distribution options into a distribution database;

Selecting a distribution option from the distribution database; distributing medical records according to the selected distribution option; and, retaining in a database a record of the distribution of the medical records for retrieval as required.

The present invention further comprises a system for distributing copies of medical records, the system comprising: a database containing the medical records; a computer programmed to access the database and to distribute the medical records according to at least one selected distribution option via at least one communication means; and, a database programmed to retain a record of the medical records sent and the address to which the medical records were sent for retrieval upon request.

The present invention further comprises a method for generating easily readable English or other language text from simple sentences with each of the sentences reporting a single data entry and optionally containing modifiers of the data entry. The method comprises a method for generating easily readable English text from simple sentences, each of the sentences reporting a single data entry and optionally containing modifiers of one or more of the data entries comprising: selecting the words or phrases which correspond to the reported data entries; selecting which words or phrases can be combined into a single sentence and selecting the order of the selected words or phrases; limiting the number of words or phrases which can be combined in a single sentence;

arranging the words or phrases so that modifiers modify only the designated word or phrase; and, supplying the punctuation and conjuctives to create the English text.

BRIEF DESCRIPTION OF THE DRAWINGS

FIGS. 2 through 28 and 30 through 32 illustrate screen displays demonstrating the use of the present invention on a computer equipped to run the system of the present invention on a Microsoft WindowS™ software program on a Microsoft Windows™ capable computer.

DESCRIPTION OF THE PREFERRED EMBODIMENTS

In the description of the present invention, a plurality of computer screens will be shown. It will be understood that the computer screens are illustrative only and that other screens could be used with different formats to perform the same functions. The screens shown in this Description of Preferred Embodiments illustrate screen displays, which have been found particularly effective for use in the entry of data in a medical emergency room application. The system of the present invention is equally effective in other situations where data entry is required.

Figure 1:
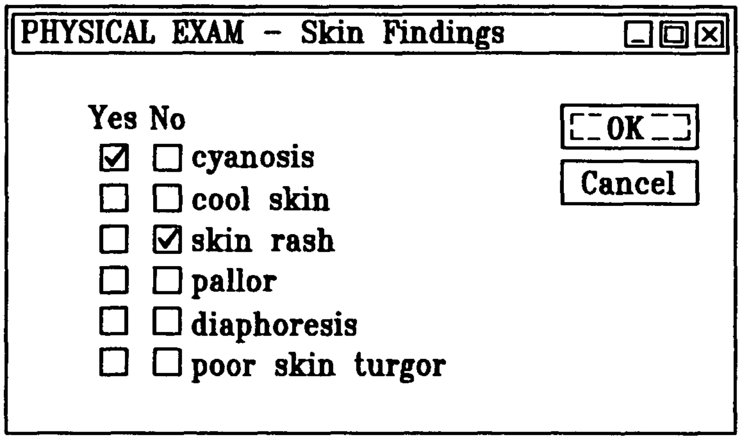
FIG. 1 shows a prior art computer display screen for yes/no data entry.
Figure 2:
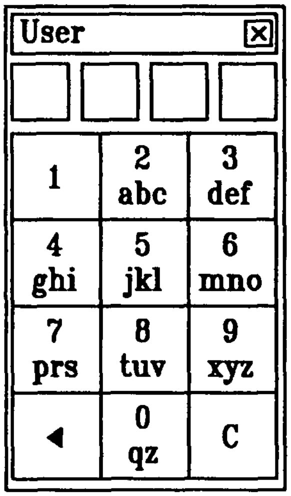

In FIG. 2 a typical security display is shown. The user is required to enter his password to provide security for access to the system.

The system comprises a computer programmed to perform the required functions. The computer can be a handheld terminal, a personal computer, a terminal accessing a suitable computer and the like. The data entry can be by a computer entry pen, by clicks on a mouse by use of a keyboard, or the like. Particularly, in emergency medical room environments a pen-friendly system may be used. After entry of the required password, the system displays a screen (system access display) as shown in FIG. 3. This is a main screen or home view of the program. The upper section headed "My Patients" shows all patients presently assigned to a physician. The lower section, "Patients Waiting," shows a list of patients about whom the program has been notified from another computer such as the hospital's admission system but for whom no medical data has yet been entered into this program.

The workstation used by the physician or other data recorder can be a handheld unit, a personal computer a computer workstation or the like. As indicated previously, the data may be entered by pen strokes, by clicking a mouse, typing on a keyboard or the like. The workstation is also programmed to access a hospital or other mainframe computers to acquire data about the patients presently assigned to the physician. Software and programming for the exchange of such information between computers is well known to those skilled in the art.

In FIG. 4, a patient named "Jack" has been selected for treatment. This patient has been identified by the pointer and in FIG. 5 has been moved to the "My Patients" section which is accomplished by dragging the patient's name from the lower to the upper section of the screen. The patient is now assigned to the attending physician. The physician may also move the new complaint from the lower to the upper section of the screen. This entry allows the physician to begin entering data for the patient who may have not been previously admitted by the hospital admitting system.

In FIG. 6, the physician has identified a patient room for the patient. The physician can also enter the patient's vital statistics, such as name, sex, age, chief complaint, arrival time, etc., using the same technique as for the room number. The system usually discourages changing information of this type, which may have been received from the hospital directly. In addition to the use of pen/tablet devices, other devices may be used which can provide handwriting recognition to support the data entry process. Voice recognition may also be used for this purpose.

With the room number assigned, the physician has a clear view of his/her current patients as shown in FIG. 6. The highlighted patient is identified as the selected patient who will be the subject of the actions described below. It will be understood that the physician could alternatively select a different patient by selecting, tapping or clicking on a different patient. Please note in FIG. 6 at the left under "Clinical" four entries are possible: "History". "Exam"; "Course": and "D×DI." These entries refer to different sections of the system and provide templates, which may be used to enter different types of data.

The "History" section allows the entry of data pertaining to the history of the present illness, a review of systems, a past history (including social history) and may include the first part of a physical exam, if desired. It is into this section that the physician will usually first begin entering data.

The "Exam" should allow the entry of the majority of information regarding a physical examination.

The "Course" section provides for entry of data regarding various procedures and the progress of the case during the course of the patient's visit to the emergency room or hospital departments. The physician can return to this section several times during the course of a patient's visit.

The "D×DI" provides for the entry of clinical impression, prescriptions, work excuse, discharge instructions and the like. This section is generally used by the physician to complete a case.

As indicated previously, these sections appear at the left side of the main screen and can be selected by computer entry pen strokes, by clicking a mouse, typing on a keyboard or the like. Various other operations can be selected for various other software functions from the system access display.

If the physician taps or clicks one of the sections on a selected patient and the patient currently has no current medical record, the program prompts the physician to select the desired template by displaying a template selector as shown in FIG. 7.

Each template provides for entry by the physician of the clinically relevant data for the associated chief complaint. Each template also provides for the entry of data less clinically relevant to the chief complaint. For example, the template for a motor vehicle accident should provide for entry of crucial information about head injuries, which are of a particular concern in such cases. It also should provide for the entry of somewhat detailed information about broken bones, however, it need only provide rudimentary entering capabilities for injuries such as insect bites. For this reason, the program need only allow a single template, which may be selected for a given patient visit.

Figure 8:
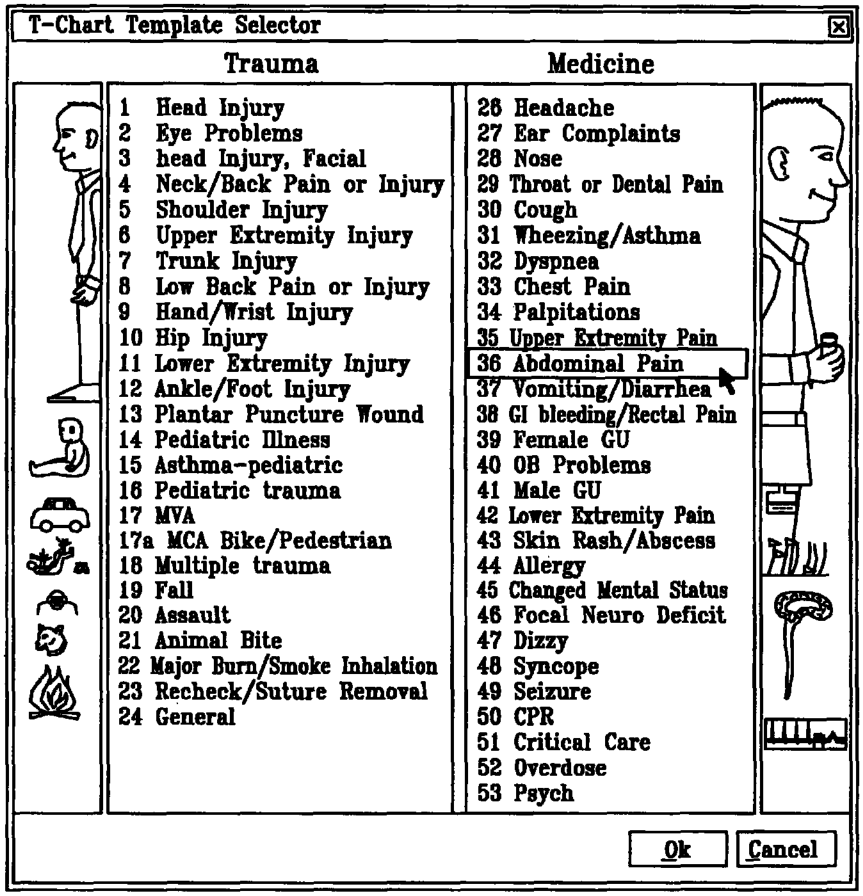

As shown in FIG. 8, in the described template, "Abdominal Pain" has been selected by positioning the arrow on the desired template. Selecting the desired template results in the display of a chart as shown in FIG. 9 for abdominal pain. This illustration shows the "History" section for abdominal pain. The History section under "clinical" is colored as shown. The physician can easily view the other sections by selecting the "Exam", "Course" or "D×DI" buttons. Tapping or clicking the home button beneath the patient's name brings back the original view of the patients on the main screen.

In FIG. 10, a selection is indicated by the arrow that abdominal pain is or will be the chief complaint. The present system does not use conventional check boxes or other data entry methods. The current system has been developed to be readily grasped and used by physicians who are not expert computer users but still appeal to highly computer literate individuals.

It is important that the organization of the data entry points presents itself to the user in a manner that provides effortless orientation for both new and experienced users.

FIG. 10 shows a mouse cursor positioned over a finding of abdominal pain as the chief complaint in the history of present illness portion of the "History" section of a template for abdominal pain.

Please note the small circles to the left of "HPI", "ROS" and "Past Hx." These indicate the availability of sub-templates for these headings. Sub-templates will be discussed in greater detail below.

In FIG. 10, tapping or clicking the heading "abdominal pain" results in a circle around the term "abdominal pain" indicating a positive finding. As shown in FIG. 11, an indication of abdominal pain is shown. In FIG. 12 a further indication has been made that nausea is present. This indication is made in the same way by selecting "Nausea." In FIG. 13, the information has been added that there has been loss of appetite. This is done by tapping or clicking on the "Loss of Appetite" term.

In FIG. 14, it has been indicated that there is no vomiting. Using the secondary mouse button (normally the right button), or tapping with a tablet pen near the right of the word creates a backslash instead of a circle. This indicates a negative finding, in this case, no vomiting.

Figure 15:
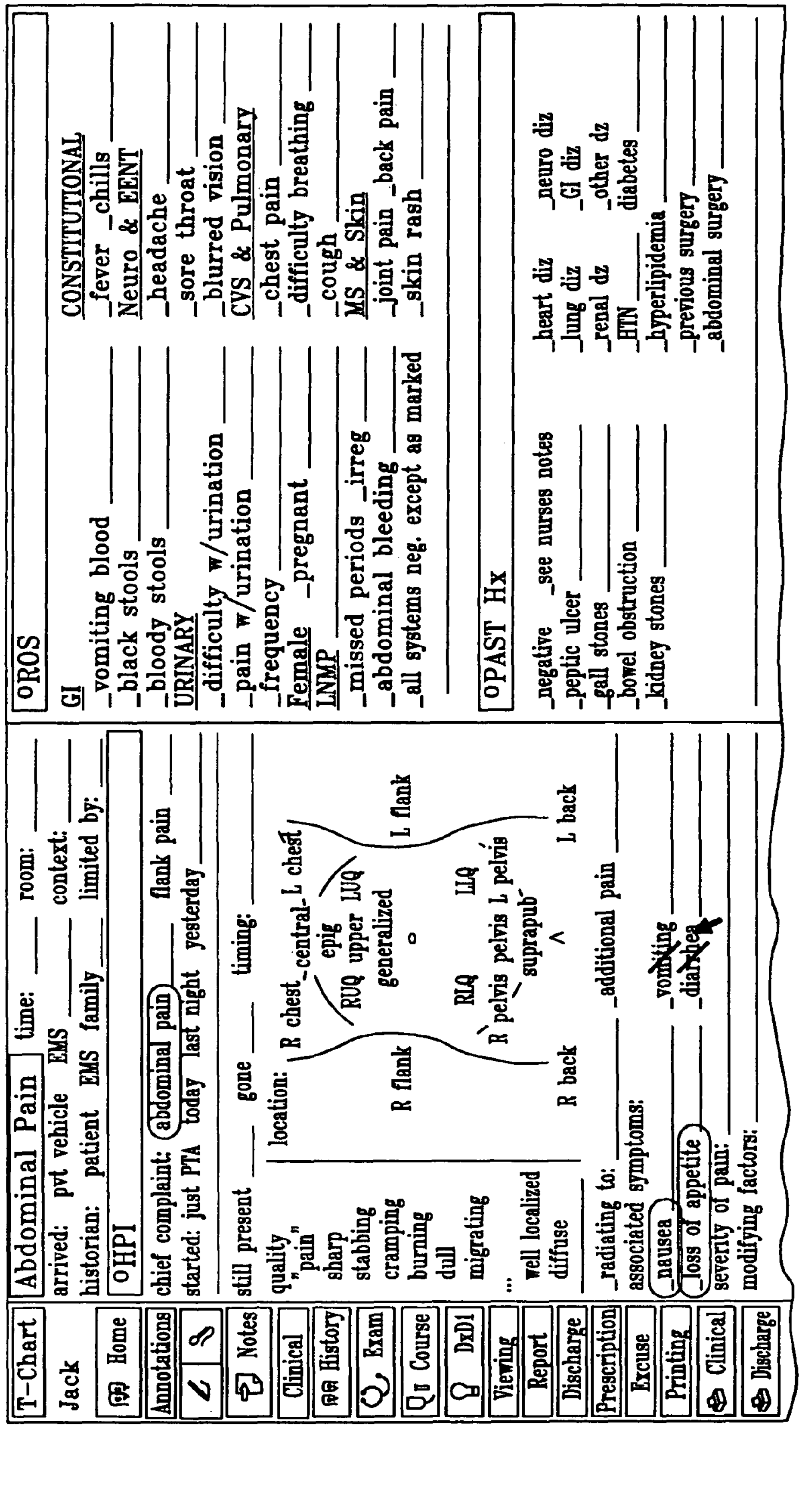

In FIG. 15, a further indication has been made in the same way that there is no diarrhea.

Although the circles and backslashes provide an ideal visual representation of findings, it is necessary to present this information in a text format which can be stored in hospital archives, transmitted, printed and viewed without the requirement for a graphical presentation. Clicking the report entry as shown on the main screen beneath the viewing section, causes the program to generate a textual (prose) representation of the remarks entered by the physician. In FIG. 16, the clinical report of the information entered previously is shown in textual form.

In FIG. 17, the cursor has been placed on the line at "Cough" and selecting the entry at the line may permit the entry of more detailed information. The system provides methods for going into greater detail. The mouse pointer shown over the line in FIG. 17 extending to the right of "Cough" permits clicking on the line which brings up additional details (modifier) one might wish to describe for that finding as shown in FIG. 18.

As shown in FIG. 19, the recorder has indicated on the modifier that the cough is severe, that it has been productive, thick, green and blood-tinged but with no "frank blood". These details are entered by circles and backslashes as described previously.

The clinical report based upon this additional information is show n in FIG. 20.

In FIG. 21, it is indicated that by clicking on the "X" at the upper right the modifier can be deleted. It can also be deleted by clicking or tapping another finding somewhere else on the screen.

After the modifier has been deleted, (FIG. 22) the additional information remains on the line following "Cough" indicating that more information is available.

Figure 23:
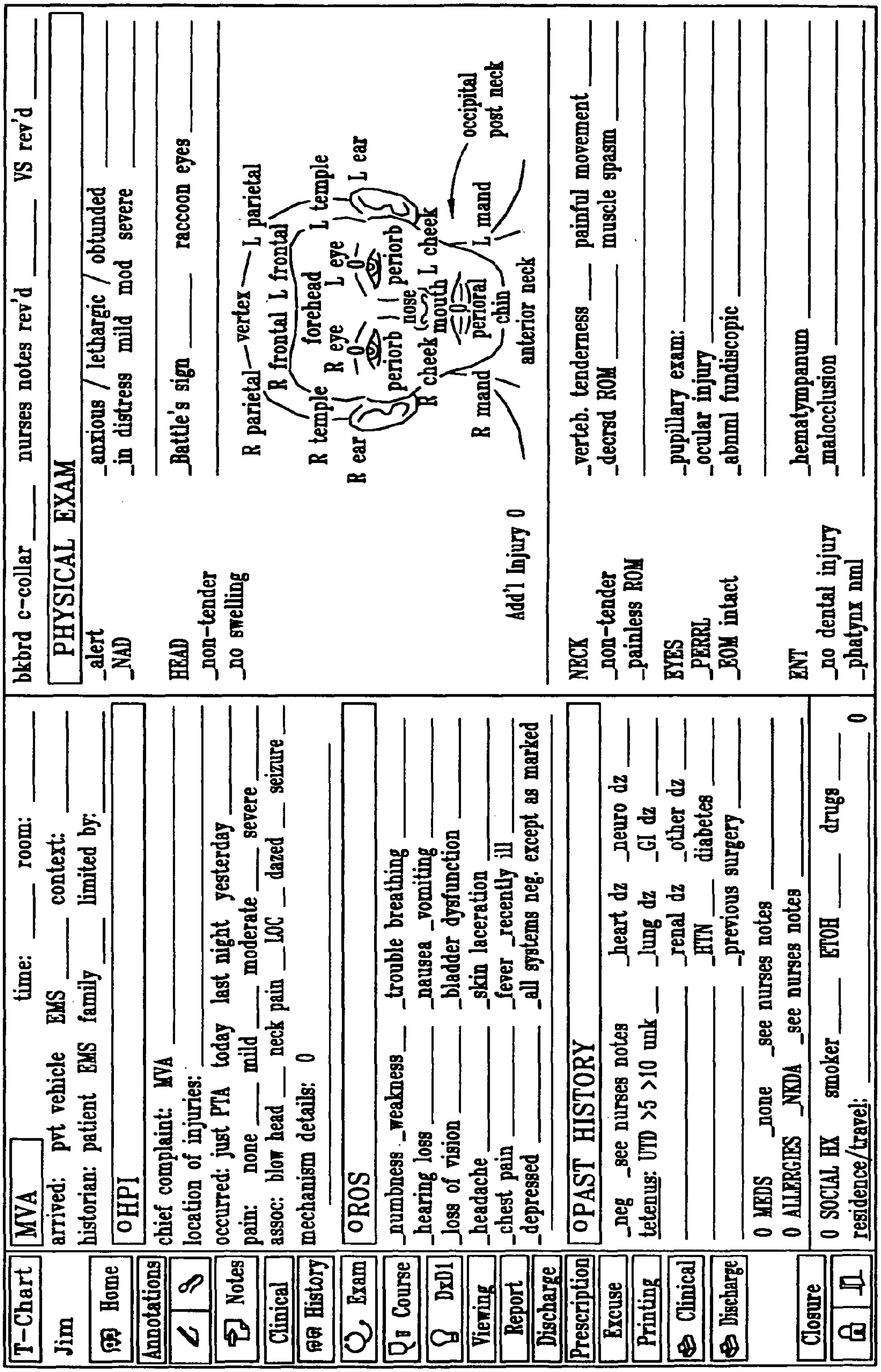

In FIG. 23-26, a set of template sheets is shown illustrating the differences between the "History", "Exam", "Course", and "D×DI" sheets. All of these templates are for a motor vehicle accident, with FIG. 23 showing a sheet for "History," FIG. 24 shows the "Exam" sheet, FIG. 25 shows a sheet for "Course," and FIG. 26 shows a sheet for "D×DI." These sheets as discussed previously relate to different aspects of a patient's treatment. While not discussed above, the templates may also include sub-templates, which permit the entry of additional data about any particular heading shown on the template. Various findings in the sub-templates may also include modifiers, which include additional entries, which may be made with respect to any of the conditions referred to on the sub-template.

Figure 27:
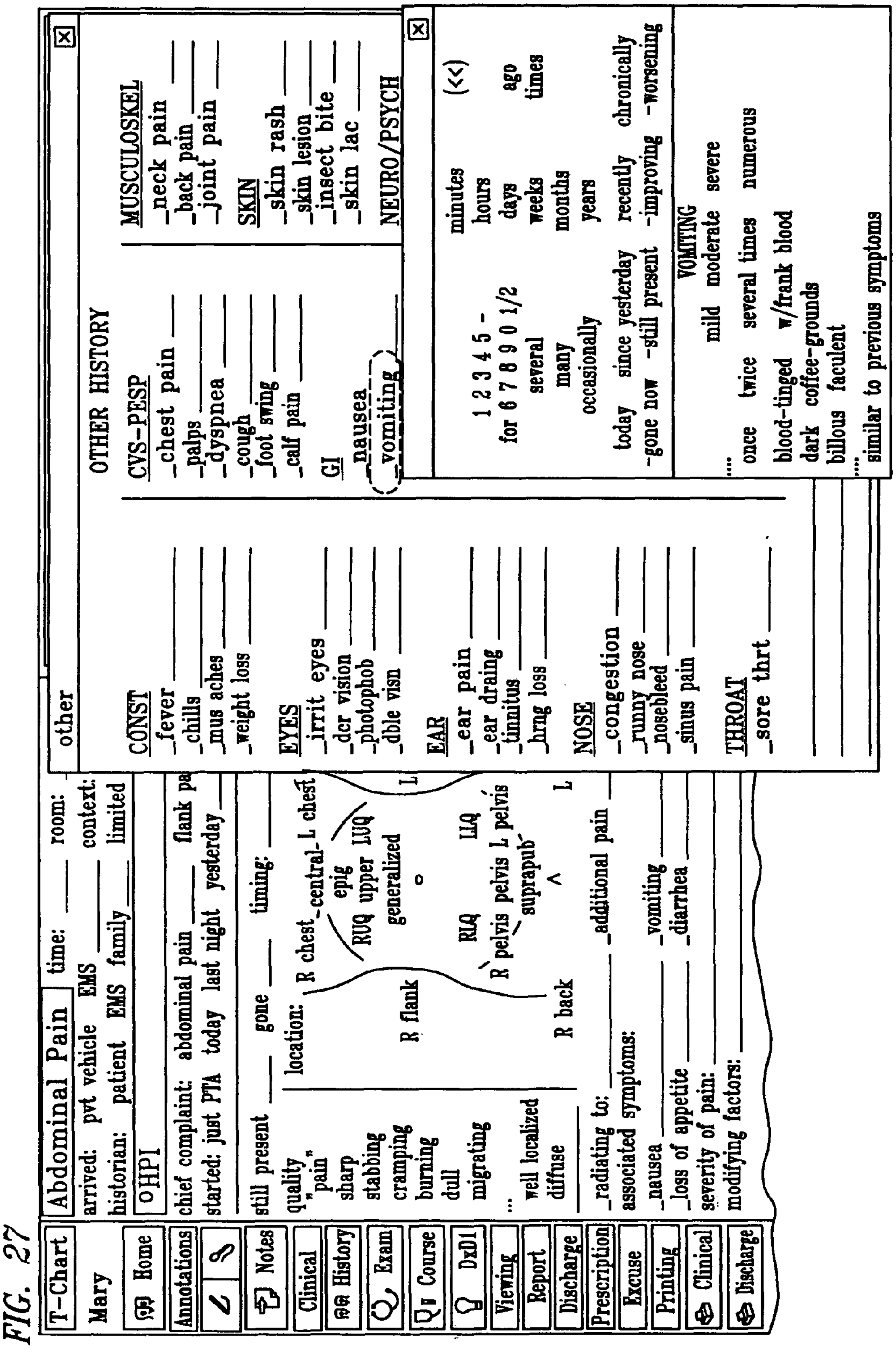

In FIG. 27, a sub-template is shown. The sub-template is headed "Other History." This sub-template is available by clicking on the circle in front of the heading "HPI." This sub-template enables the entry of additional information.

As further shown in FIG. 27, a modifier is available and is shown on the sub template in connection with vomiting. Additional information can be shown by marking entries on the modifier as discussed previously.

As shown, these screen displays demonstrate one embodiment of the system of the present invention for use in a hospital emergency room. As indicated, this system can be used for a wide variety of data entry applications. The system registers a positive finding when a tablet pen touches the left side of an unmarked finding. It should be appreciated that any number of systems can be used for data entry. Typically in the current system, a negative finding is registered when the user right clicks or taps the right side of an unmarked finding. The selection of a previously marked finding clears or reverses the indicated mark thereby providing the user with a intuitive mechanism for correcting data entry errors. Those discussed herein are preferred and have been found to be effective. They should be considered to be illustrative disclosures of methods for entering, reporting and distributing the data.

On tablet-based systems, in addition to recognizing the left and right taps as requests to enter positive and negative findings respectively, it is desirable for the software to recognize pen movements, circling or backslashing the word and to translate those into positive and negative findings. The effect observed by the user is that drawing a circle or a backslash around the typesetting enters the positive or negative findings. The circles and backslashes can be used to illustrate multiple positive or negative findings.

The forms are desirably laid out to permit the user to readily enter data with a minimum of effort. Accordingly, the forms should provide the ability to enter most data by yes/no entries.

In the present system, most of the templates are desirably designed so that a simple yes/no answer can be used to indicate the data. For example, "The patient has chest pain." or "The patient does not have chest pain." Sometimes it is desirable to provide more information. If specified by the form layout, the software must present a visual cue that entry of detailed findings is possible. One such visual cue is to draw a horizontal line to the right of the finding, as illustrated on all findings in the ROS section in FIG. 9. In such cases, the user can click or tap the horizontal line in order to request an opportunity to enter more detailed information about the finding in question. The software responds by presenting one or more of the following data entry options, as specified by the layout: (1) simple text, (2) sentence builders, and (3) modifiers. The user may enter data as desired, and then dismiss the data entry option(s), generally by either (a) clicking or tapping a "close" icon associated with the data entry option or (b) activating data entry into an unrelated findingc by clicking or tapping it.

As illustrated previously, the software in the system should present a visual clue that detailed information has been entered for a given finding. For instance, as shown in FIG. 22 after the word "Cough" additional information is shown. This provides an indication that more information is available with respect to this finding.

It is not considered necessary that the visual clue for detailed findings actually shows the detailed findings completely. It is sufficient that the indication is made that detailed findings were recorded.

In addition for providing for the entry of data as a detailed finding, the software should also enter simple text (simple sentences) that stands on its own. This should be enterable using conventional methods such as the use of a backspace, left and right arrow and similar navigation keys, word wrap, use of scroll bars and the like to access the entire text and voice or handwriting recognition should be accepted. The entered text should then be displayed over the lines near the entries or at other places as indicated. If the entered text is too lengthy to appear within the available space a visual clue should be indicated.

The entry of detailed findings can be augmented with sentence builders to accelerate entry of simple text as shown in FIG. 27. The upper portion of the pull-down shown permits selection of for instance “for”, “several” and “days”. This would result in a report that, “The patient has vomiting (for several days)”. Additional information can be shown by typing in the data entry space provided. Information may also be shown by selecting the findings on the modifier (pull-down). Sentence builders are another data entry option, which may be invoked in the form design.

This system may also be used with a medical records distribution system. Typically such medical record distribution systems comprise a computer programmed to access a database of such medical records and a database including distribution options. These options may include distribution of the information, for instance, to a second or additional physicians, to insurance companies, or other payers and the like. Normally, the distribution option is selectable for each medical record, which is to be distributed. The selected option may be implemented by electronically distributing the records via e-mail or other similar communication systems or the distribution system may produce a hard copy letter or the like, of the medical records to be distributed with suitable addresses for mailing to the desired recipients. Desirably, the system is also in communication with a database, which maintains a record of the distributed medical records and of the recipients of those medical records.

Figure 28B:
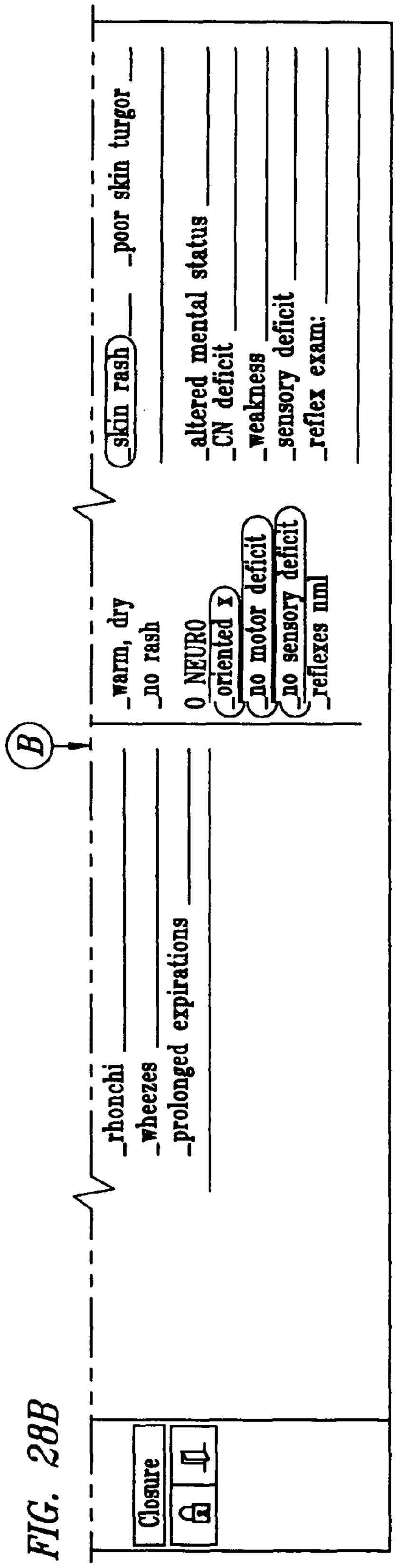

In FIG. 28, an exam template for abdominal pain is shown. On this template, various findings have been indicated positively by circles.

Figure 29:
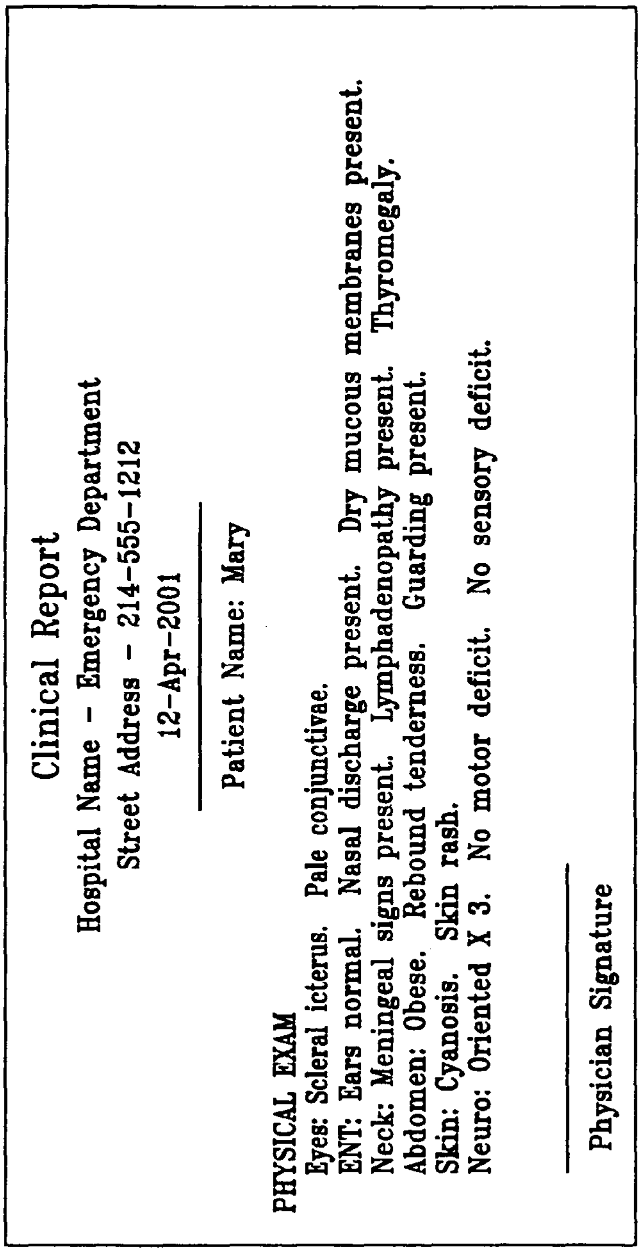
FIG. 29 shows a clinical report produced by the system of the present invention; and, FIGS. 33 through 37 demonstrate a program for producing reports from the system of the present invention.

A clinical report is shown in FIG. 29 reporting the data entered in FIG. 28. In FIG. 28, by clicking on FEM GENITALIA a sub-template headed “Pelvic Exam” is available as shown in FIG. 30. Certain findings have been indicated on this sub-template as shown by circles.

In FIG. 31, a clinical report including this information, in addition to that available previously from FIG. 28, is shown.

Figure 32:
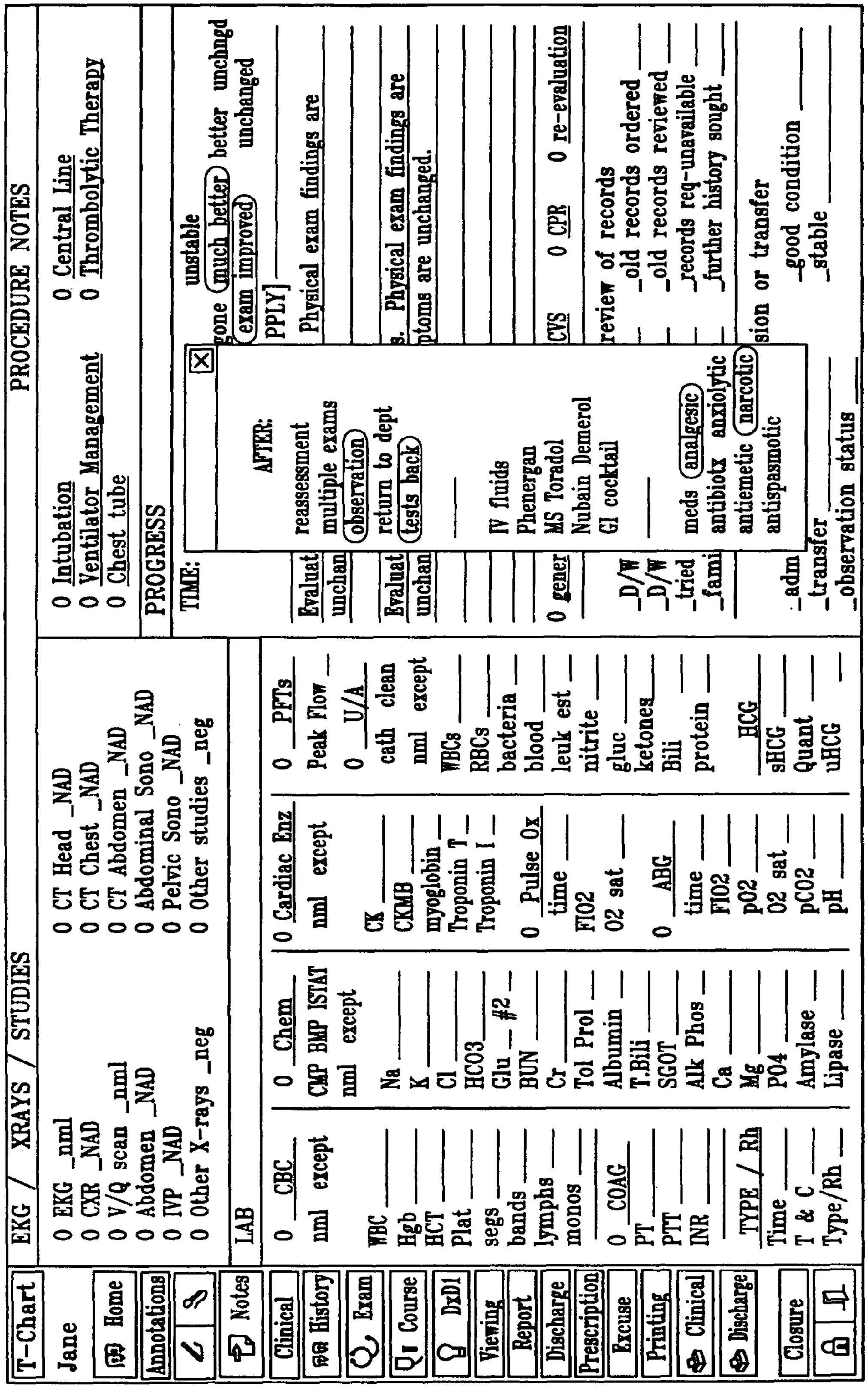

By clicking on the line following the entry for “Time” under “Progress” in FIG. 32, a “Progress and Procedures Note” is available for indicating changes in the patient’s condition, medicines administered and the like. In the note shown, the patient has been subjected to observation, tests have been returned, an analgesic has been administered and a narcotic has been administered. As a result of this treatment, the patient’s condition is much better and the exam findings have improved. It will be noted that under the “Note” are notes from previous entries on previous “Notes.” This allows the physician to enter patient treatment information sequentially. If it is desired to enter the time, it can be entered, but is not necessary. It is generally considered more important to enter the sequence of treatment rather than the exact times that the treatments are performed. In FIG. 33 the entered data is shown for the notes cumulatively in the “Progress” section.

In FIG. 34, the clinical report is provided. The “PAST HISTORY” includes data entered previously on a History template, the “PHYSICAL EXAM” information includes information previously entered on an Exam template and the “PROGRESS AND PROCEDURES” notes are entered on the Progress and Procedures section.

The reports of the recorded data are typically made by programming, which produces the reports as a plurality of simple sentences having a single object or a single clause.

Figure 35:
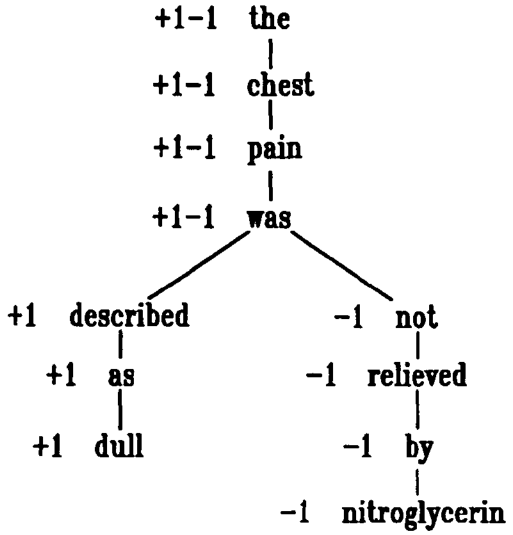

As shown in FIG. 35, two phrases are shown in a diagram for condensing these phrases. The phrases are “The chest pain was described as dull.” and “The chest pain was not relieved by nitroglycerin.” These two phrases have been drawn as a diagram which shows the essential content of an internal data structure created by the computer program upon processing those phrases. The preferred form of the internal data structure is generally a data tree, although other suitable structures known to those skilled in the art could be used.

The program builds the tree by processing each phrase in turn. Each successive word in each phrase is added to the tree so that the collective content of all the phrases is contained in the tree as suggested in FIG. 35.

The program also maintains a tally of the number of positive and negative phrases found for each word in the tree. As shown in FIG. 35, the first four words of all phrases in this example are “the”, “chest”, “pain” and “was, and each of these is associated with one positive phrase (“+1” in the diagram) and one negative phrase (“−1” in the diagram). As described below, the program may permit the author flexibility in the manner in which the program generates text from the tree thus produced. The information required for the program to accommodate the author’s wishes, such as desired ordering of phrases or use of conjunctive words as described below, can be stored in the nodes of the tree. The particular information to be stored in each node depends upon the options desired.

To generate sentences from the tree, the program traverses the nodes of the tree, nominally in order of their appearance in the tree, but altered as necessary to reflect any desired ordering imperatives. Successive nodes such as “the”, “chest”, “pain” and “was” in FIG. 3) constitute a common pretext for any sentence(s) generated from the least significant, or rightmost, node, in this case “was”. The traversal process at a node which branches into two or more subtrees, such as “was” in FIG. 35, produces the necessary sentence(s) as the common pretext, in this case “The chest pain was” followed by a list of phrases generated from each subtree, such that any positive phrases are extracted from the subtrees and combined in an “a, b, c and d” pattern, and similarly any negative phrases are extracted from the subtrees and combined in an “a, b, c or d” pattern, and such that if both negative and positive phrases were found, the positive phrases come first and are followed by the conjunctive word “but” and then the extracted negative phrases.

Accordingly, the sentence resulting from the combination of the phrases in FIG. 35 would say, “The chest pain was described as dull but not relieved by nitroglycerin.” In the construction of the sentences, “but” is used to indicate a negative and in the event that more than one negative clause is used, the clauses may be separated by “or’s.” In the recitation of a plurality of positive phrases, the phrases are separated by “and’s.” Arbitrarily, it has been determined the sentences containing more than five clauses are unduly complex and the combination of single sentences is preferably limited to five clauses.

Figure 36:
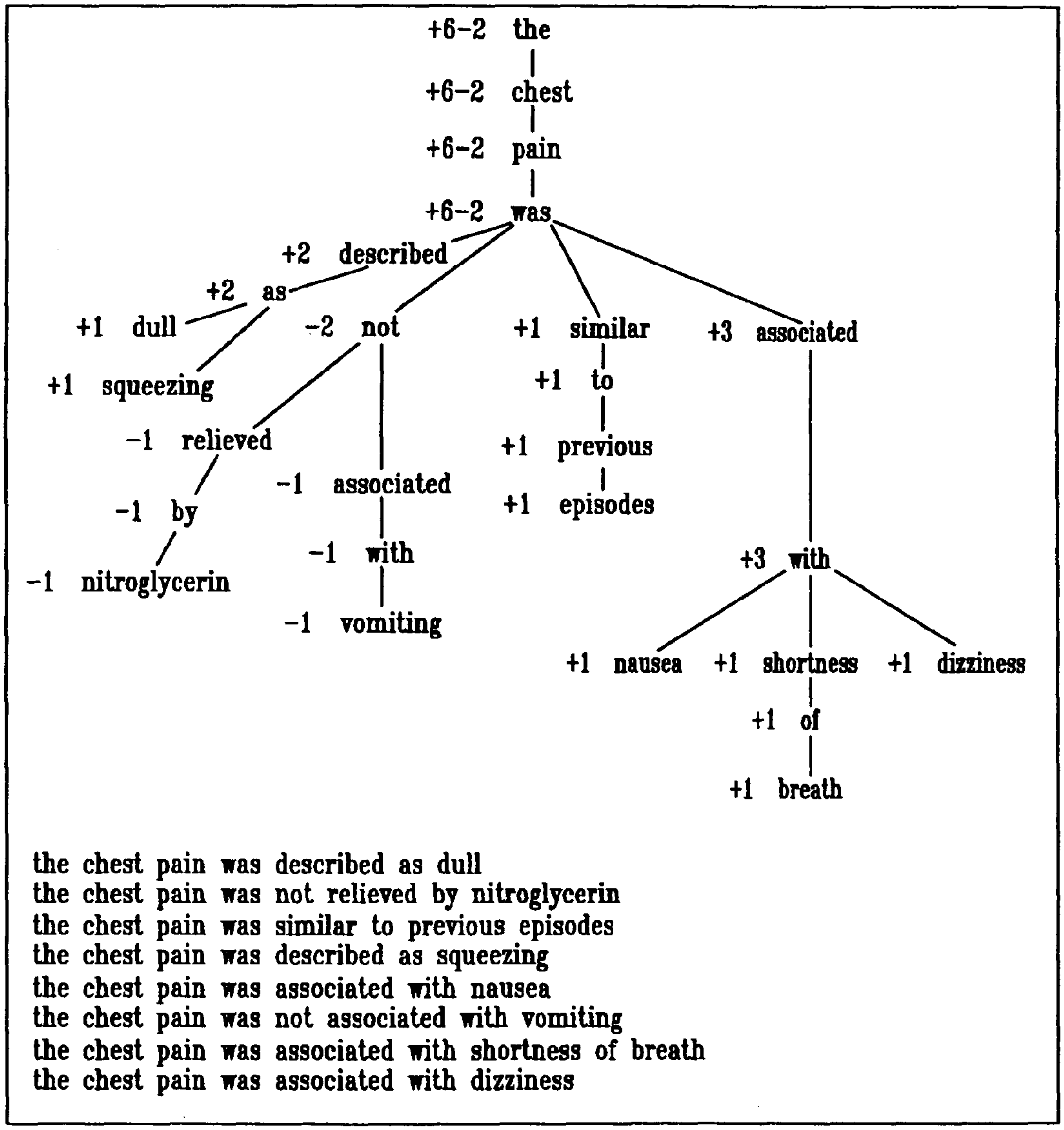

In FIG. 36, a more complicated diagram is shown. The eight sentences shown beneath the diagram are to be combined into more complex and more readable sentences. It will be noted that “the” appears in six positive statements and two negative statements. This assignment of values continues through the word “was.” “Was” is followed by the word “described” twice, indicated by the numeral “+2” beside the word “described.” The word “as” similarly appears twice and the words “dull” and “squeezing” each appear once. A similar assignment of numbers is found with the negative statements which are shown directly beneath “was” with a “−2” being assigned to "not" and "−1's" being assigned to the words following the "not." Similarly, the word "similar" occurs once and this is shown by the "+1's". The word "associated" follows the word "was" three times and this is indicated by the numerals "+3" with each of the individual phrases following from the word "associated" being numbered with "+1's". The net result of the combination is that it is not possible to combine all of the clauses without exceeding the limitation of five clauses per sentence.

The traversal process described above works well even when a tree contains complex nested subtrees such as that shown in FIG. 36. In such a case, the subtrees are traversed as before and the resulting text still reads well. New sentences can be started at any given node, whenever necessary either to avoid exceeding the maximum number of clauses, or to comply with the author's requirements. Accordingly, while a number of combinations might be possible, the most likely combination is the following. "The chest pain was described as dull and squeezing and similar to previous episodes but not relieved by nitroglycerin or associated with vomiting. The chest pain was associated with nausea, shortness of breath and dizziness."

Similar applications can be made to any group of sentences produced by the program, which produces simple sentences having a single object or clause. Clearly, the assignment of a limit of five clauses per sentence is arbitrary and fewer or more clauses could be used if desired. While this embodiment is relatively specific, it should be understood that a large number of programs using this type of approach could be used to convert the simple sentences to longer sentences to more accurately and readably convey the data.

In addition to the limitations discussed above, the program is designed to permit the author flexibility in the expression. For instance, in the combination of the two sentences referred to in FIG. 35, the resulting sentence could also by produced by an option which causes the sentence to read "The chest pain was described as dull, but was not relieved by nitroglycerin." Clearly the use of the second occurrence of the word "was" is optional and may be preferred by some users. Further, the program offers the capability to select a conjunction of choice. For instance, "and", "or" or "nor" could be selected. The appropriate conjunctive is selectable by the user. The program will provide conjunctives as indicated previously with "and" separating positive clauses and "or" separating negative clauses with a "but" separating the positive and negative clauses, unless modified.

The program also permits the user to alter the order of the clauses by assigning selected number values to the clauses to designate the order in which they appear in the sentence. The simple sentences may be grouped as desired in the combined sentence by designating the clauses in the order in which they are to appear in the combined sentence by assigning numbers to each of the clauses. As a further feature, selected words may be left in the combined sentence which would otherwise have been deleted by bracketing or indicating the words which are to be retained which would normally have been deleted.

It may be desirable in some instances to eliminate redundancy and in other areas to create deliberate redundancy. In general, considerable flexibility is let to the user of the program to generate the combined sentence to most accurately reflect the combined meaning of the simple sentences.

Many variations and modifications are possible within the scope of this technique. In general, special punctuation may be used as an instruction to the program to add words, delete words, reorganize words and the like. Further, the desired punctuation to arrange the clauses in a desired order may be specified on the template or sub-template or modifier sheets so that when the simple sentences are produced, they are produced with the desired indicators to cause the combined sentence to be produced in a desired form. Other variations may also appear desirable to those skilled in the art based upon the foregoing description.

Further with reference to FIG. 34, please note that the clinical report is organized to recite the name of the template from which the data is obtained. In the case of the physical exam, it is laid out to refer to the section of the physical exam from which the data is entered. for instance, the data is entered for: "Eyes", "ENT", "Neck", "Abdomen", "GU", "Skin", and "Euro." In the Progress and Procedures section, the data reported is all reported under the ED Course, which is the section in which the evaluation and reassessment data is reported.

In FIG. 37, a plurality of sentences is shown with an indication ahead of each clause indicating that there is to be no clause reduction. This embodiment may be desirable in many instances with a prior medical history where it is desired that the phrases be made available to the physician without modification.

In further modifications, for instance with the vomiting modifiers discussed above, it may be indicated that severe vomiting is present, that the vomit is blood tinged and contains frank blood. This sentence may be varied by suitable punctuation to read "He has had severe blood tinged vomiting containing frank blood." or alternatively could be punctuated to read "He has had severe blood tinged vomiting. The vomitus contains frank blood." The development of punctuation to position the clauses relative to each other and the punctuation available to remove redundancy and to properly place adjectives and the like permits tremendous flexibility in the construction of the complex sentences.

In summary, the present system is effective to record medical data or other data which is conveniently entered by a professional or other observer by entering yes/no entries into a system to enter the data effectively, transmit it to a desired records system or otherwise make it available for use with respect to the individual, reported by the recorder or by another party.

While the description above has illustrated the invention specifically with respect to a medical emergency room data entry system, it should be understood that this system is much more widely usable in other applications although the use of the system is particularly effective for the entry of data in a medical emergency room situation.

Having thus described the invention by reference to certain of its preferred embodiments, it is noted that the embodiments described are illustrative rather than limiting in nature and that many variations and modifications are possible within the scope of the present invention. Many such variations and modifications may be considered to be obvious or desirable to those skilled in the art based upon the foregoing description of preferred embodiments.

Having thus described the invention, we claim:

1. A method for generating a clinical report in a natural language text representation, said method operative within a computing device for controlling said computing device to perform the functions of:

- compiling data representing a selected state of a plurality of data elements which symbolize specific questions pertaining to a medical condition of a patient, including compiling positive findings selected by a user, and compiling negative findings selected by the user;
- building a tree structure by processing individual phrases, said individual phrases generated dynamically upon receiving individual selections of said data elements, wherein a selection of a data element of the plurality of elements generates an individual phrase, wherein each individual successive word in each phrase is added to the tree structure;

associating each word in the tree structure with positive and negative values of a selected data elements, a positive value corresponding to a positive finding selected by the user and a negative value corresponding to a negative finding selected by the user, wherein the associating includes identifying a first tally corresponding to the number of occurrences of each word in an individual phrase generated by a selection of a positive value of the selected data element and identifying a second tally corresponding to the number of occurrences of each word in an individual phrase generated by a selection of a negative value of the selected data element; and generating a textual prose representation of correlated compiled data by using a built one of said tree, wherein said generating includes combining a plurality of words in the tree structure into at least one sentence for said textual prose representation by correlating the first tally and the second tally.

2. The method of claim 1 further comprising:

storing said textual prose representation.

3. The method of claim 2 further comprising:

displaying said textual prose representation.

4. The method of claim 1 further comprising:

generating said selected state data by a user accepting or rejecting individual data elements contained in a listing of said data elements.

5. The method of claim 4 wherein said generating said selected state data by a user accepting or rejecting individual data elements contained in a listing of said data elements comprises:

monitoring the location of said user's taps with a tablet pen.

6. The method of claim 4 wherein said generating said selected state data by a user accepting or rejecting individual data elements contained in a listing of said data elements comprises:

monitoring said user's primary and secondary mouse buttons.

7. The method of clam 1 wherein said data elements correspond to single-word itemized medical symptoms.

8. The method of claim 1 wherein at least one word in said at least one sentence occurs in an individual phrase generated by a selection of a positive value of the selected data element.

9. The method of claim 8 further comprising adding a conjunctive word to said at least one sentence; and combining one or more words occurring in an individual phrase generated by a selection of a negative value of the selected data element into said at least one sentence.

10. A method for generating a natural language report, said method comprising:

presenting, on a computer display, a screen presentation having a plurality of selectable data elements which correspond to clinical data items;

correlating information corresponding to a selected state of said selectable data elements, including compiling positive findings selected by a user, and compiling negative findings selected by the user, wherein a positive value corresponds to a positive finding selected by the user and a negative value corresponds to a negative finding selected by the user;

building a tree structure by processing individual phrases, said individual phrases generated dynamically upon receiving individual selections of said data elements, wherein a selection of a data element of the plurality of elements generates an individual phrase, wherein each individual successive word in each phrase is added to the tree structure;

associating each word in the tree structure with positive and negative values of a selected data elements, wherein the associating includes identifying a first tally corresponding to the number of occurrences of each word in an individual phrase generated by selection of a positive value of the selected data element and identifying a second tally corresponding to the number of occurrences of each word in an individual phrase generated by a selection of a negative value of the selected data element;

generating one or more narrative sentences in a report conveying said correlated information, using the tree structure to generate the one or more narrative sentences, wherein said generating includes combining a plurality of words in the tree structure into at least one sentence for said one or more narrative sentences by correlating the first tally and the second tally; and generating a heading in said report, said heading corresponding to a category of selectable data elements displayed on at least a portion of the screen presentation wherein said heading is generated after a selection of a corresponding data element is made.

11. The method of claim 10 wherein said screen presentation comprises multiple portions having selectable data elements corresponding to the portions and said generating a heading in said report includes generating a heading for any portion having a data element which has been selected.

12. The method of claim 10 further comprising, after generating a narrative sentence corresponding to information from a selected data element, correlating additional data which corresponds to the selected data elements into said generated narrative sentence.

13. The method of claim 10 further comprising:

presenting, on said computer display, a second screen presentation having a plurality of selectable data elements which correspond to clinical data items;

correlating information corresponding to a selected state of said selectable data elements of said second screen presentation;

generating one or more narrative sentences in a report conveying said correlated information; and generating a second heading in said report, said second heading corresponding to data elements displayed in said second screen presentation.

14. A computing device programmed to implement a medical emergency room computing application for generating a clinical report, said computing device comprising:

means for presenting to a user sets of displays, each display corresponding to a phase of a patient encounter and each display having a plurality of data entry points which symbolize specific questions pertaining to a medical condition of a patient;

means for allowing said user to accept or reject individual ones of said medical condition data entry points by selecting positive findings and selecting negative findings, wherein at least one of said medical condition data entry points includes a textual representation of said medical condition, the textual representation being the actual textual label representing the medical condition, the selection of positive findings being performed on the textual representation of said medical condition and the selection of negative findings being performed on the textual representation of said medical condition, wherein the selection of the positive finding causes a first visual indicator to be displayed on the textual representation of said medical condition, and the selection of the negative finding causes a second visual indicator to be displayed on the textual representation of said medical condition, the first visual indicator being different than the second visual indicator;

means for building a tree structure by processing individual phrases, said individual phrases generated dynamically upon the user accepting/rejecting a data entry point in said data entry points, wherein the acceptance or rejection of the data entry point generates an individual phrase, wherein each individual successive word in each phrase is added to the tree structure;

means for associating each word in the tree structure with positive and negative findings of said medical conditions, wherein the means for associating includes means for identifying a first tally corresponding to the number of occurrences of each word in an individual phrase generated by an acceptance of a data entry point in said data entry points and identifying a second tally corresponding to the number of occurrences of each word in an individual phrase generated by a rejection a data entry point; and means for conveying said accepted/rejected medical condition questions as one or more textual narrative sentences in a clinical report, using said tree structure to compose said textual narrative sentences by combining a plurality of words in the tree structure and by correlating the first tally and the second tally, wherein said report is generated dynamically when a given data entry point is accepted/rejected.

15. The computing device of claim 14 wherein said means for conveying said accepted/rejected medical condition questions as one or more textual narrative sentences is configured to selectively convey information from a plurality of questions in a single sentence while also limiting an amount of said information to be used in said single sentence to be less than a pre-determined maximum number of accepted/rejected questions for said sentence.

16. The computing device of claim 14 further comprising:

means for organizing said one or more textual narrative sentences under one or more headings within said clinical report.

17. The computing device of claim 16 wherein the headings correspond to the phase of the patient encounter from which the accepted/rejected data elements originate.

18. The computing device of claim 17 wherein the headings are dynamically generated when a user accepts/rejects a data entry point within the respective phase.

19. The method of claim 4 wherein said combining a plurality of words in the tree structure into at least one sentence includes reducing redundant words from a plurality of individual phrases generated by selections of data elements.

20. The method of claim 10 wherein said combining a plurality of words in the tree structure into at least one sentence includes reducing redundant words from a plurality of individual phrases generated by selections of data elements.

21. The computing device of claim 14 wherein said combining a plurality of words in the tree structure includes reducing redundant words from a plurality of individual phrases generated by acceptances/rejections of data entry points.

* * * * *

UNITED STATES PATENT AND TRADEMARK OFFICE

CERTIFICATE OF CORRECTION

PATENT NO. : 8,909,595 B2
APPLICATION NO. : 11/132948
DATED : December 9, 2014
INVENTOR(S) : Woodrow W. Gandy et al.

It is certified that error appears in the above-identified patent and that said Letters Patent is hereby corrected as shown below:

In the Specification:
At column 3, line number 64, delete "“History”." and replace with --“History”;--.
At column 3, line number 64, delete "“Course”:" and replace with --“Course”;--.
At column 5, line number 42, delete “show n” and replace with --shown--.
At column 6, line number 50, delete “findingc” and replace with --finding--.
At column 8, line number 32, delete “FIG. 3)” and replace with --FIG. 35--.
At column 9, line number 60, delete “let” and replace with --left--.
At column 10, line number 13, delete "“Euro”" and replace with --“Neuro”--.

Signed and Sealed this
Seventeenth Day of March, 2015

Michelle K. Lee
*Director of the United States Patent and Trademark Office*